(12) United States Patent
Jackson et al.

(10) Patent No.: US 12,137,945 B2
(45) Date of Patent: *Nov. 12, 2024

(54) PIVOTAL BONE ANCHOR SYSTEM WITH MODULAR RECEIVER SUB-ASSEMBLIES AND UNIVERSAL BONE ANCHORS

(71) Applicant: Roger P. Jackson, Prairie Village, KS (US)

(72) Inventors: Roger P. Jackson, Prairie Village, KS (US); James L. Surber, Kansas City, KS (US); Nathaniel D. Ginzton, Boise, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 18/178,486

(22) Filed: Mar. 3, 2023

(65) Prior Publication Data
US 2023/0200862 A1 Jun. 29, 2023

Related U.S. Application Data

(63) Continuation of application No. 17/275,923, filed as application No. PCT/US2019/051189 on Sep. 13, 2019, now Pat. No. 11,596,449.
(Continued)

(51) Int. Cl.
*A61B 17/70* (2006.01)
(52) U.S. Cl.
CPC ...... *A61B 17/7038* (2013.01); *A61B 17/7007* (2013.01)
(58) Field of Classification Search
CPC .................................. A61B 17/7032–17/704
See application file for complete search history.

(56) References Cited

U.S. PATENT DOCUMENTS

| 5,669,911 A | 9/1997 | Errico et al. |
| 5,672,176 A | 9/1997 | Biedermann et al. |

(Continued)

FOREIGN PATENT DOCUMENTS

| DE | 102013204726 | 9/2014 |
| EP | 1857064 | 11/2007 |

(Continued)

*Primary Examiner* — Julianna N Harvey
(74) *Attorney, Agent, or Firm* — Polsinelli PC

(57) ABSTRACT

A pivotal bone anchor system includes a plurality of bone anchors with rounded capture portions having a circumferentially extending outer engagement surface without flat side faces. The system also includes multi-planar receiver sub-assemblies, each comprising a multi-planar receiver defining a cavity with a multi-planar seating surface, and a multi-planar pivoting retainer configured for multi-planar motion upon engagement with both the multi-planar seating surface and the outer engagement surface of a bone anchor. The system further includes uni-planar receiver sub-assemblies, each comprising a uni-planar receiver defining a cavity with a uni-planar seating surface, and a uni-planar pivoting retainer configured for uni-planar motion upon engagement with the uni-planar seating surface and the outer engagement surface of another bone anchor. The capture portions of the bone anchors are configured for capture by either a multi-planar or uni-planar receiver sub-assembly without further modification or adjustment.

16 Claims, 40 Drawing Sheets

Related U.S. Application Data

(60) Provisional application No. 62/810,361, filed on Feb. 25, 2019, provisional application No. 62/731,023, filed on Sep. 23, 2018.

(56) References Cited

U.S. PATENT DOCUMENTS

| | | | |
|---|---|---|---|
| 5,690,630 | A | 11/1997 | Errico et al. |
| 5,782,833 | A | 7/1998 | Haider |
| 5,797,911 | A | 8/1998 | Sherman et al. |
| 5,885,286 | A | 3/1999 | Sherman et al. |
| 6,010,503 | A | 1/2000 | Richelsoph et al. |
| 6,063,090 | A | 5/2000 | Schläpfer |
| 6,090,111 | A | 7/2000 | Nichols |
| 6,146,383 | A | 11/2000 | Studer et al. |
| 6,254,602 | B1 | 7/2001 | Justis |
| 6,280,442 | B1 | 8/2001 | Barker et al. |
| 6,355,040 | B1 | 3/2002 | Richelsoph et al. |
| 6,471,705 | B1 | 10/2002 | Biedermann et al. |
| 6,485,491 | B1 | 11/2002 | Farris et al. |
| 6,485,494 | B1 | 11/2002 | Haider |
| 6,540,748 | B2 | 4/2003 | Lombardo |
| 6,565,565 | B1 | 5/2003 | Yuan et al. |
| 6,626,908 | B2 | 9/2003 | Cooper et al. |
| 6,740,086 | B2 | 5/2004 | Richelsoph |
| 6,835,196 | B2 | 12/2004 | Biedermann et al. |
| 6,837,889 | B2 | 1/2005 | Shluzas |
| 6,905,500 | B2 | 6/2005 | Jeon et al. |
| 6,945,975 | B2 | 9/2005 | Dalton |
| 7,066,937 | B2 | 6/2006 | Shluzas |
| 7,087,057 | B2 | 8/2006 | Konieczynski et al. |
| 7,141,051 | B2 | 11/2006 | Janowski et al. |
| 7,144,396 | B2 | 12/2006 | Shluzas |
| 7,163,539 | B2 | 1/2007 | Abdelgany et al. |
| 7,186,255 | B2 | 3/2007 | Baynham et al. |
| 7,264,621 | B2 | 9/2007 | Coates et al. |
| 7,306,606 | B2 | 12/2007 | Sasing |
| 7,311,712 | B2 | 12/2007 | Dalton |
| 7,377,923 | B2 | 5/2008 | Purcell et al. |
| 7,445,627 | B2 | 11/2008 | Hawkes et al. |
| 7,479,156 | B2 | 1/2009 | Lourdel et al. |
| 7,604,655 | B2 | 10/2009 | Warnick |
| 7,625,396 | B2 | 12/2009 | Jackson |
| 7,686,834 | B2 | 3/2010 | Saint Martin |
| 7,686,835 | B2 | 3/2010 | Warnick |
| 7,695,497 | B2 | 4/2010 | Cordaro et al. |
| 7,749,258 | B2 | 7/2010 | Biedermann et al. |
| 7,766,915 | B2 | 8/2010 | Jackson |
| 7,766,945 | B2 | 8/2010 | Nilsson et al. |
| 7,776,067 | B2 | 8/2010 | Jackson |
| 7,789,896 | B2 | 9/2010 | Jackson |
| 7,789,900 | B2 | 9/2010 | Levy et al. |
| 7,811,310 | B2 | 10/2010 | Baker et al. |
| 7,833,250 | B2 | 11/2010 | Jackson |
| 7,833,251 | B1 | 11/2010 | Ahlgren et al. |
| 7,842,073 | B2 | 11/2010 | Richelsoph et al. |
| 7,875,065 | B2 | 1/2011 | Jackson |
| 7,901,436 | B2 | 3/2011 | Baccelli |
| 7,905,907 | B2 | 3/2011 | Spitler et al. |
| 7,909,830 | B2 | 3/2011 | Frigg et al. |
| 7,914,536 | B2 | 3/2011 | MacDonald et al. |
| 7,942,909 | B2 | 5/2011 | Hammill, Sr. et al. |
| 7,947,065 | B2 | 5/2011 | Hammill, Sr. et al. |
| 7,951,173 | B2 | 5/2011 | Hammill, Sr. et al. |
| 7,967,850 | B2 | 6/2011 | Jackson |
| 7,988,694 | B2 | 8/2011 | Barrus et al. |
| 8,021,397 | B2 | 9/2011 | Farris et al. |
| 8,034,089 | B2 | 10/2011 | Matthis et al. |
| 8,048,112 | B2 | 11/2011 | Suzuki et al. |
| 8,066,744 | B2 | 11/2011 | Justis et al. |
| 8,075,599 | B2 | 12/2011 | Johnson et al. |
| 8,075,603 | B2 | 12/2011 | Hammill, Sr. et al. |
| 8,083,776 | B2 | 12/2011 | Alvarez |
| 8,162,985 | B2 | 4/2012 | Kim |
| 8,197,517 | B1 | 6/2012 | Lab et al. |
| 8,197,518 | B2 | 6/2012 | Hammill, Sr. et al. |
| 8,221,472 | B2 | 7/2012 | Peterson et al. |
| 8,298,265 | B2 | 10/2012 | Purcell et al. |
| 8,308,782 | B2 | 11/2012 | Jackson |
| 8,328,817 | B2 | 12/2012 | Strauss |
| 8,353,932 | B2 | 1/2013 | Jackson |
| 8,361,123 | B2 | 1/2013 | Fanger et al. |
| 8,382,805 | B2 | 2/2013 | Wang et al. |
| 8,398,683 | B2 | 3/2013 | Berrevoets et al. |
| 8,439,922 | B1 | 5/2013 | Arnold et al. |
| 8,444,681 | B2 | 5/2013 | Jackson et al. |
| 8,449,578 | B2 | 5/2013 | Keiser et al. |
| 8,556,938 | B2 | 10/2013 | Jackson et al. |
| 8,562,652 | B2 | 10/2013 | Biedermann et al. |
| 8,628,558 | B2 | 1/2014 | Harvey et al. |
| 8,657,858 | B2 | 2/2014 | Garamszegi et al. |
| 8,663,290 | B2 | 3/2014 | Doubler et al. |
| 8,663,291 | B2 | 3/2014 | Doubler et al. |
| 8,663,298 | B2 | 3/2014 | Keyer et al. |
| 8,696,712 | B2 | 4/2014 | Biedermann et al. |
| 8,876,869 | B1 | 11/2014 | Schafer et al. |
| 8,882,817 | B2 | 11/2014 | Jones et al. |
| 8,888,827 | B2 | 11/2014 | Harper et al. |
| 8,926,671 | B2 | 1/2015 | Biedermann et al. |
| 8,951,290 | B2 | 2/2015 | Hammer et al. |
| 8,986,349 | B1 | 3/2015 | German et al. |
| 8,998,959 | B2 | 4/2015 | Jackson et al. |
| 9,044,272 | B2 | 6/2015 | Shaffrey et al. |
| 9,060,814 | B2 | 6/2015 | Doubler et al. |
| 9,078,705 | B2 | 7/2015 | Matthis et al. |
| 9,119,674 | B2 | 9/2015 | Matthis et al. |
| 9,155,567 | B2 | 10/2015 | Auerbach et al. |
| 9,168,069 | B2 | 10/2015 | Jackson et al. |
| 9,198,695 | B2 | 12/2015 | Shluzas et al. |
| 9,254,150 | B2 | 2/2016 | Biedermann et al. |
| 9,259,247 | B2 | 2/2016 | Chandanson et al. |
| 9,358,047 | B2 | 6/2016 | Mishra et al. |
| 9,439,680 | B2 | 9/2016 | Biedermann et al. |
| 9,480,517 | B2 | 11/2016 | Jackson et al. |
| 9,486,246 | B2 | 11/2016 | Biedermann et al. |
| 9,492,204 | B2 | 11/2016 | Biedermann et al. |
| 9,526,529 | B2 | 12/2016 | Charvet |
| 9,566,092 | B2 | 2/2017 | Jackson et al. |
| 9,572,599 | B1 | 2/2017 | Casey et al. |
| 9,572,600 | B2 | 2/2017 | Biedermann et al. |
| 9,603,627 | B2 | 3/2017 | Krüger |
| 9,615,858 | B2 | 4/2017 | Doubler et al. |
| 9,649,134 | B2 | 5/2017 | Hannen |
| 9,655,652 | B2 | 5/2017 | Biedermann et al. |
| 9,707,013 | B2 | 7/2017 | Rezach et al. |
| 9,724,145 | B2 | 8/2017 | Spratt et al. |
| 9,763,702 | B2 | 9/2017 | Schlaepfer et al. |
| 9,775,660 | B2 | 10/2017 | Spratt et al. |
| 9,907,574 | B2 | 3/2018 | Jackson et al. |
| 9,918,745 | B2 | 3/2018 | Jackson et al. |
| 9,924,975 | B2 | 3/2018 | Jackson et al. |
| 9,980,753 | B2 | 5/2018 | Jackson et al. |
| 10,028,770 | B2 | 7/2018 | Rezach et al. |
| 10,039,572 | B2 | 8/2018 | Harris et al. |
| 10,052,136 | B2 | 8/2018 | Nelson |
| 10,058,354 | B2 | 8/2018 | Jackson et al. |
| 10,064,657 | B2 | 9/2018 | Spitler |
| 10,064,658 | B2 | 9/2018 | Jackson et al. |
| 10,117,680 | B2 | 11/2018 | Trautwein et al. |
| 10,130,396 | B2 | 11/2018 | Vedula et al. |
| 10,154,859 | B2 | 12/2018 | Keyer et al. |
| 10,172,647 | B2 | 1/2019 | Elsbury |
| 10,188,432 | B2 | 1/2019 | Jackson et al. |
| 10,285,738 | B1 | 5/2019 | Doubler et al. |
| 10,335,203 | B2 | 7/2019 | Fiechter et al. |
| 10,335,204 | B2 | 7/2019 | Matthis et al. |
| 10,363,070 | B2 | 7/2019 | Jackson et al. |
| 10,463,402 | B2 | 11/2019 | Biester et al. |
| 10,485,594 | B2 | 11/2019 | Toon et al. |
| 10,507,043 | B1 | 12/2019 | Gladieux |
| 10,517,645 | B2 | 12/2019 | van der Pol |
| 10,524,840 | B2 | 1/2020 | Purcell et al. |
| 10,537,366 | B2 | 1/2020 | Purcell et al. |
| 10,595,905 | B2 | 3/2020 | Purcell et al. |

(56) References Cited

U.S. PATENT DOCUMENTS

| | | |
|---|---|---|
| 10,595,906 B2 | 3/2020 | Purcell et al. |
| 10,695,100 B2 | 6/2020 | May et al. |
| 10,792,074 B2 | 10/2020 | Jackson |
| 10,898,233 B2 | 1/2021 | Jackson et al. |
| 10,966,760 B2 | 4/2021 | Armstrong et al. |
| 11,234,738 B2 | 2/2022 | Jackson et al. |
| 11,234,745 B2 | 2/2022 | Jackson |
| 11,304,732 B2 | 4/2022 | Mueller et al. |
| 11,571,244 B2 | 2/2023 | Loftis et al. |
| 2003/0149431 A1 | 8/2003 | Varieur |
| 2004/0102781 A1 | 5/2004 | Jeon |
| 2004/0186473 A1 | 9/2004 | Cournoyer et al. |
| 2004/0260283 A1 | 12/2004 | Wu et al. |
| 2005/0203516 A1 | 9/2005 | Biedermann et al. |
| 2006/0058788 A1 | 3/2006 | Hammer et al. |
| 2006/0161152 A1 | 7/2006 | Ensign et al. |
| 2006/0200131 A1 | 9/2006 | Chao et al. |
| 2006/0217716 A1 | 9/2006 | Baker et al. |
| 2007/0118123 A1 | 5/2007 | Strausbaugh et al. |
| 2007/0270807 A1 | 11/2007 | Armstrong et al. |
| 2007/0270813 A1 | 11/2007 | Garamszegi |
| 2008/0147129 A1 | 6/2008 | Biedermann et al. |
| 2008/0177260 A1* | 7/2008 | Mckinley ............ A61B 17/7038 606/60 |
| 2009/0204155 A1 | 8/2009 | Aschmann |
| 2010/0010540 A1 | 1/2010 | Park |
| 2010/0152787 A1 | 6/2010 | Walsh et al. |
| 2010/0331887 A1 | 12/2010 | Jackson et al. |
| 2011/0040338 A1 | 2/2011 | Jackson |
| 2011/0270321 A1 | 11/2011 | Prevost et al. |
| 2012/0016425 A1* | 1/2012 | Shaffrey ............ A61B 17/7002 606/305 |
| 2012/0310284 A1 | 12/2012 | Gerchow |
| 2013/0103098 A1 | 4/2013 | Jackson et al. |
| 2013/0144346 A1 | 6/2013 | Jackson et al. |
| 2013/0218213 A1 | 8/2013 | Lemoine |
| 2014/0025119 A1 | 1/2014 | Biedermann et al. |
| 2016/0317206 A1 | 11/2016 | Rezach et al. |
| 2017/0333085 A1* | 11/2017 | Jackson ............ A61B 17/7038 |

FOREIGN PATENT DOCUMENTS

| | | | |
|---|---|---|---|
| WO | WO 2009/055747 | 4/2009 | |
| WO | WO-2016065033 A1 * | 4/2016 | ........... A61B 17/702 |
| WO | WO 2020/056385 | 3/2020 | |
| WO | WO 2021/127251 | 6/2021 | |

* cited by examiner

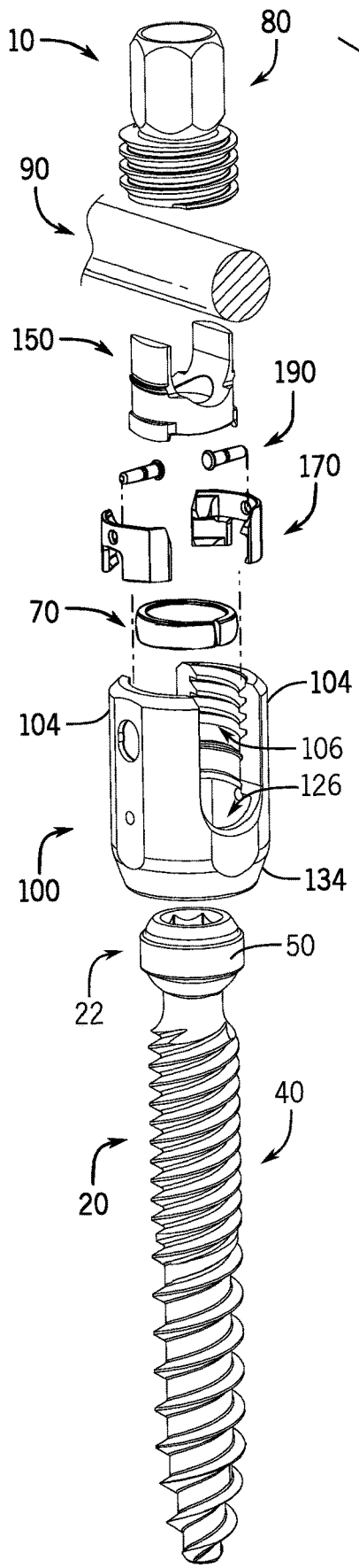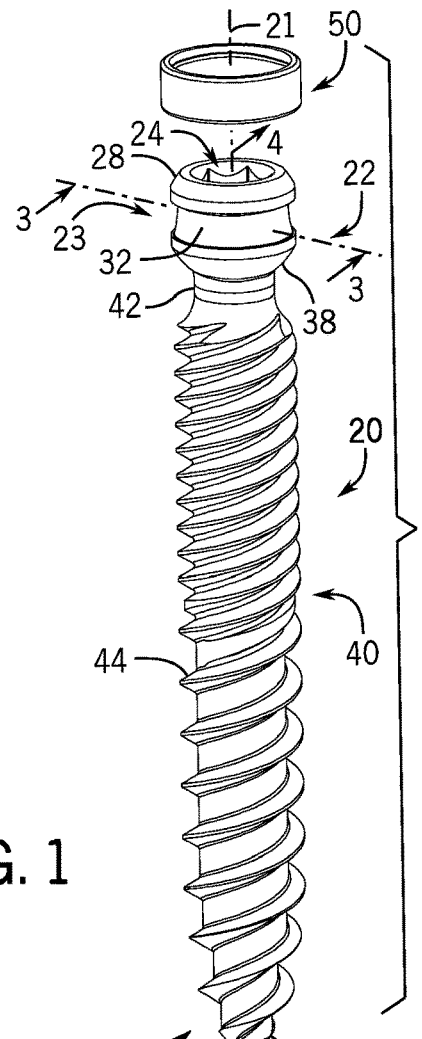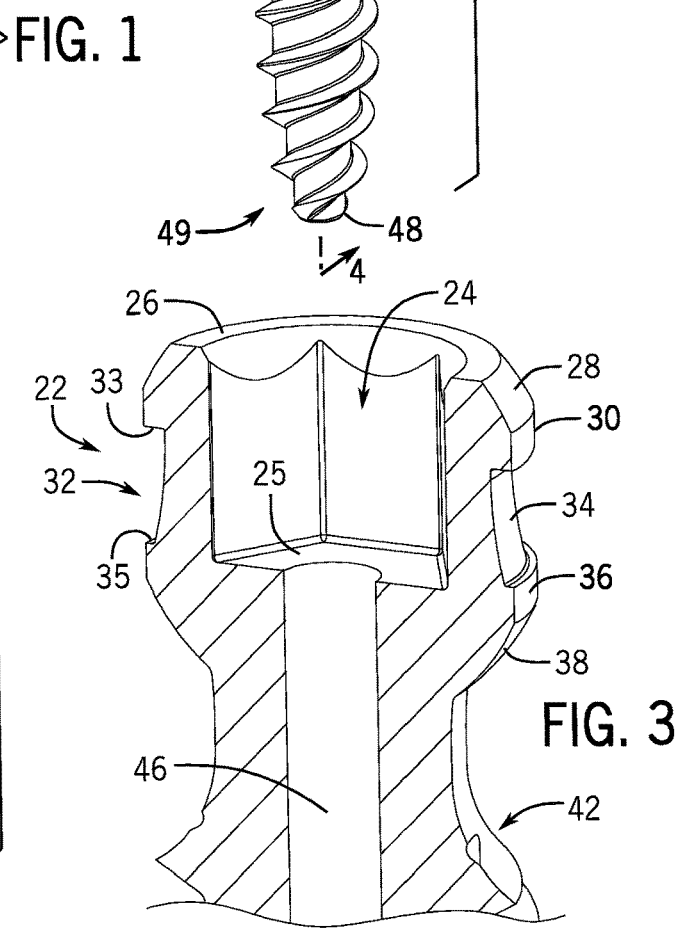

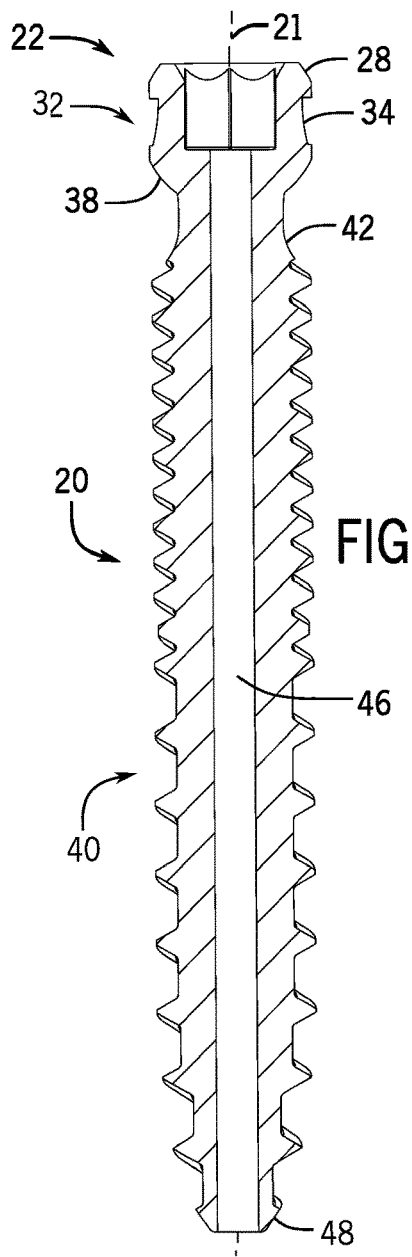
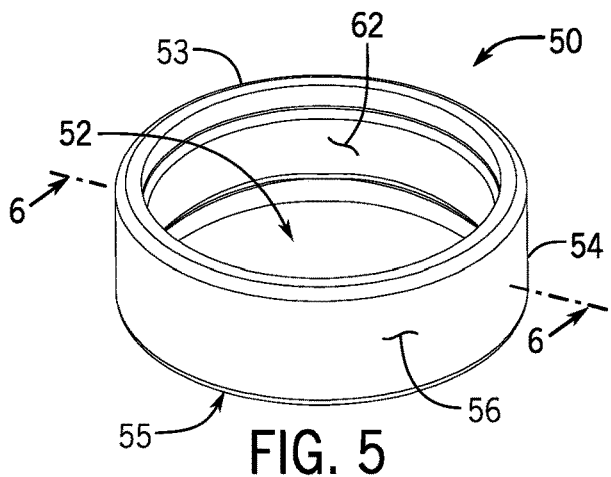
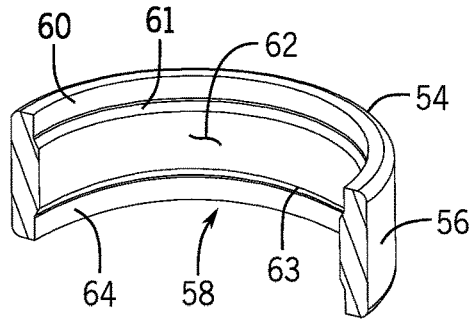
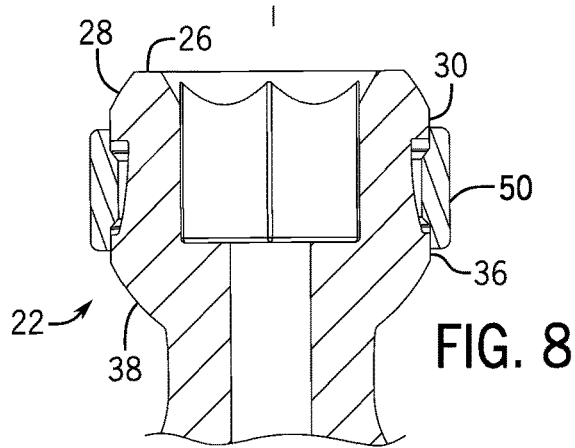
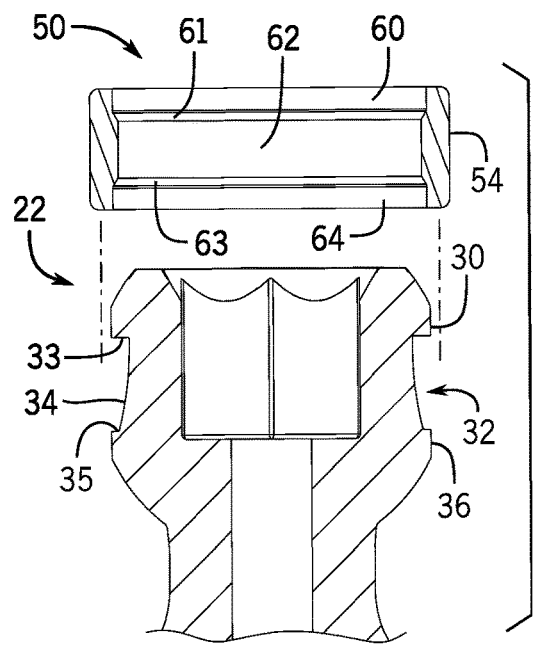
FIG. 4
FIG. 5
FIG. 6
FIG. 7
FIG. 8

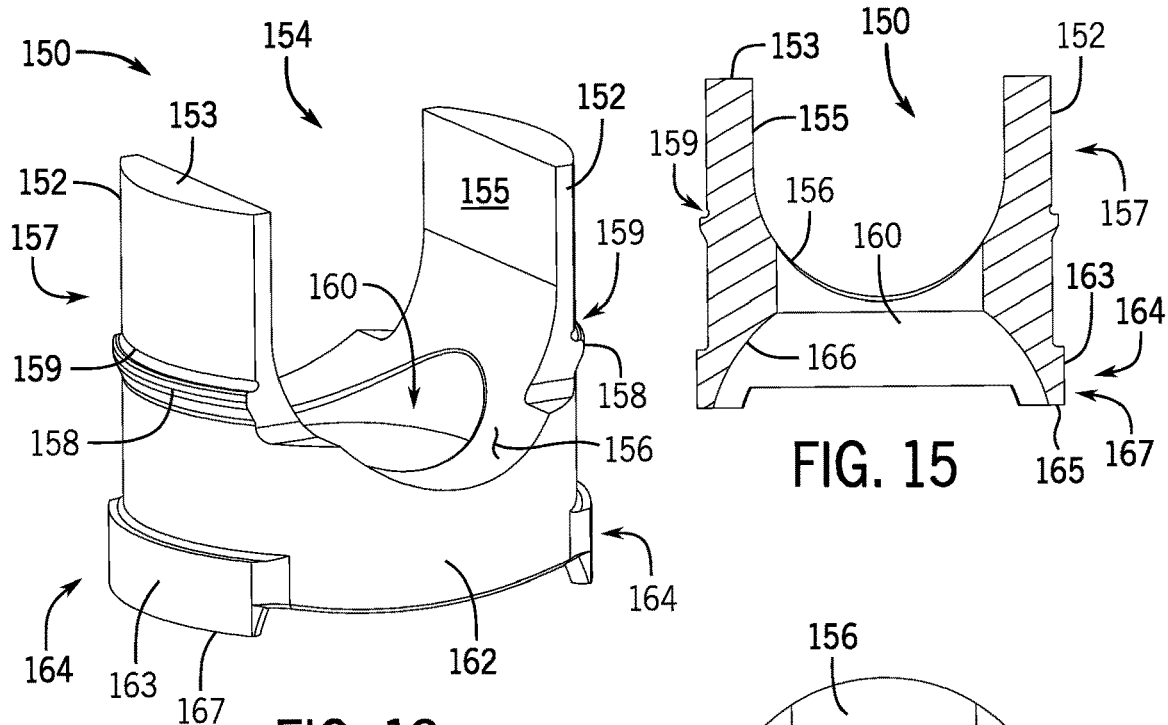
FIG. 13
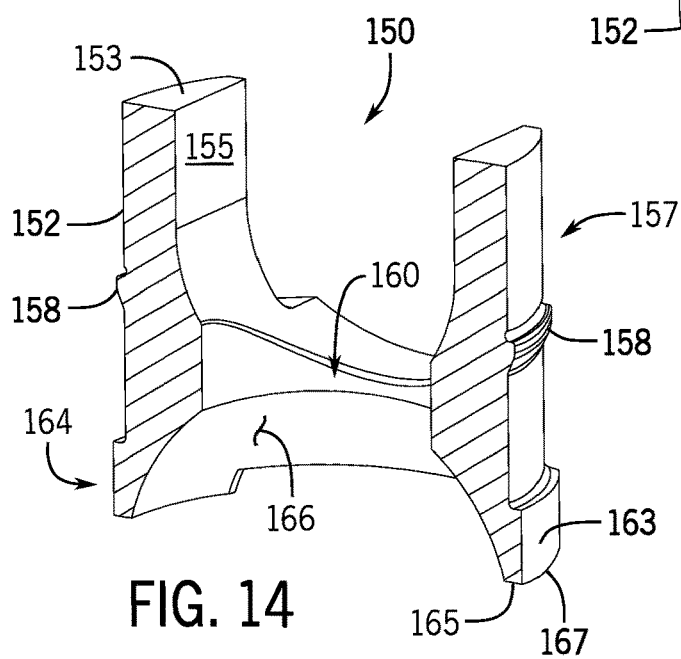
FIG. 14
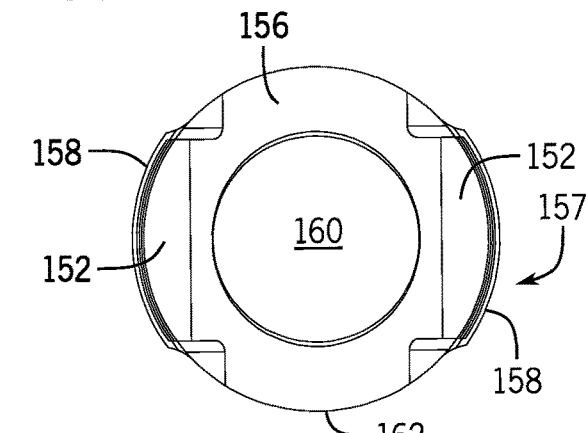
FIG. 15
FIG. 16
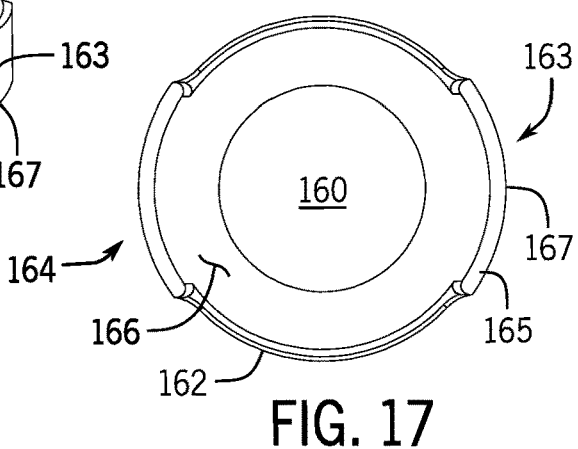
FIG. 17

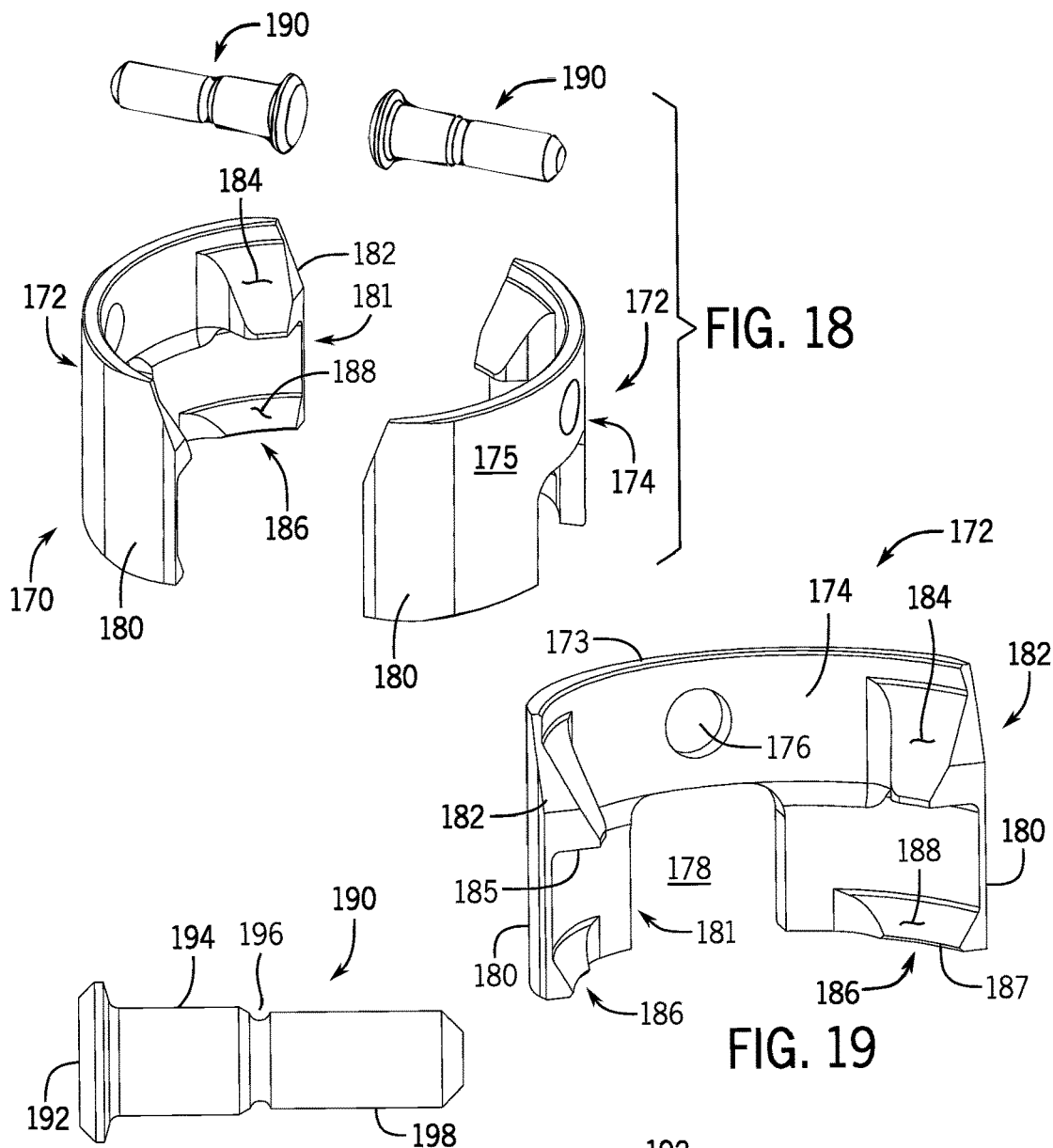
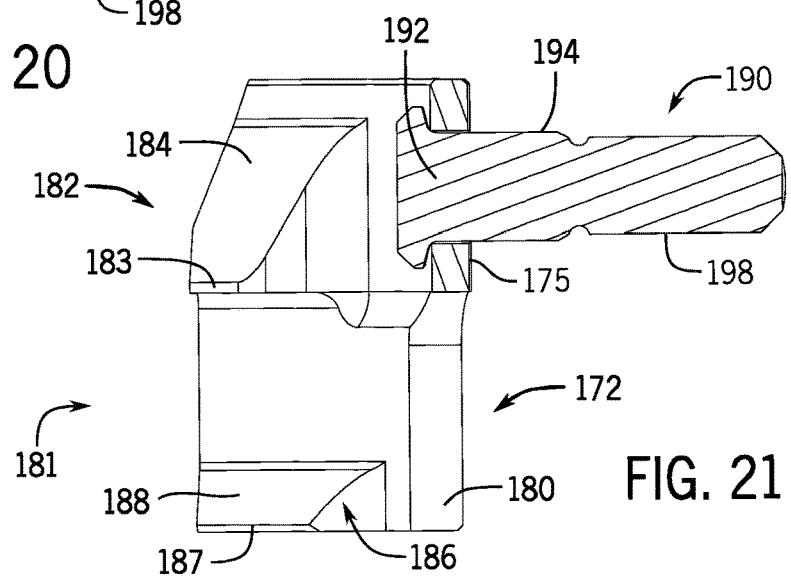

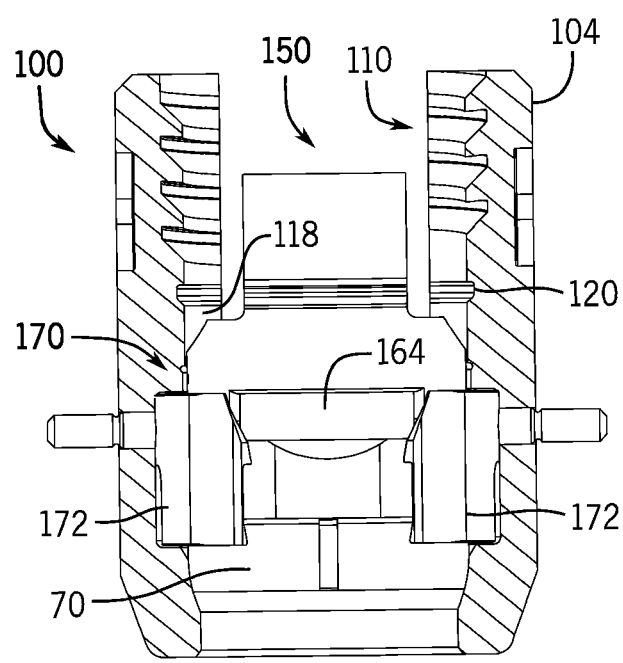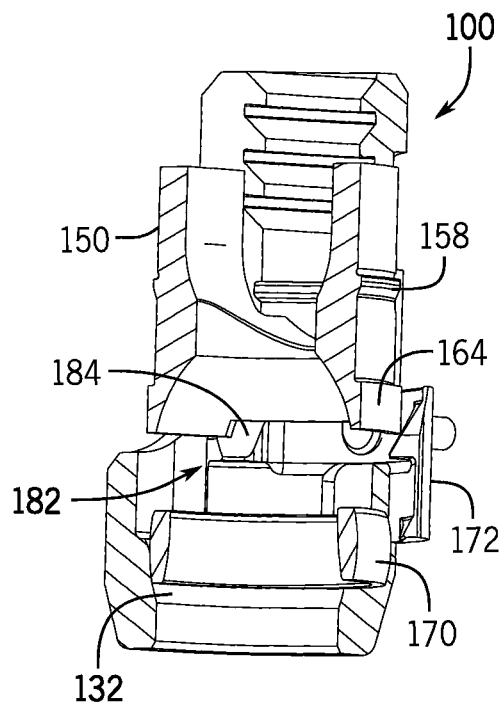
FIG. 37
FIG. 38
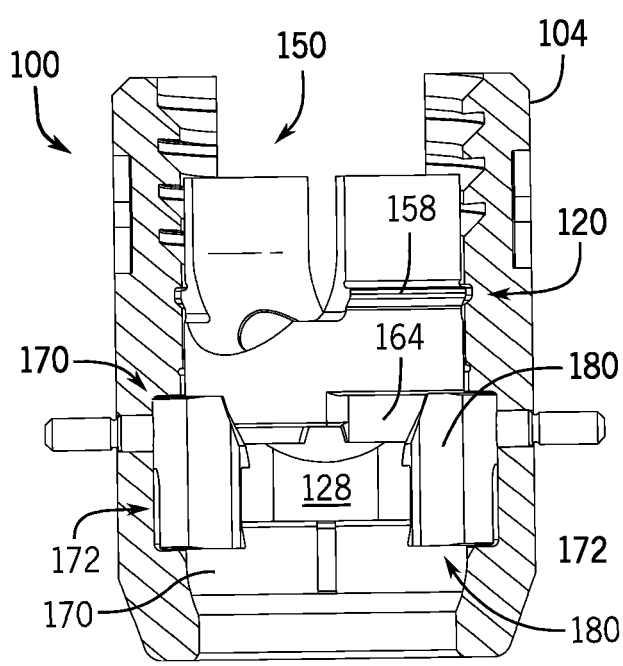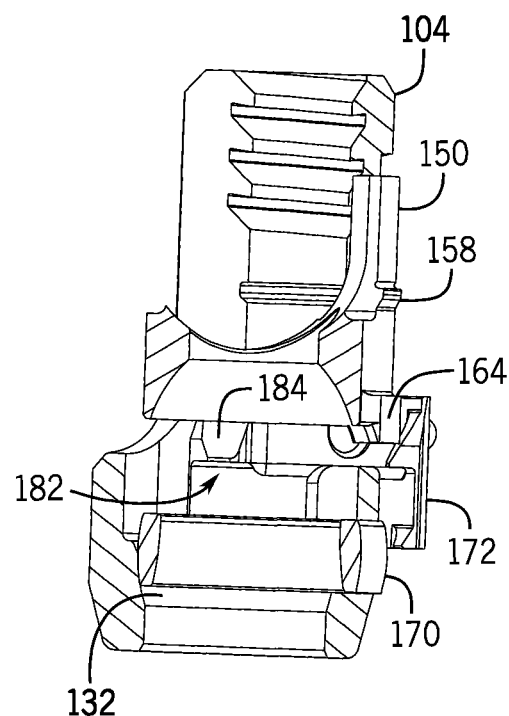
FIG. 39
FIG. 40

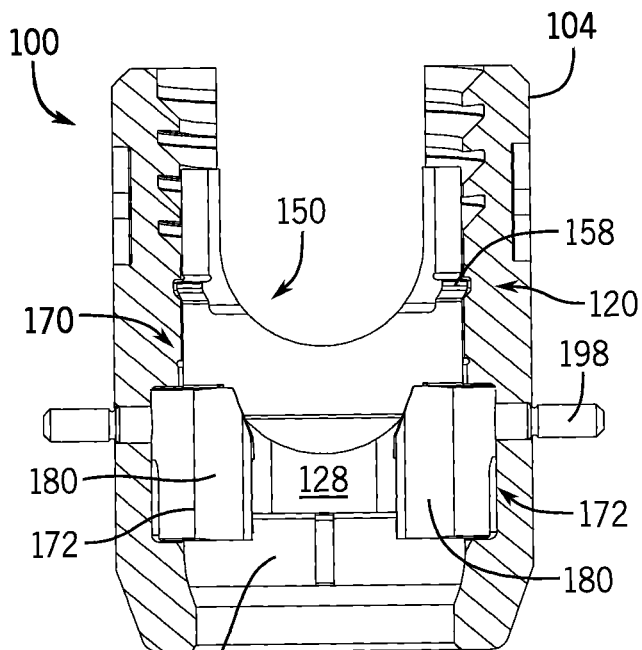 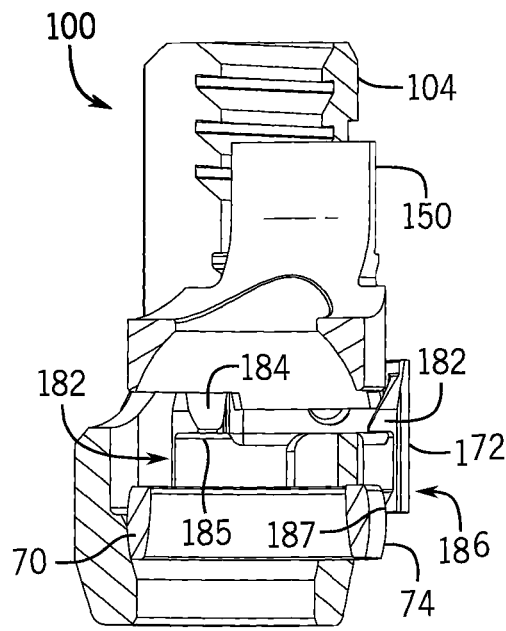
FIG. 41 FIG. 42
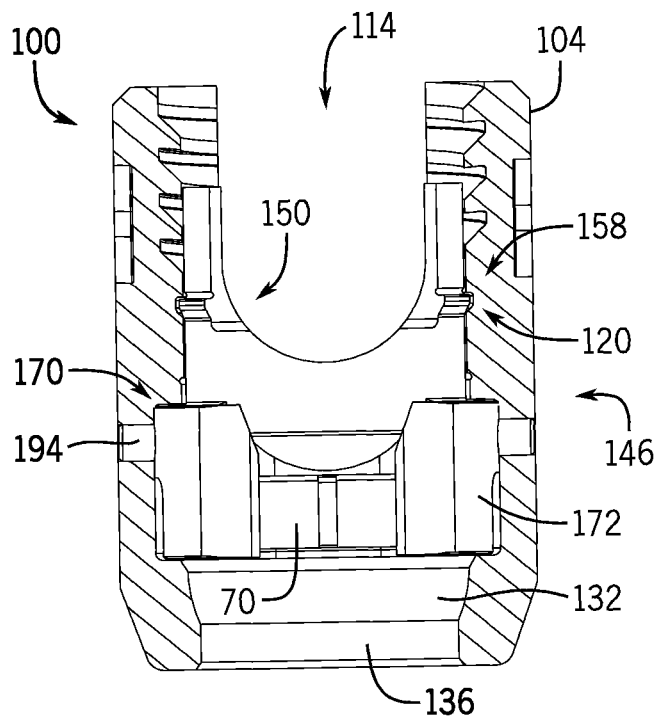 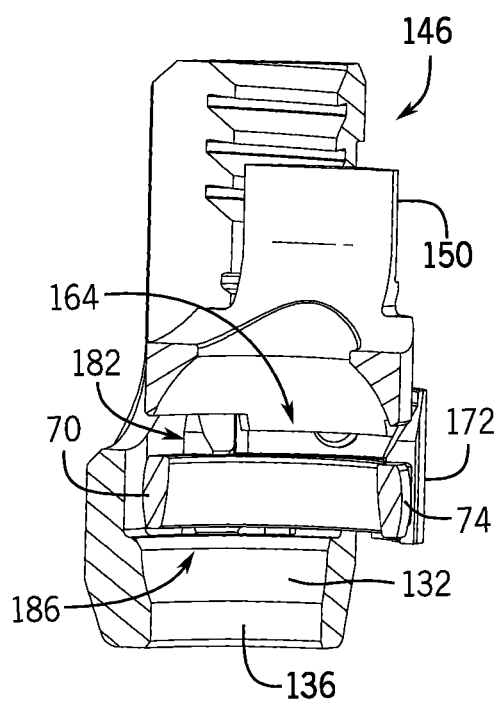
FIG. 43 FIG. 44

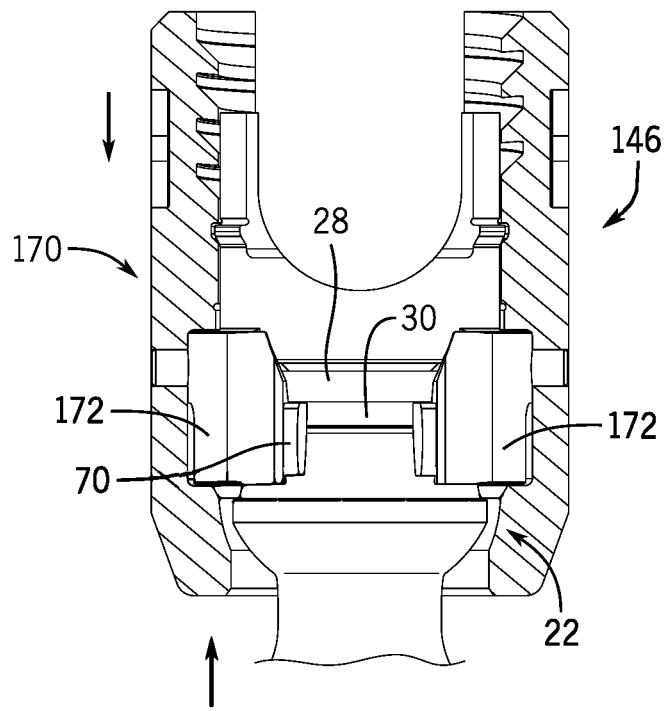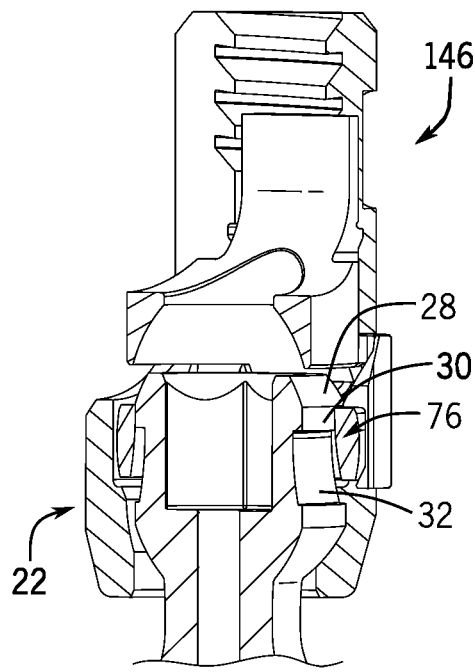
FIG. 51  FIG. 52
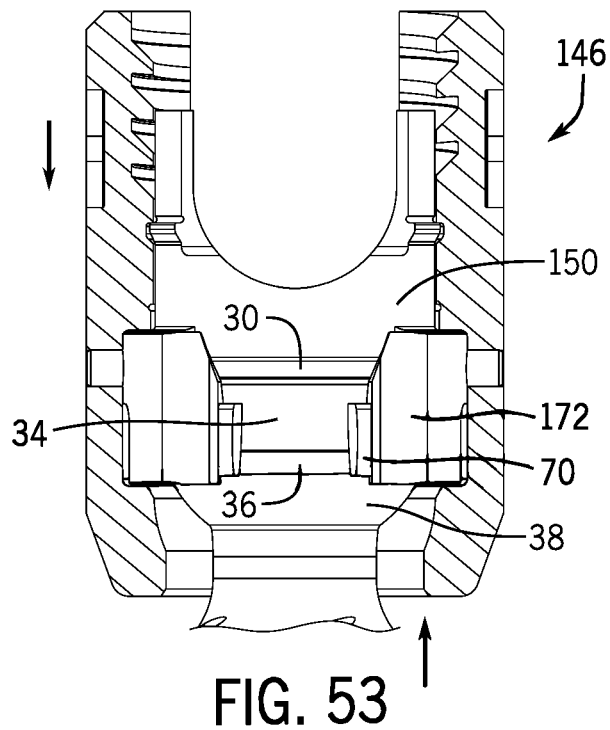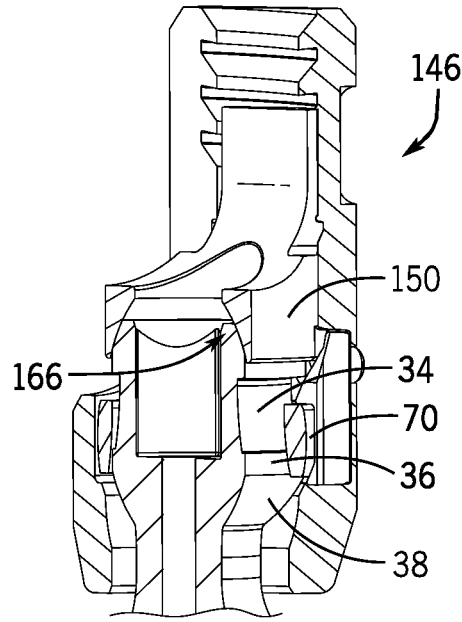
FIG. 53  FIG. 54

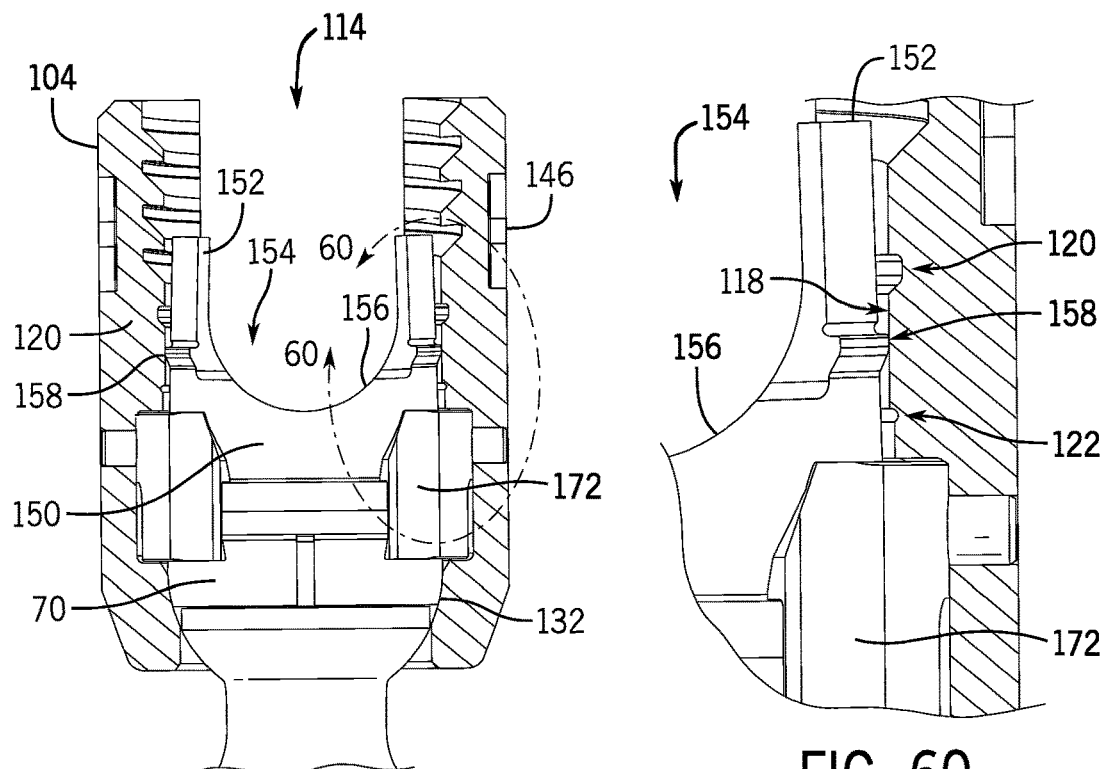
FIG. 59
FIG. 60
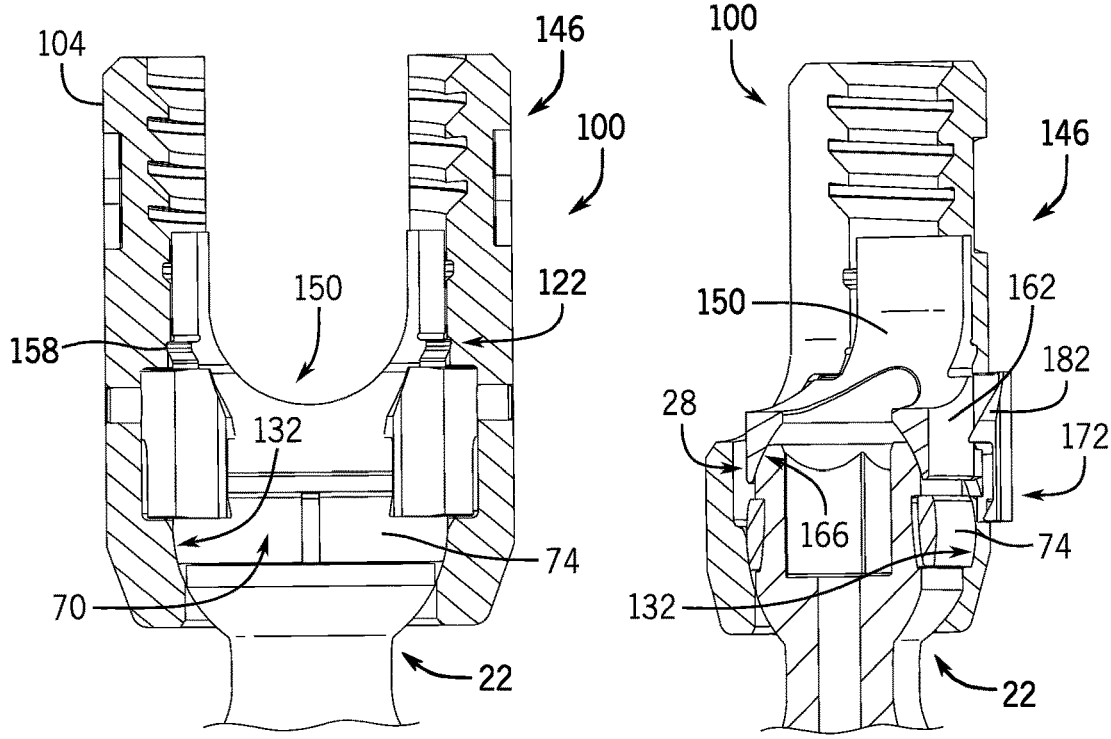
FIG. 61
FIG. 62

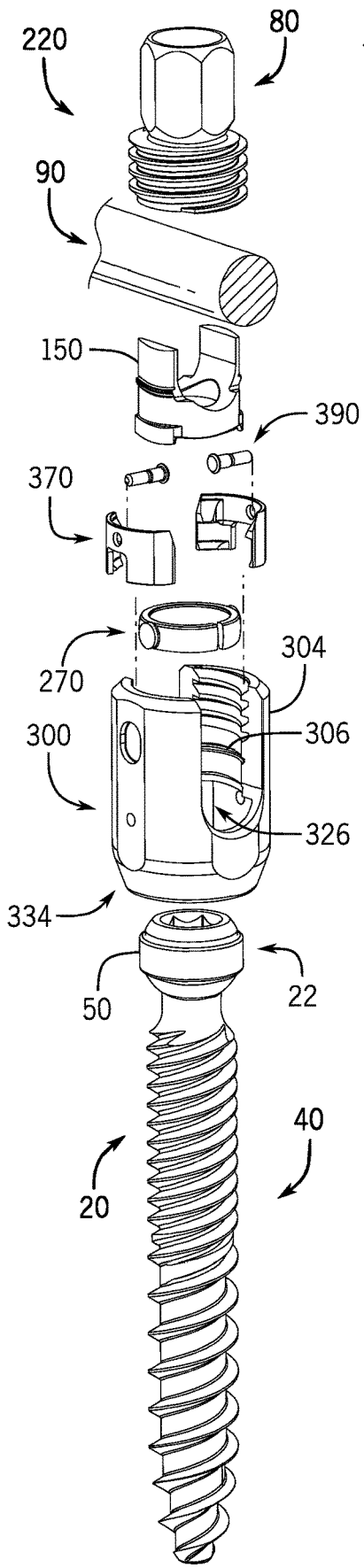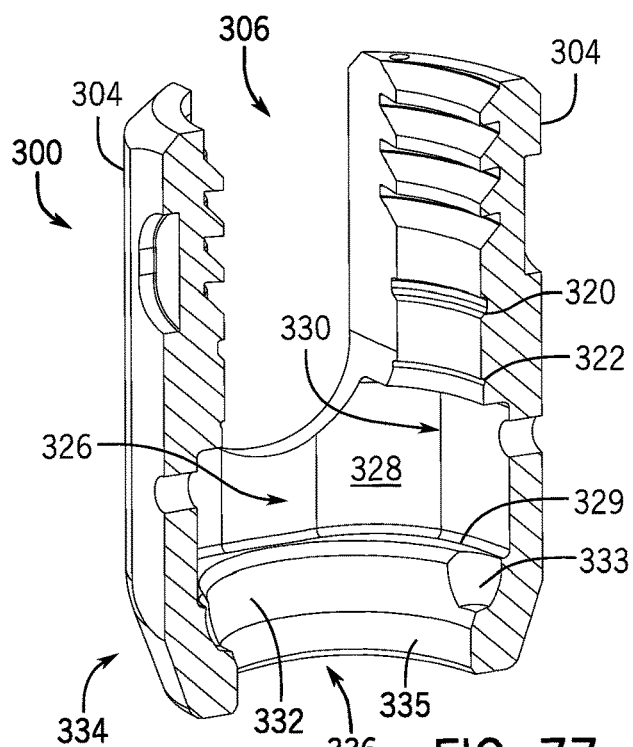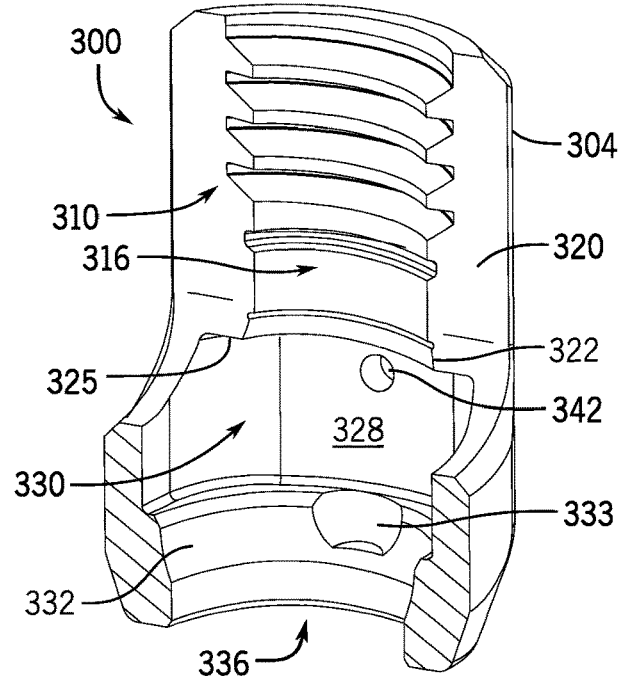
FIG. 76
FIG. 77
FIG. 78

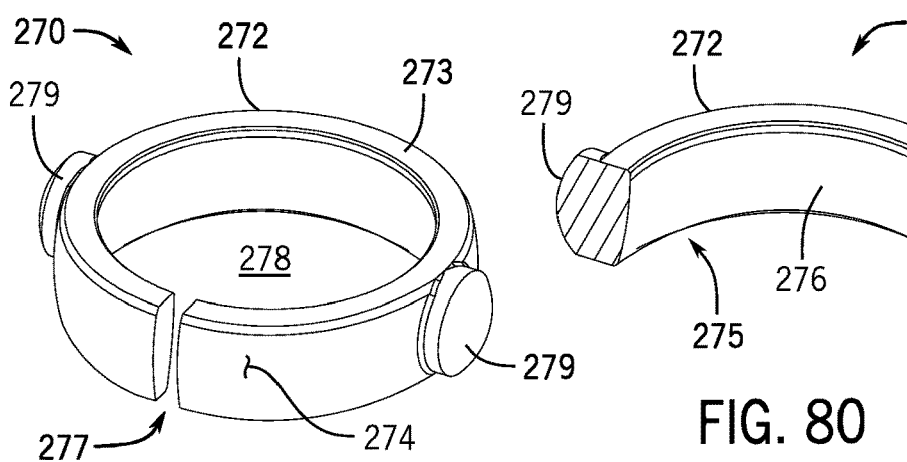
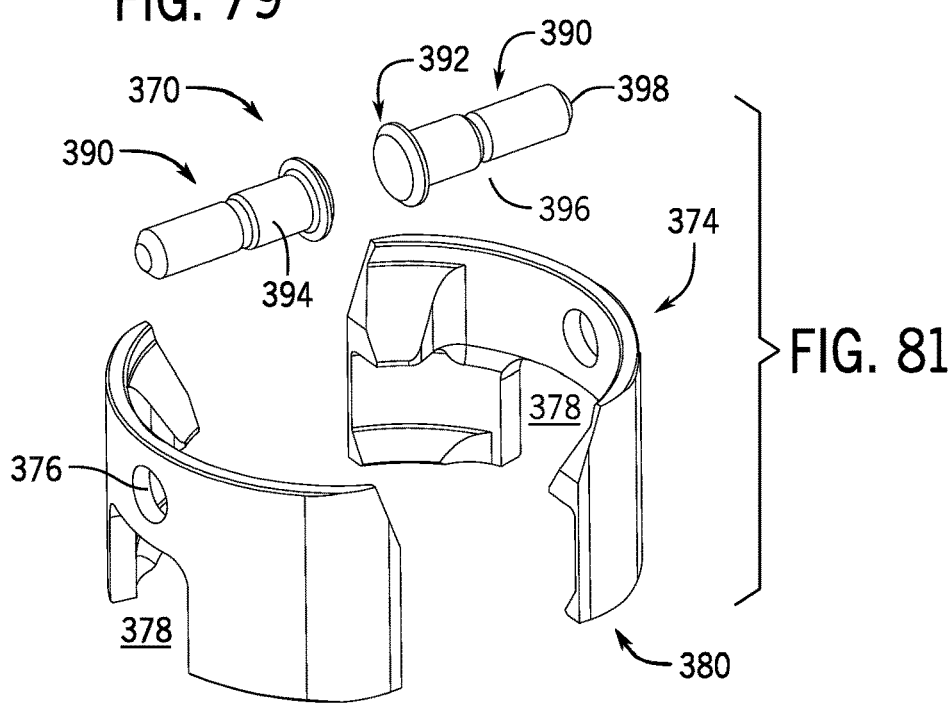
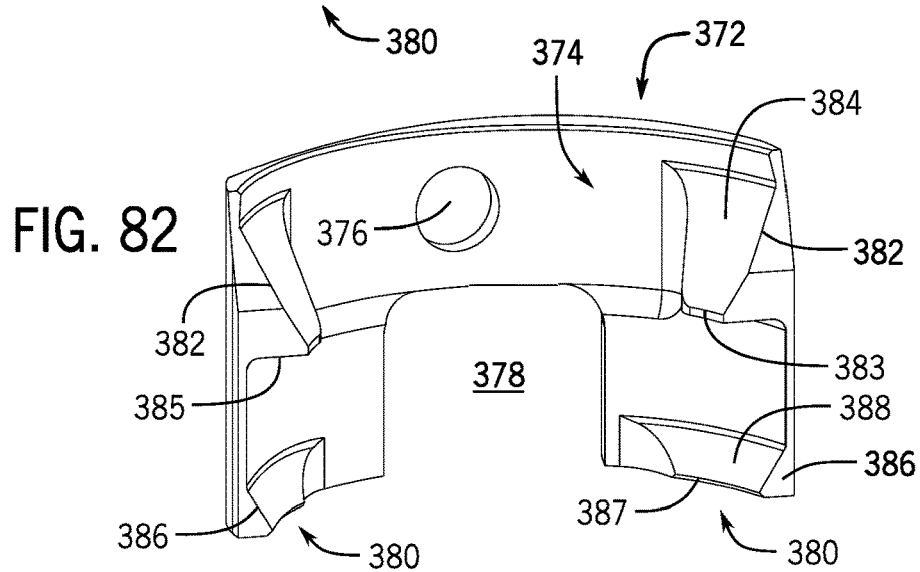

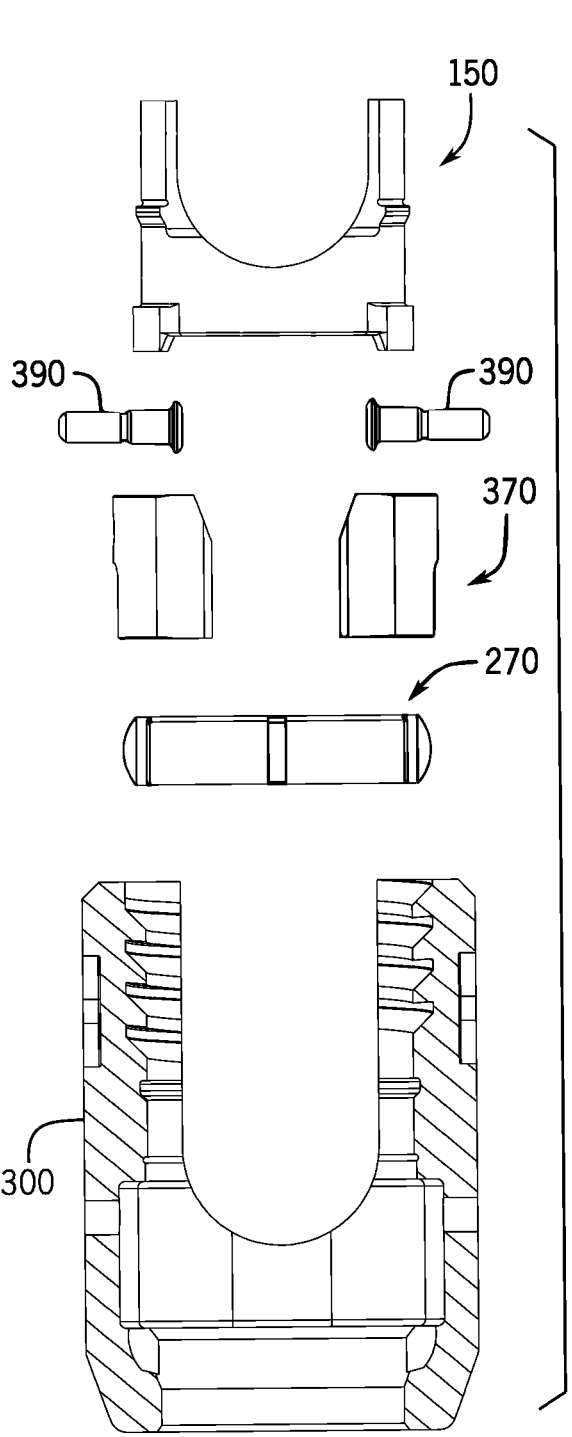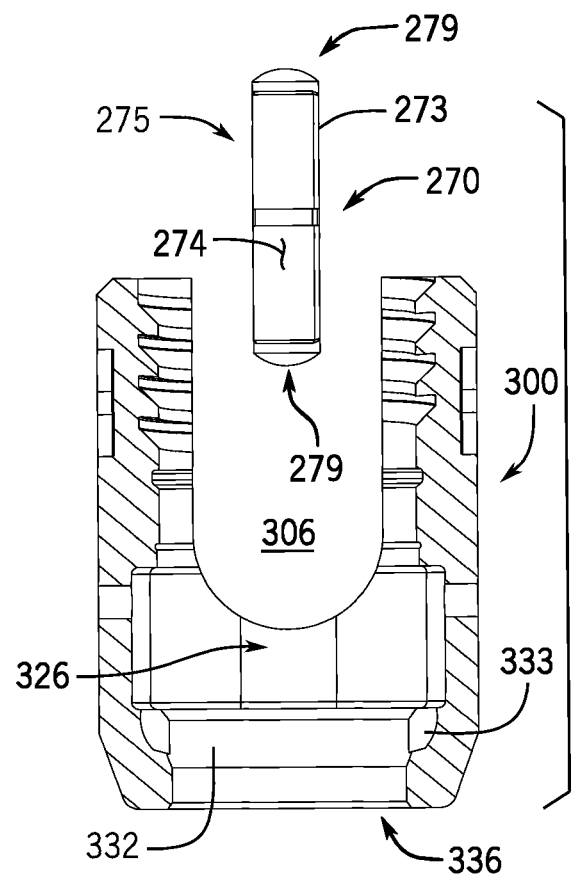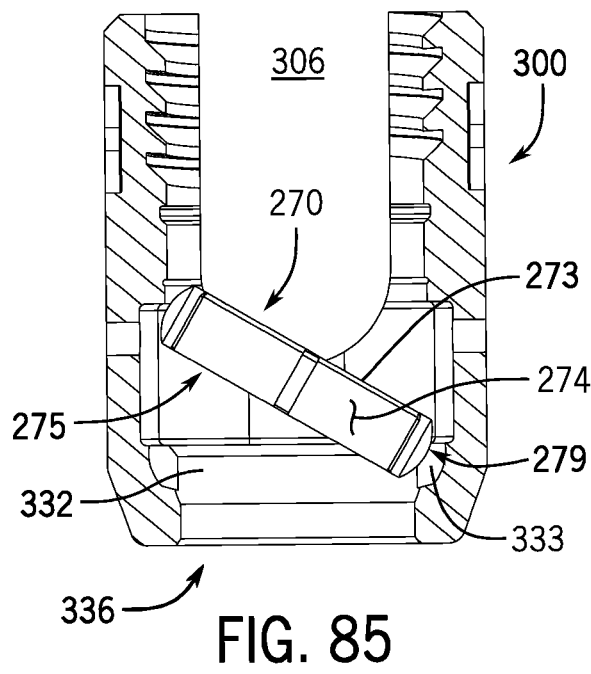
FIG. 83
FIG. 84
FIG. 85

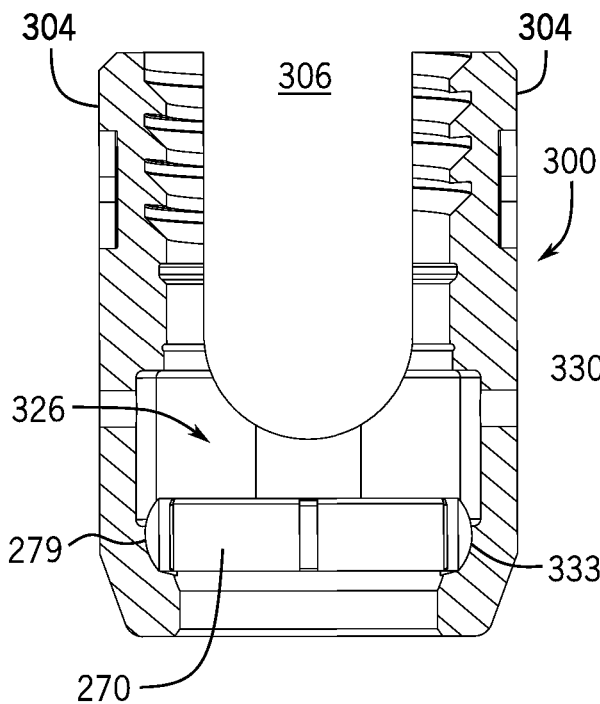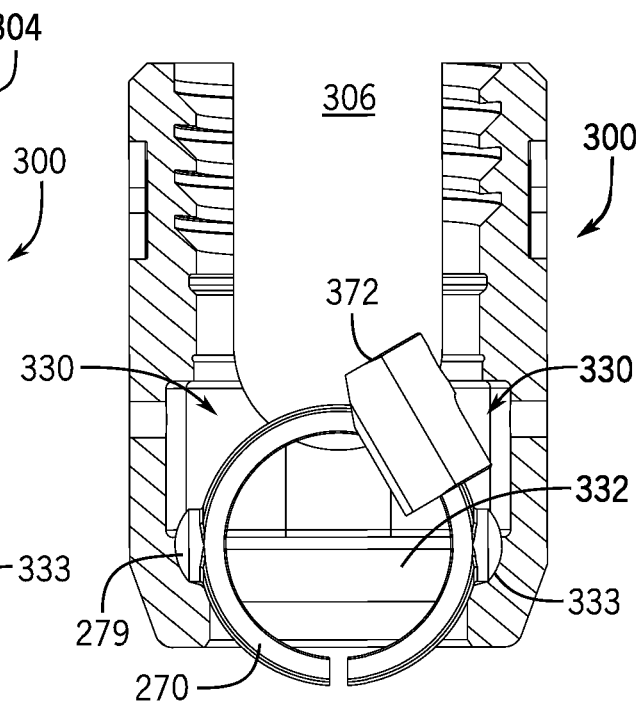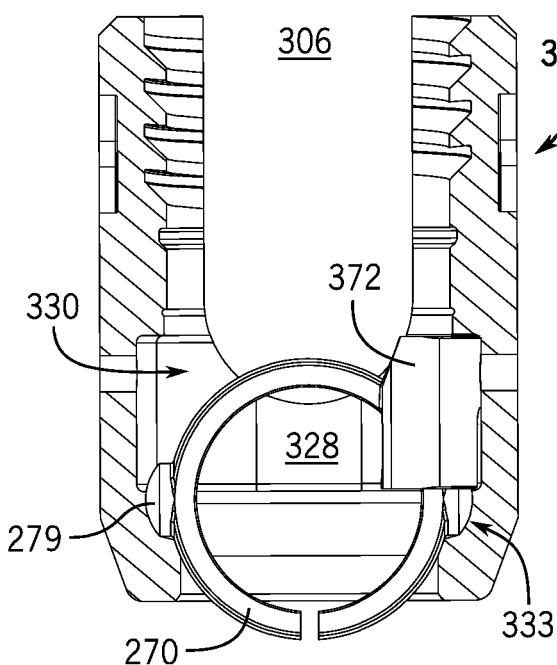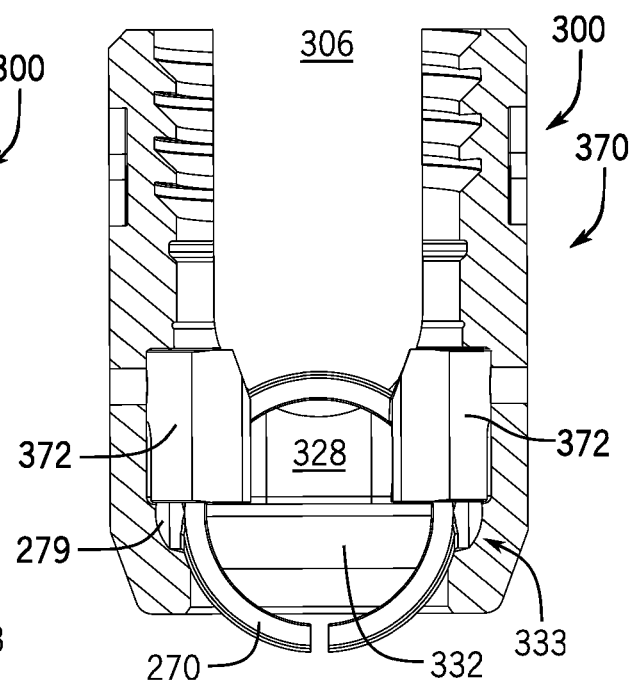

PIVOTAL BONE ANCHOR SYSTEM WITH MODULAR RECEIVER SUB-ASSEMBLIES AND UNIVERSAL BONE ANCHORS

CROSS-REFERENCE TO RELATED APPLICATIONS

This application is a continuation of U.S. application Ser. No. 17/275,923, filed Mar. 12, 2021, now U.S. Pat. No. 11,596,449, which is a U.S. National Phase Application under 35 U.S.C. § 371 of International Application No. PCT/US2019/051189, filed Sep. 13, 2019, which claims the benefit of U.S. Provisional Application No. 62/731,023, filed Sep. 13, 2018, and U.S. Provisional Application No. 62/810,361, filed Feb. 25, 2019, each of which is incorporated by reference in its entirety herein, and for all purposes.

FIELD OF THE INVENTION

The present invention generally relates to pivotal bone anchor assemblies for use in bone surgery, particularly spinal surgery.

BACKGROUND

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke defining slot or channel having different shapes, such as U-shaped and square shaped, for example, to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as an elongate rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, pivotal or polyaxial bone screws are commonly preferred. Open-ended polyaxial bone screws typically allow for pivoting and rotation of the separate receiver about the shank in one or more planes until a desired rotational position of the receiver is achieved by fixing such position relative to the shank during a final stage of a medical procedure when an elongate rod or other longitudinal connecting member is inserted into the receiver, followed by a locking set screw or other closure.

SUMMARY

Briefly described, one embodiment of the present disclosure comprises a pivotal bone anchor system for securing an elongate rod to patient bone. The pivotal bone anchor system includes a plurality of bone anchors, with each bone anchor having a capture portion having a rounded shape and an anchor portion extending downward from the capture portion for attachment to the bone. A horizontal capture recess extends into and circumferentially around a midsection of each rounded capture portion.

The pivotal bone anchor system also includes one or more multi-planar receiver sub-assemblies, with each multi-planar sub-assembly including a multi-planar receiver having a upper channel portion configured to receive the elongate rod and a lower base portion defining an internal cavity with a substantially continuous circumferential partial spherical multi-planar seating surface proximate a bottom opening. Each multi-planar sub-assembly also includes a multi-planar retainer with a partial spherical outer surface configured for multi-planar motion upon engagement with the multi-planar seating surface, and an inner surface configured to snap into the bone anchor capture recess to capture the bone anchor within the multi-planar receiver cavity, and wherein the bone anchor is axially rotatable with respect to the retainer after capture.

The pivotal bone anchor system further includes one or more uni-planar receiver sub-assemblies, with each uni-planar sub-assembly including a uni-planar receiver having a upper channel portion configured to receive the elongate rod and a lower base portion defining an internal cavity with a non-continuous circumferential partial spherical uni-planar seating surface with opposing pockets proximate a bottom opening. Each uni-planar sub-assembly also includes a uni-planar retainer with a partial spherical outer surface having opposing pegs projecting outward therefrom, and which is configured for uni-planar motion upon engagement with the uni-planar seating surface and opposing pockets of the uni-planar receiver, and an inner surface configured to snap into the bone anchor capture recess to capture the bone anchor within the uni-planar receiver cavity, and wherein the bone anchor is axially rotatable with respect to the retainer after capture.

Furthermore, the capture portions of the plurality of bone anchors are configured for capture by either a multi-planar receiver sub-assembly or a uni-planar receiver sub-assembly without further modification or adjustment to the bone anchor capture portion.

The invention will be better understood upon review of the detailed description set forth below taken in conjunction with the accompanying drawing figures, which are briefly described as follows.

BRIEF DESCRIPTION OF THE DRAWINGS

FIG. 1 is an exploded perspective view of a multi-planar pivotal bone anchor assembly, in accordance with a representative embodiment of the present disclosure.

FIG. 2 is an exploded perspective view of the bone anchor and a capture recess protection sleeve of the multi-planar pivotal bone anchor assembly of FIG. 1.

FIG. 3 is a cross-sectional perspective view of the shank head of the bone anchor of FIG. 2.

FIG. 4 is a cross-sectional view of the bone anchor of FIG. 2.

FIG. 5 is a perspective view of the capture recess protection sleeve of FIG. 2.

FIG. 6 is a cross-sectional perspective view of the capture recess protection sleeve of FIG. 2

FIG. 7 is a cross-sectional side view of the shank head and capture recess protection sleeve of FIG. 2 prior to assembly.

FIG. 8 is a cross-sectional side view of the shank head and capture recess protection sleeve of FIG. 2 after assembly.

FIG. 13 is a perspective view of the pressure insert of the multi-planar pivotal bone anchor assembly of FIG. 1.

FIG. 14 is a cross-sectional perspective view of the pressure insert of FIG. 13.

FIG. 15 is a cross-sectional side view of the pressure insert of FIG. 13.

FIG. 16 is a top view of the pressure insert of FIG. 13.

FIG. 17 is a bottom view of the pressure insert of FIG. 13.

FIG. 18 is an exploded perspective view of the multi-planar two-piece positioner and positioner pins of the multi-planar pivotal bone anchor assembly of FIG. 1.

FIG. 19 is a perspective view of a multi-planar positioner piece of FIG. 18.

FIG. 20 is a side view of a positioner pin of FIG. 18.

FIG. 21 is a cross-sectional side view of a multi-planar positioner piece of FIG. 18 assembled together with a positioner pin.

FIG. 37 is another partially cut-away side view of the multi-planar receiver with the installed multi-planar retainer, multi-planar positioner pieces, and positioner pins, and with the pressure insert being installed therein.

FIG. 38 is a sectioned perspective view of the multi-planar receiver, multi-planar retainer, multi-planar positioner pieces, positioner pins, and pressure insert of FIG. 37.

FIG. 39 is another partially cut-away side view of the multi-planar receiver with the installed multi-planar retainer, multi-planar positioner pieces, and positioner pins, and with the pressure insert being rotated therein.

FIG. 40 is a sectioned perspective view of the multi-planar receiver, multi-planar retainer, multi-planar positioner pieces, positioner pins, and pressure insert of FIG. 39.

FIG. 41 is another partially cut-away side view of the multi-planar receiver with the installed multi-planar retainer, multi-planar positioner pieces, and positioner pins, and with the pressure insert being fully installed therein.

FIG. 42 is a sectioned perspective view of the multi-planar receiver, multi-planar retainer, multi-planar positioner pieces, positioner pins, and pressure insert of FIG. 41.

FIG. 43 is a partially cut-away side view of the multi-planar receiver together with the installed and positioned multi-planar retainer, multi-planar positioner pieces, positioner pins, and pressure insert forming a pre-assembled multi-planar receiver sub-assembly.

FIG. 44 is a sectioned perspective view of the pre-assembled multi-planar receiver sub-assembly of FIG. 43.

FIG. 51 is a partially cut-away side view of the multi-planar receiver sub-assembly moving further downward until the universal shank head causes maximum expansion of the constrained multi-planar retainer.

FIG. 52 is a sectioned perspective view of the multi-planar receiver sub-assembly and universal shank head of FIG. 51.

FIG. 53 is a partially cut-away side view of the multi-planar receiver sub-assembly moving further downward until the universal shank head reaches maximum push through within the receiver cavity.

FIG. 54 is a sectioned perspective view of the multi-planar receiver sub-assembly and universal shank head of FIG. 53.

FIG. 59 is a partially cut-away side view of the multi-planar receiver sub-assembly and coupled universal shank head, with the pressure insert in a partially deployed position.

FIG. 60 is a sectioned perspective view of the multi-planar receiver sub-assembly and universal shank head of FIG. 59.

FIG. 61 is a partially cut-away side view of the multi-planar receiver sub-assembly and coupled universal shank head, with the pressure insert in a fully deployed friction fit position.

FIG. 62 is a sectioned perspective view of the multi-planar receiver sub-assembly and universal shank head of FIG. 61.

FIG. 76 is an exploded perspective view of a uni-planar pivotal bone anchor assembly, in accordance with another representative embodiment of the present disclosure.

FIG. 77 is a cross-sectional perspective view of the uni-planar receiver of the uni-planar pivotal bone anchor assembly of FIG. 76.

FIG. 78 is another cross-sectional perspective view of the uni-planar receiver of FIG. 77.

FIG. 79 is a perspective view of the uni-planar retainer of the uni-planar pivotal bone anchor assembly of FIG. 76.

FIG. 80 is a cross-sectional perspective view of the uni-planar retainer of FIG. 79.

FIG. 81 is an exploded perspective view of the uni-planar two-piece positioner and positioner pins of the uni-planar pivotal bone anchor assembly of FIG. 1.

FIG. 82 is a perspective view of a uni-planar positioner piece of FIG. 81.

FIG. 83 is an exploded side view of the components of the uni-planar receiver sub-assembly prior to their pre-assembly into a shipping configuration.

FIG. 84 is a partially cut-away side view of the uni-planar receiver of FIG. 83 with the uni-planar retainer being installed therein.

FIG. 85 is another partially cut-away side view of the uni-planar receiver of FIG. 83 with the uni-planar retainer being installed therein.

FIG. 86 is a partially cut-away side view of the uni-planar receiver of FIG. 83 with the uni-planar retainer installed therein.

FIG. 87 is a partially cut-away side view of the uni-planar receiver with the installed uni-planar retainer and with a uni-planar positioner piece being installed therein.

FIG. 88 is another partially cut-away side view of the uni-planar receiver with the installed uni-planar retainer and with the uni-planar positioner piece being installed therein.

FIG. 89 is a partially cut-away side view of the uni-planar receiver with the uni-planar retainer and both uni-planar positioner pieces installed therein.

FIG. 120 is a partially cut-away and sectioned perspective view of the uni-planar receiver sub-assembly and coupled universal shank head in a friction fit position, with the bone anchor being pivoted relative to the receiver.

FIG. 121 is another partially cut-away and sectioned perspective view of the uni-planar receiver sub-assembly and coupled universal shank head of FIG. 120.

FIG. 122 is a partially cut-away and sectioned perspective view of the uni-planar receiver sub-assembly and coupled universal shank head, and further with an elongate rod and closure, in a partially locked configuration with the bone anchor being pivoted relative to the receiver.

FIG. 123 is another partially cut-away and sectioned perspective view of the uni-planar receiver sub-assembly, coupled universal shank head, elongate rod, and closure of FIG. 122.

FIG. 124 is a partially cut-away and sectioned perspective view of the uni-planar receiver sub-assembly and coupled universal shank head with an elongate rod and closure in a fully locked configuration, thereby forming a completely assembled representative embodiment of a uni-planar pivotal bone anchor apparatus or system, with the bone anchor being pivoted relative to the receiver.

FIG. 125 is a perspective view of a pair of multi-planar pivotal bone anchor assemblies, each with housings configured for adjacent level connection, in accordance with another representative embodiment of the present disclosure.

FIG. 126 is another perspective view of the pair of multi-planar pivotal bone anchor assemblies of FIG. 125.

FIG. 127 is a perspective view of one of the multi-planar pivotal bone anchor assemblies of FIG. 125.

FIG. 128 is a partially cut-away perspective view of the multi-planar pivotal bone anchor assembly of FIG. 127.

FIG. 129 is another partially cut-away perspective view of the multi-planar pivotal bone anchor assembly of FIG. 127.

FIG. 130 is another partially cut-away perspective view of the multi-planar pivotal bone anchor assembly of FIG. 127.

FIG. 131 is a perspective view of a multi-planar pivotal bone anchor assembly with a housing configured for adjacent level connection, in accordance with another representative embodiment of the present disclosure.

Figure 131:
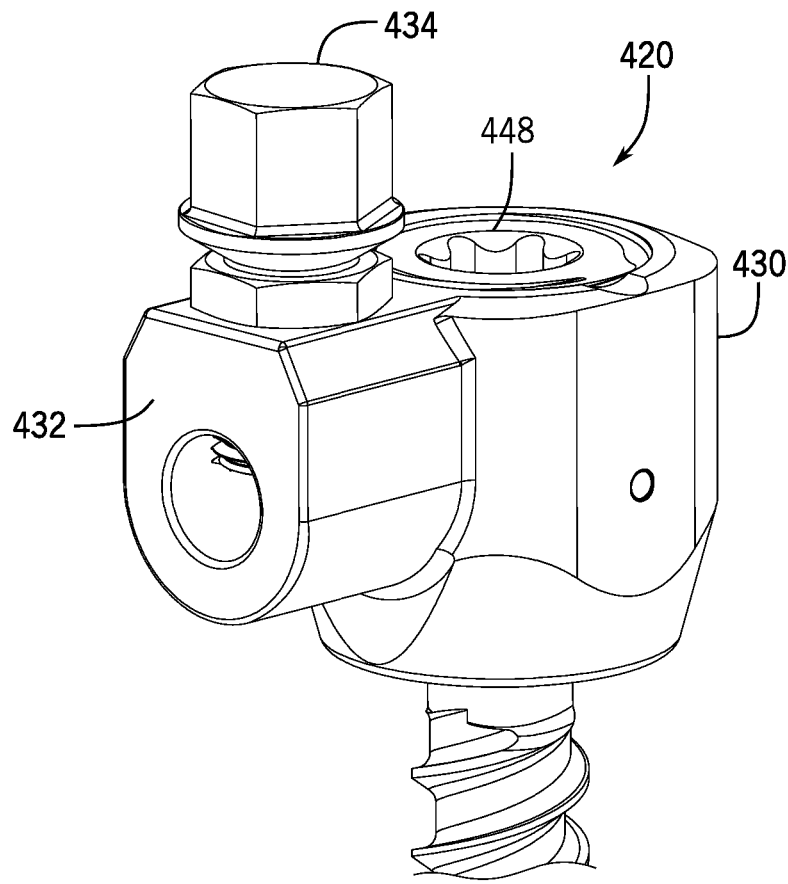
Figure 132:
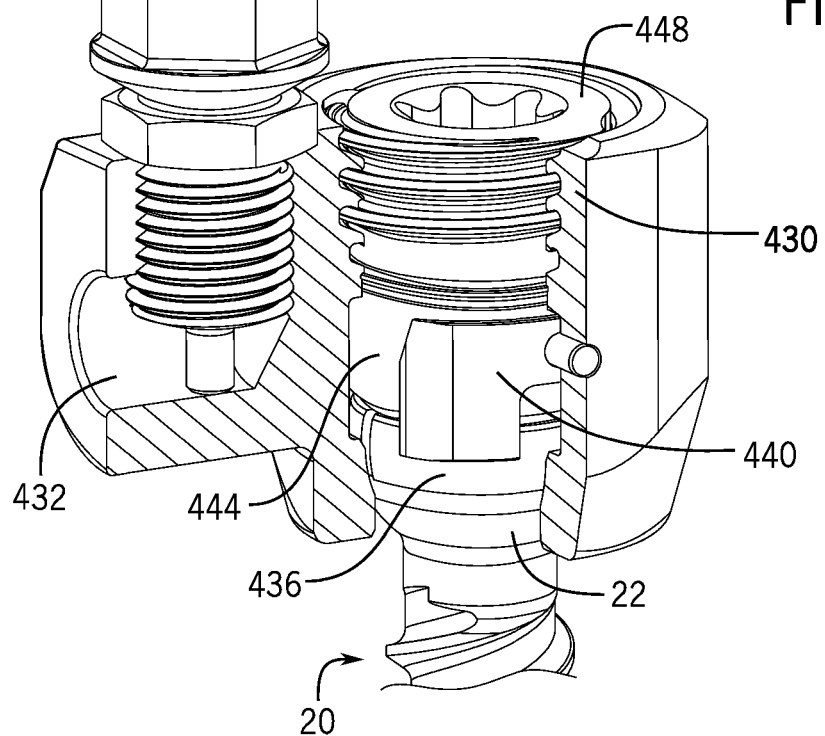

FIG. 132 is a partially cut-away perspective view of the multi-planar pivotal bone anchor assembly of FIG. 131.

Figure 133:
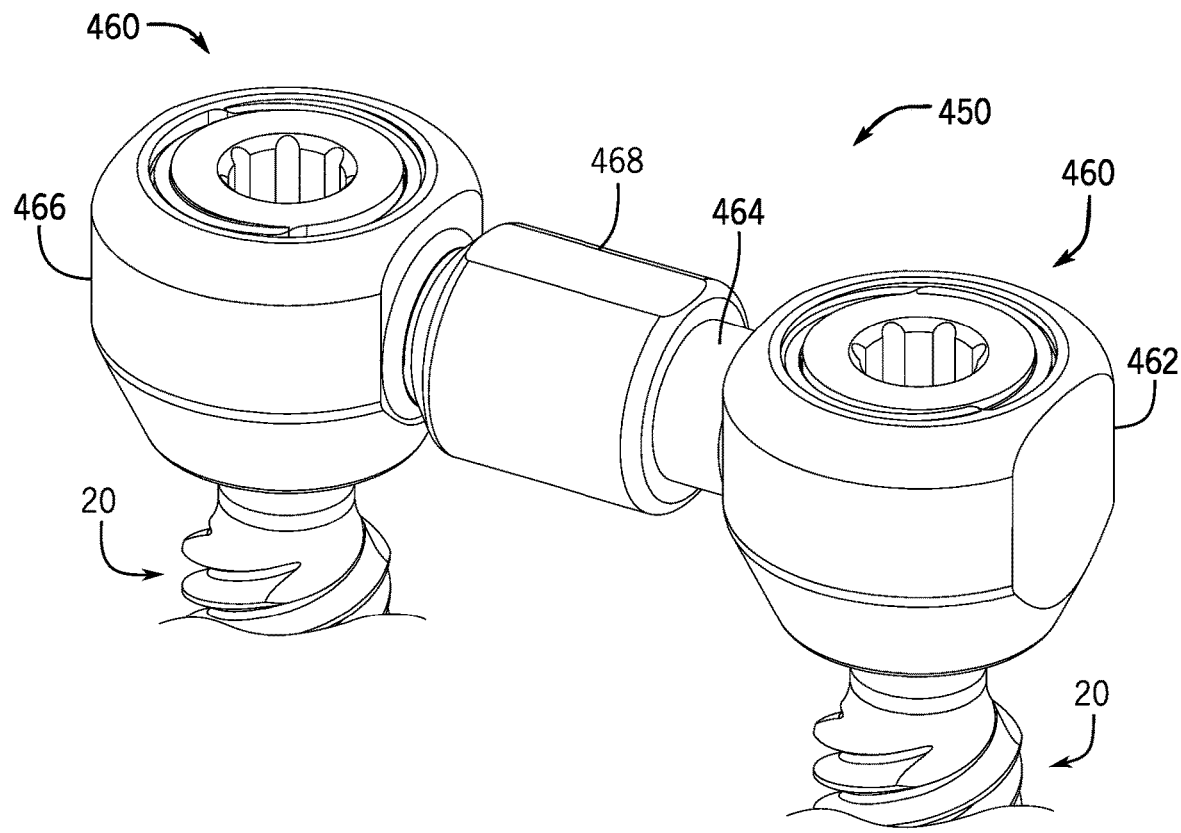

FIG. 133 is a perspective view of a pair of multi-planar pivotal bone anchor assemblies with housings configured for adjacent level connection, in accordance with yet another representative embodiment of the present disclosure.

Figure 134:
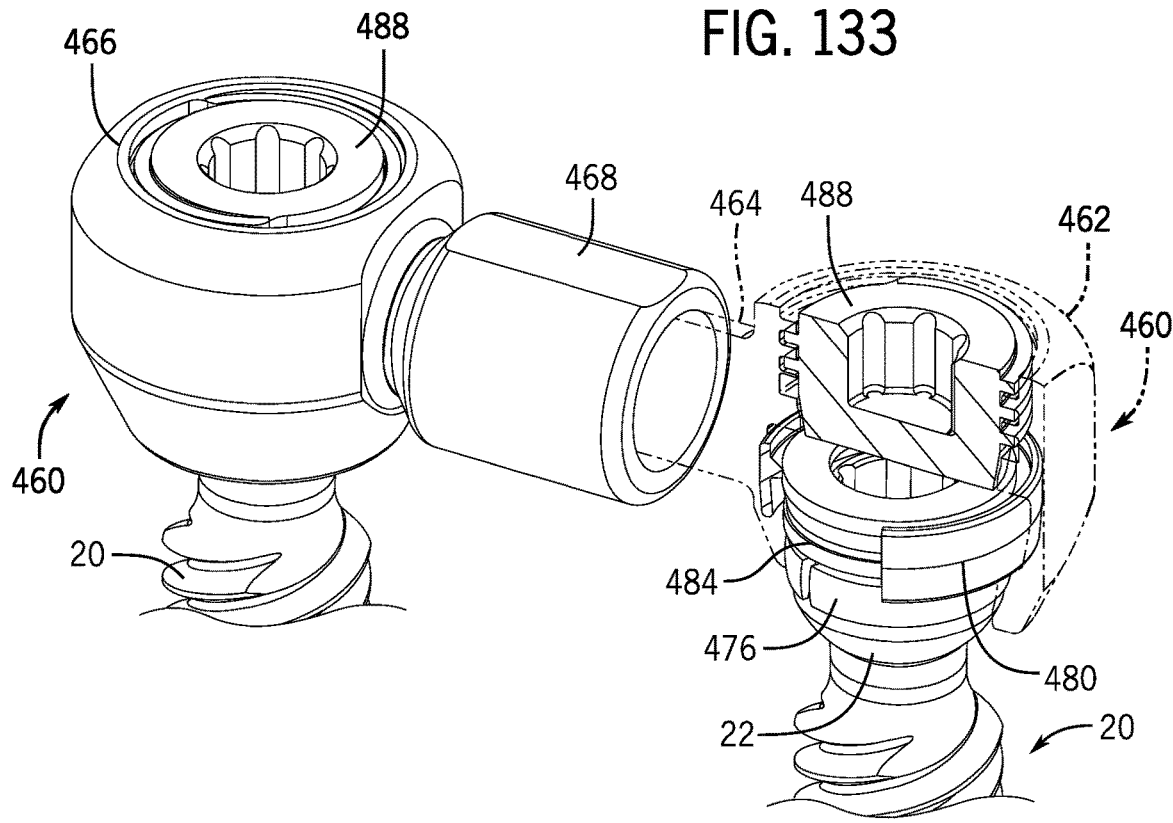

FIG. 134 is a partially cut-away perspective view of the pair of multi-planar pivotal bone anchor assemblies of FIG. 133.

Those skilled in the art will appreciate and understand that, according to common practice, various features and elements of the drawings described above are not necessarily drawn to scale, and that the dimensions and relative positions between the features or elements may be expanded, reduced or otherwise altered to more clearly illustrate the various embodiments of the present disclosure depicted therein.

DETAILED DESCRIPTION

The following description, in conjunction with the accompanying drawings described above, is provided as an enabling teaching of exemplary embodiments of a pivotal bone anchor apparatus, assembly, or system that generally includes a universal shank head for use with a plurality of different types of functional modular receiver sub-assemblies, together with methods for assembling and using the pivotal bone anchor apparatus, assembly, or system. As described below, the apparatuses, assemblies, systems, and/or methods of the present disclosure can provide several significant advantages and benefits over other pivotal bone anchors known in the art. However, the recited advantages are not meant to be limiting in any way, as one skilled in the art will appreciate that other advantages may also be realized upon practicing the present disclosure.

Furthermore, those skilled in the relevant art will recognize that changes can be made to the described embodiments while still obtaining the beneficial results. It will also be apparent that some of the advantages and benefits of the described embodiments can be obtained by selecting some of the features of the embodiments without utilizing other features, and that features from one embodiment may be interchanged or combined with features from other embodiments in any appropriate combination. For example, any individual or collective features of method embodiments may be applied to apparatus, product or system embodiments, and vice versa. Accordingly, those who work in the art will recognize that many modifications and adaptations to the embodiments described are possible and may even be desirable in certain circumstances, and are a part of the disclosure. Thus, the present disclosure is provided as an illustration of the principles of the embodiments and not in limitation thereof, since the scope of the invention is to be defined by the claims.

Referring now in more detail to the drawing figures, wherein like parts are identified with like reference numerals throughout the several views, FIG. 1 illustrates a representative embodiment of a multi-planar pivotal bone anchor apparatus or assembly 10 (hereinafter referenced to as "the multi-planar assembly 10") for securing an elongate rod to patient bone in spinal surgery. The multi-planar assembly 10 generally includes a bone anchor, such as shank 20, having a capture portion, such as universal shank head 22, at a proximal end 23, and an anchor portion or shank body 40 extending distally from the shank head 22 for securement to patient bone. The multi-planar assembly also generally includes a multi-planar receiver 100 having an internal cavity 126 in a base portion 134 and two upright arms 104 extending upwardly from the base portion to define a rod channel 106 for receiving an elongate rod 90. The multi-planar receiver 100 can be initially pivotably secured to the universal shank head 22 with a number of separate internal components that have been pre-assembled into the internal cavity 126 and the rod channel 106 to form a receiver sub-assembly. These components can include a multi-planar resilient open pivoting retainer 70, a pressure insert 150, and a single piece or multi-piece positioner 170 that may secured in different ways within the internal cavity 126 of the base portion 134, for example, with positioner pins 190. After an elongate rod 90 has been positioned within a lower portion of the rod channel 106, a closure 80 can be threadably or otherwise secured into an upper portion of the rod channel to apply pressure to an upper surface of the elongate rod, thereby locking both the elongate rod 90 and the multi-planar assembly 10 into a final locked position.

Also shown in FIG. 1, in one aspect of the disclosure the bone anchor or shank 20 can further include an optional removable resilient capture recess protection sleeve 50 installed over a horizontal capture recess 32 that is formed into the universal shank head 22 or capture portion of the bone anchor, so as to prevent soft tissue and bone chips from entering and fouling the capture recess 32 prior to introduction of the universal shank head 22 into a receiver sub-assembly, as described in more detail below.

With reference to FIGS. 2-8, the bone anchor or shank 20 generally comprises a capture portion or shank head 22 at a proximal end 23 having a universal shank head structure, and an anchor portion or shank body 40 extending distally from the universal shank head 22 toward a tip 48 at a distal end 49. The shank 20 is elongate, with the shank body 40 having a helically wound bone implantable thread 44 (single, dual, or multiple-lead thread form) extending from near a neck 42 located adjacent to the shank head 22, to a distal tip 48 of the body 40 and extending radially outwardly therefrom. During use, the shank body 40 utilizing the thread 44 for gripping and advancement is implanted into the vertebra (not shown) of a patient leading with the tip 48 and driven down into the vertebra with an installation or driving tool (also not shown), so as to be implanted in the vertebra to near the neck 42 of the shank 20, as more fully described in the paragraphs below. The shank 20 has a central longitudinal axis, or axis of rotation, that is generally identified by the reference numeral 21.

The neck 42 extends axially upward from the shank body 40. The neck 42 may be of the same or is typically of a slightly reduced radius as compared to an adjacent upper end of the shank body 40 where the thread 44 terminates. In one aspect the threaded shank body 40 and the neck 42 can together define an anchor portion of the shank 20. Further extending axially and outwardly from the neck 42 is the universal shank head 22 that provides a connective or capture apparatus disposed at a distance from the shank body 40, and thus at a distance from the vertebra when the shank body 40 is implanted in such vertebra.

Figure 9:
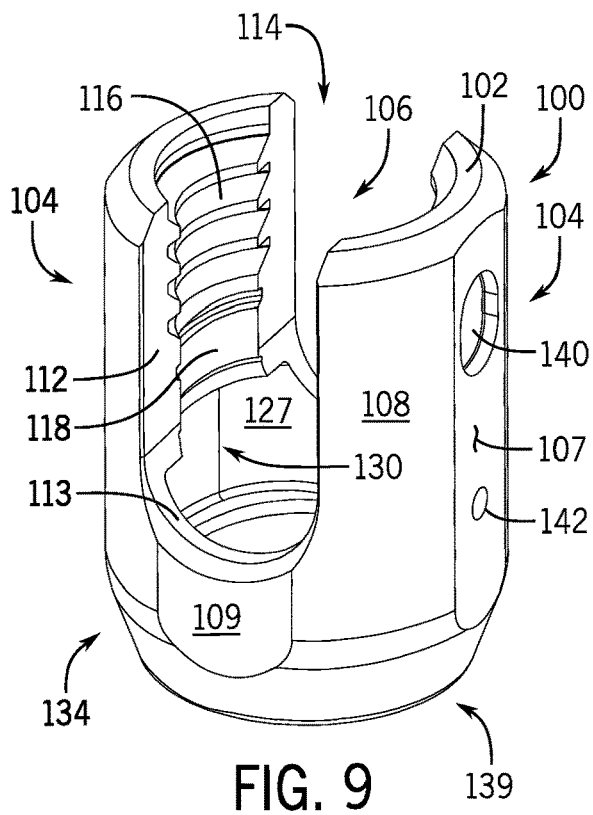
FIG. 9 is a perspective view of the multi-planar receiver of the multi-planar pivotal bone anchor assembly of FIG. 1.
Figure 10:
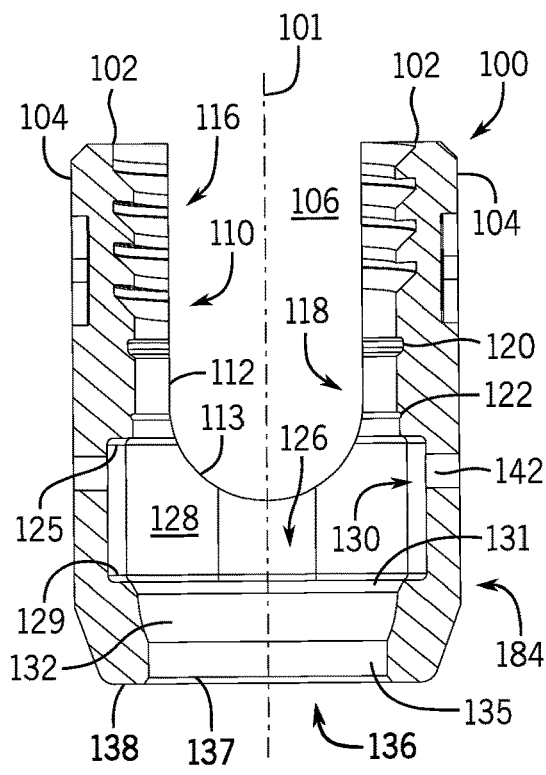
FIG. 10 is a cross-sectional view of the multi-planar receiver of FIG. 9.
Figure 11:
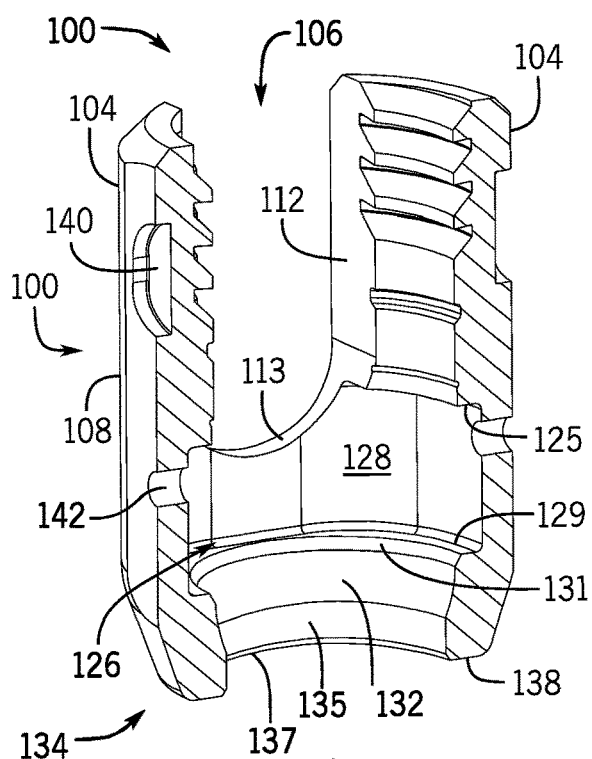
FIG. 11 is a cross-sectional perspective view of the multi-planar receiver of FIG. 9.
Figure 12:
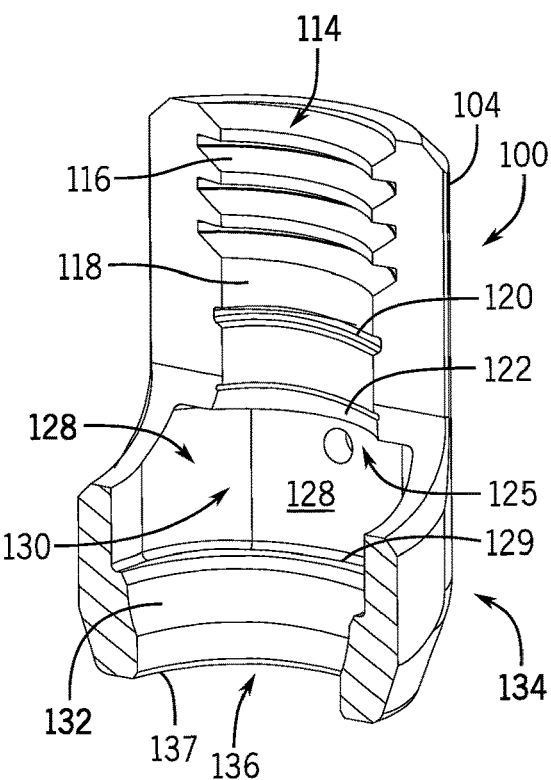
FIG. 12 is another cross-sectional perspective view of the multi-planar receiver of FIG. 9.

The universal shank head 22 is configured for a pivotable connection between the shank 20 (with attached retainer 70) and the multi-planar receiver 100 prior to fixing of the shank 20 in a desired position with respect to the multi-planar receiver 100. The universal shank head 22 has an outer, convex and partial spherical lower surface 38 that extends outwardly and upwardly from the neck 42 and terminates at lower cylindrical surface 36 that can be substantially parallel to the shank axis 21, and having a radius smaller than the radius of the spherical lower surface 38. The partial spherical lower surface 38 has an outer radius that is the same or substantially similar to an outer radius of the multi-planar retainer 70, as will be described in greater detail below, with the partial spherical surface 38 and the partial spherical outer surface of the multi-planar retainer 70 participating in the ball and socket joint formed by the shank 20 and the attached multi-planar retainer 70 within a partial spherical seating surface 132 defining a lower portion of the cavity 126 of the multi-planar receiver 100. (see FIGS. 10-12).

The lower cylindrical surface 36 extends upward to a lower annular shelf or ledge surface 35 that is disposed perpendicular to the shank axis 21. Extending upwardly from the lower ledge surface 35 is an outwardly-facing inner recess surface 34 having a radius that is smaller than the radius of the lower cylindrical surface 36. Extending outwardly from the inner recess surface 34 is another annular self or upper ledge surface 33 that faces toward the lower ledge surface 35 and is also substantially perpendicular to the shank longitudinal axis 21. As will be discussed in greater detail below, the upper ledge surface 33, the inner recess surface 34, and the lower ledge surface 35 together define a circumferential horizontal capture recess 32, and cooperate to capture and fix the resilient open pivoting multi-planar retainer 70 to the universal shank head 22, prohibiting movement of the multi-planar retainer 70 in the direction of the shank axis 21 once the multi-planar retainer 70 is located between the ledges 33 and 35.

As will be described in greater detail below, the structure of the universal shank head 22 having the circumferential horizontal capture recess 32, as shown in FIGS. 2-4, allows for the shank head 22 to connect with either a multi-planar or a uni-planar receiver sub-assembly, and in particular with either a multi-planar or a uni-planar pivoting retainer which is engageable with a complementary multi-planar or uni-planar receiver, respectively. This feature of the pivotal bone anchor assembly or system can advantageously provide for selectable multi-planar or uni-planar motion of a receiver with respect to the shank head 22, as determined by a surgeon or medical professional in an operating environment after implantation of the shank body 44 into a vertebra, but prior to the coupling or capture of the shank head 22 with a respective receiver sub-assembly. As defined herein, the capability of connecting with either a multi-planar or a uni-planar receiver sub-assembly in an operating environment, to the same shank head geometry without further configuration or modification thereto, is useful for designating the shank head 22 as a universal shank head.

Furthermore, it will be appreciated that the horizontal capture recess 32 extends circumferentially entirely around the universal shank head 22, without any planar surfaces or flats being formed into the sides of the shank head 22. This results in a continuous 360 degree contact between the universal shank head 22, the multi-planar retainer 70, and the receiver seating surface 132 (FIGS. 10-12) that avoids high-stress discontinuities while providing for a smooth continuous engagement between the internal components that resists pull-out at all angulation angles. In a multi-planar embodiment, such as that shown in FIGS. 1-69, the partial spherical outer surface 74 of the resilient open pivoting retainer 70 and the partial spherical seating surface 132 of the receiver cavity 126 are substantially continuous (except for the retainer slot) and unbroken, providing for polyaxial, multi-axial, or multi-planar pivotal motion between the shank 20 and the multi-planar receiver 100. In a uni-planar embodiment, such as that shown in FIG. 76-124, the partial spherical outer surface of the resilient open retainer and the partial spherical seating surface of the receiver cavity are modified to include outwardly-projecting pegs and inwardly-extending pockets, respectively, that restrict the pivotal motion between the shank and the receiver to a single plane. Nevertheless, the continuous 360 degree contact between the shank head, the retainer, and the receiver seating surfaces is still maintained in the uni-planar embodiment to provide a secure pull-out resistant connection between the components at all angulation angles, again, while all using the same shank head geometry.

Figure 22:
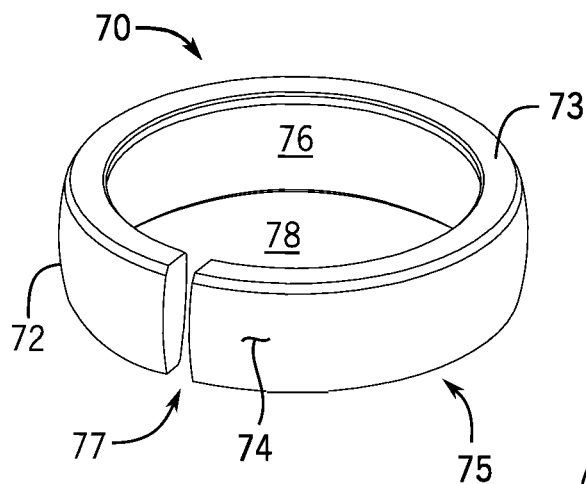
FIG. 22 is a perspective view of the multi-planar retainer of the multi-planar pivotal bone anchor assembly of FIG. 1.
Figure 23:
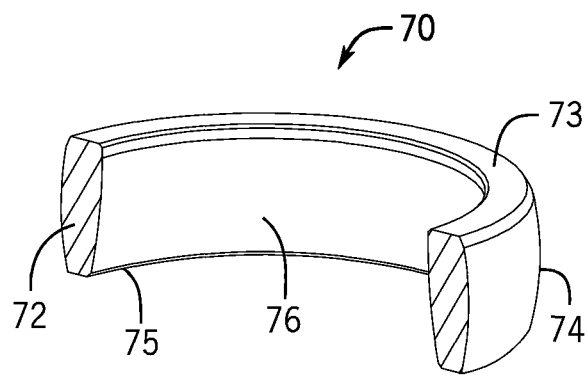
FIG. 23 is a cross-sectional perspective view of the multi-planar retainer of FIG. 22.

As shown in the bone anchor embodiment of FIGS. 2-8, in one aspect the inner recess surface 34 can have a curved profile that gradually curves downwardly and outwardly as moving from the upper ledge surface 33 to the lower ledge surface 35, and which can be complementary with a curvate inner surface 76 of the resilient open multi-planar retainer 70 (see FIGS. 22-23). Nevertheless, it is understood that the inner recess surface 34 can have a variety of profiles, including but not limited to a cylindrical profile, a frusto-conical profile, a reversed curved profile that gradually curves downwardly and inwardly as moving from the upper ledge surface 33 to the lower ledge surface 35, and the like. In addition, the profile of the inner recess surface 34 may or may not be closely complementary with and engaged by the inner surface of the resilient open pivoting multi-planar retainer 70.

Extending upwardly from the upper ledge surface 33 is an upper cylindrical surface 30 having a radius that is substantially equal to the radius of the lower cylindrical surface 36. Extending further upwardly from the upper cylindrical surface 30 is an upper partial spherical or domed surface 28. The upper partial spherical surface 28 has an outer radius configured for sliding cooperation and ultimate frictional mating with a substantially spherical concave bottom surface 166 of the pressure insert 150 (see FIGS. 14-15) that has the same or substantially similar radius as the partial spherical surface 28. In addition, the radius of the upper partial spherical surface 28 can substantially equal to both the radius of the lower partial spherical surface 38 and the partial spherical outer surface 74 of the multi-planar retainer 70 (see FIGS. 22-23), so that the three partial spherical surfaces 28, 74, 38 align, when the resilient open multi-planar retainer 70 is captured or secured within the capture recess 32, to form a united universal shank head 22/multi-planar pivoting retainer 70 structure that is substantially spherical.

Located near or adjacent to the upper partial spherical surface 28 is an annular planar top surface 26 that surrounds an internal drive feature 24 or drive socket. The illustrated internal drive feature 24 is an aperture formed in the top surface 26 and has a hex shape designed to receive a hex tool (not shown) of an Allen wrench type, into the aperture for rotating and driving the shank body 40. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base surface 25 of the drive feature 24 is disposed perpendicular to the shank axis 21, with the drive feature 24 otherwise being coaxial with the axis 21. In operation, a driving tool is received in the internal drive feature 24, being seated at the base surface 25 and engaging the six faces of the drive feature 24 for both driving and rotating the shank body 40 into the vertebra, either before or after the shank 20 is attached to the receiver sub-assembly 146, with the shank body 40 being driven into the vertebra with the driving tool extending into the multi-planar receiver 100.

In one aspect the shank 20 can be cannulated, with a bore 46 extending through the entire length thereof, and centered about the central longitudinal axis 21 of the shank 20. The bore 46 is defined by an inner cylindrical wall of the shank 20 and has a circular opening at the shank tip 48 and an upper opening communicating with the internal drive 24 at the surface 25. The bore 46 is coaxial with the threaded shank body 40 and the universal shank head 22. The bore 46 provides a passage through the shank 20 interior for a length of wire (not shown) inserted into the vertebra prior to the insertion of the shank body 40, the wire providing a guide for insertion of the shank body 40 into the vertebra. The bore can also provide for a pin to extend therethrough and beyond the shank tip, the pin being associated with a tool to facilitate insertion of the shank body into the vertebra.

To provide a biologically active interface with the bone, the threaded shank body 40 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_9)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 5-8, the optional removable capture recess protection device or sleeve 50 generally comprises a resilient or flexible sleeve body 54 that is sized and shaped to fit firmly over the capture recess 32 during installation of the bone anchor into patient bone prior to the shank 20 being attached to the receiver sub-assembly 146, as shown in FIGS. 45-64. The sleeve body 54 generally has a top surface 53, a bottom surface 55, an outer surface 56, and in inner surface 58 with a inwardly protruding raised cylindrical structure 62 defined by an upper edge 61 and a lower edge 63. An upper inner cylindrical surface 60 extends between upper edge 61 and the top surface 53 of the sleeve body, with a mirroring lower inner cylindrical surface 64 extending between lower edge 63 and the bottom surface 55 of the sleeve body. In one aspect the upper and lower edge surfaces 61, 63 of the raised cylindrical structure 62 can taper toward a center of the raised cylindrical structure 62 as projecting inwardly from the inner cylindrical surfaces 60, 64. It will be appreciated that the disclosed embodiment of the capture recess protection sleeve 50 is only exemplary, and that other embodiments and configurations for the protection sleeve are also possible and considered to fall within the scope of the present disclosure, particularly with having the functionality of preventing material from entering the shank capture recess.

Upon installation of the capture recess protection sleeve 50 to the universal shank head 22, as illustrated in FIG. 8, the upper and lower edge surfaces 61, 63 are generally sized to fit between the upper and lower ledge surfaces 33, 35 of the capture recess 32, so that the raised cylindrical structure 62 projects cleanly into the capture recess 32. This can allow for the upper and lower inner cylindrical surfaces 60, 64 of the sleeve 50 to resiliently engage the upper and lower cylindrical surfaces 30, 36 of the shank head 22, respectively, to provide a firm but flexible seal that prevents soft tissue and bone chips from entering and fouling the capture recess 32 prior to the installation of the pre-assembled receiver sub-assembly.

The capture recess protection sleeve 50 can be made from a flexible, resilient, or semi-resilient material, such as a polymer or soft metal, and some embodiments can be made from a bio-degradable polymer or similar material. In one embodiment the capture recess protection sleeve 50 can include a lanyard (not shown) that allows the surgeon to manually pull the sleeve 50 off of the shank head during attachment of the receiver sub-assembly. In another embodiment the sleeve 50 may also be provided with a pre-formed shear or tear line (not shown) opposite the lanyard attachment point that allows for the sleeve 50 to be split or torn apart after being pushed down into the neck area of the bone anchor or shank 20, facilitating removal of the sleeve by the lanyard after use.

Illustrated in FIGS. 9-12 is the multi-planar receiver having a generally U-shaped appearance with a partially discontinuous substantially cylindrical inner profile and a partially cylindrical and partially faceted outer profile, although other profiles are contemplated. The multi-planar receiver 100 also has a central longitudinal axis 101, or axis of rotation, that is shown in FIG. 1 as being aligned with the central longitudinal axis 21 of the shank 20, such orientation being desirable, but not required during assembly of the multi-planar receiver 100 with the shank 20. After the receiver 100 is pivotally attached to the universal shank head 22, either before or after the shank 20 is implanted in a vertebra, the receiver axis 101 is typically disposed at an angle with respect to the shank axis 21 as shown, for example, in FIGS. 65-69.

The multi-planar receiver 100 includes a substantially cylindrical base 134 integral with a pair of opposed upright arms 104 forming an upwardly open channel 106 between the arms 104 for receiving the elongate rod 90. Each of the receiver arms 104 has an interior face 110 that includes a discontinuous upper portion of a generally cylindrical central bore 114 that extends from the top surfaces 102 of the upright arms 104 at the proximal end 101 of the receiver, downwardly through the open channel 106 and the base 134 to a bottom opening 136 at the distal end 139 of the multi-planar receiver 100. The channel or upper discontinuous portion of the central bore 114 is bounded on either side by opposing planar surfaces 112 that curve downwardly into U-shaped lower saddle surfaces 113, with the opposing planar surfaces 112 and lower saddle surface 113 defining the front and back ends of the upwardly open channel 106.

The upper discontinuous portion of the cylindrical central bore 114 has a partial helically wound guide and advancement structure 116 extending radially inwardly from the interior face 110 of the channel 106 and located adjacent the top surfaces 102 of the arms 104. In the illustrated embodiment, the guide and advancement structure 116 is a partial helically wound interlocking flangeform configured to mate under rotation with a similar structure on the closure 80, as described more fully below. However, it is foreseen that the guide and advancement structure 116 could alternatively be a square-shaped thread, a buttress thread, a modified buttress thread, a reverse angle thread or other thread-like or non-thread-like helically wound discontinuous advancement structure for operably guiding under rotation and advancing the closure 80 downward between the arms 104, as well as eventual torqueing when the closure 80 abuts against the elongate rod 90. Additionally, the various structures and surfaces forming the guide and advancement structure 116 can be configured to resist, to inhibit, to limit, or to preferentially control the splay of the upright arms 104 under the rotation and advancing the closure 80 downward between the arms 104.

The upper discontinuous portion of the cylindrical central bore 114 immediately below the guide and advancement structure 116 is defined by a discontinuous cylindrical surface 118 that extends downward from the guide and advancement structure 116 to a positioner chamber portion 128 of the receiver cavity 126. Formed into the discontinuous cylindrical surface 118 is an upper groove 120 spaced below the guide and advancement structure 116, and a lower groove 122 located between the upper groove 122 and the receiver cavity 126. In one aspect the upper groove 120 may be deeper and wider than the lower groove 122.

Communicating with and located beneath the channel 106 of the multi-planar receiver 100 at the base portion 134 thereof is the cavity 126 having an upper positioner chamber portion 128 and a lower seating surface portion 132 located proximate the bottom opening 136. The positioner chamber 128 is generally defined by upper non-annular step surfaces 125 demarking the bottom of the discontinuous cylindrical surface 118, a lower non-annular step surface 129, and vertical sidewall surfaces 127 extending between the step surfaces or between the lower non-annular step surface 129 and the U-shaped lower saddle surfaces 113 of the channel 106. In one aspect the positioner chamber 128 can have a non-round oblong shape with a long axis orientated perpendicular to the long axis of the open channel, with the upper non-annular step surfaces 125 forming undercuts that extend deeper into the interior faces 110 of the upright arms 104 than either of the upper and lower grooves 120, 122 or the guide and advancement structure 116, thereby forming end spaces 130 at opposite ends of the positioner chamber 128. As described in more detail below, the end spaces 130 are sized and shaped to accommodate the positioner pieces 172 of the multi-planar two-piece positioner 170 upon their installation into the multi-planar receiver 100.

The lower seating surface portion 132 of the cavity 126 is spaced slightly below the lower non-annular step surface 129 of the positioner chamber 128 by frusto-conical or chamfer surface 131. Moreover, the seating surface 132 in the multi-planar embodiment of the receiver 100 can be a 360 degree continuous partial spherical that is uninterrupted both across the width and around the circumference thereof. As noted above, the partial spherical seating surface 132 is sized and shaped for slidably mating with the partial spherical outer surface 74 of the resilient open pivoting multi-planar retainer 70 as well as the upper partial spherical surface 28 and the lower partial spherical surface 38 of the universal shank head 22, and ultimately frictionally mating with the same outer surfaces 74, 36, as described in greater detail below.

Immediately below the seating surface 132 is a lowermost cylindrical surface 135 that generally defines the bottom opening 136 that communicates with both the cavity 126 and a receiver lower exterior or bottom 138 of the base 134. The cylindrical surface 135 is substantially coaxially aligned with respect to the longitudinal axis 101 of the multi-planar receiver 100. The cylindrical surface 135 is also sized and shaped to be smaller than an outer radial dimension of the multi-planar retainer 70 when the retainer 70 is fixed to the universal shank head 22, so as to form a restriction to prevent the retainer 70 and attached shank head 22 from passing through the cavity 126 and out the lower exterior 138 of the multi-planar receiver 100 during operation thereof. A bottom frusto-conical or chamfer surface 137 extending between the lowermost cylindrical surface 135 and the bottom surface 138 of the receiver 110 can provide for increased angulation of the shank 20 after capture of the shank head 22 within the receiver cavity 126 by the retainer 70.

An opposed pair of positioner pin apertures 142 extend through the sidewalls of the positioner chamber 128 below the upright arms 104, between the vertical sidewall surfaces 127 and the outer surface of the base 134. As described in greater detail below, the positioner pin apertures 142 are sized to receive the body portion 194 of a positioner pin 190 in a press-fit engagement upon the installation of the positioner pin 190 into the positioner chamber 128 together with a positioner piece 172, so as to hold and secure the positioner piece 172 in position within the end space 130 of the positioner chamber 128 and against the vertical sidewall surfaces 127.

As noted above, the outer surface 108 of the multi-planar receiver 100 can have a partially cylindrical and partially faceted outer profile. In one aspect the faceted or planar portions can include side outer planar faces 107 on outer surfaces of the upright arms 104 opposite the interior faces 110 and extending downward to the outer side surfaces of the base portion 134. The faceted or planar portions can also include front and back outer planar faces 109 on the receiver base 134 below the open channel 106, and which can be oriented perpendicular to the side outer planar faces 107. In addition, a pair of tool receiving and engaging recesses 140 can be formed into the side outer planar faces 107 between each top surface 102 and the pin apertures 142. In one aspect the tool receiving and engaging recesses 140 can have recessed surfaces that are parallel with the side outer planar faces 107. The faceted or planar portions 107, 109 of the outer surface 108 of the multi-planar receiver 100 and the tool receiving and engaging recesses 140 can serve together as outer tool engagement surfaces that allow for tooling to more securely engage and hold the multi-planar receiver 100 during an initial pre-assembly with the separate open pivoting multi-planar retainer 70, pressure insert 150, and multi-piece positioner 150 into the multi-planar receiver 100 to form the multi-planar receiver sub-assembly 146, as well as during coupling of the receiver sub-assembly to the shank 20 after or before the implantation of the shank body 40 into a vertebra, and during further assembly of the multi-planar assembly 10 with the elongate rod 90 and the closure 80.

It is foreseen that other shapes and configurations for the interior and exterior surfaces of the multi-planar receiver 100, different from those shown in the drawings while providing for similar interaction and functionality of the various components of the pivotal bone anchor assembly, are also possible and considered to fall within the scope of the present disclosure. For example, the pressure insert can be positioned within the receiver in different ways, such as snapped in place, rotated in place, crimped in place, etc.

Figure 69:
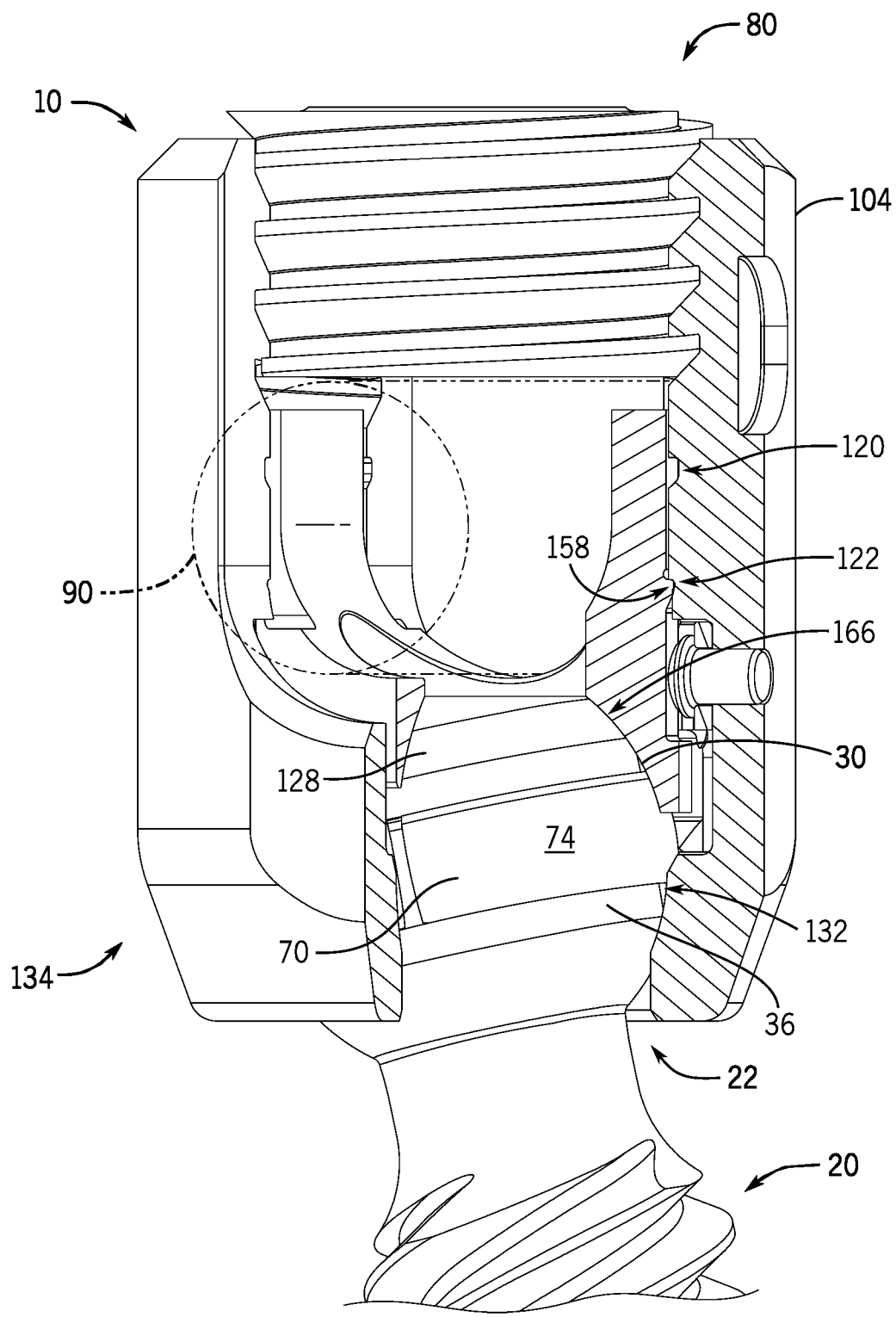
FIG. 69 is a partially cut-away and sectioned perspective view of the multi-planar receiver sub-assembly and coupled universal shank head with an elongate rod and closure in a fully locked configuration, thereby forming a completely assembled representative embodiment of a multi-planar pivotal bone anchor apparatus or system, with the bone anchor being pivoted relative to the receiver.

Illustrated in FIGS. 13-17 is the pressure insert 150 having a generally cylindrical base 162 with upwardly projecting arms 152 that define an insert channel 154 that is alignable with the channel 106 of the multi-planar receiver 100 upon installation into the receiver 100, and having a width between inner surfaces 155 for operably snugly receiving the elongate rod 90 between the insert arms 154. In one aspect the insert arms 152 extend upward to top surfaces 153 that are spaced below a top surface of an elongate rod 90 when the rod is positioned in the insert and receiver channels 154, 106. As can be seen in the drawings, an upper curvate rod seating surface 156 extends between lower portions the inserts arms 152 and is engageable with the underside surface of the elongate rod 90. The pressure insert 150 also includes an upwardly-concave spherically shaped bottom surface 166 that is configured to engage the upper partial spherical surface 28 of the universal shank head 22, and to also engage the partial spherical outer surface 74 of the resilient open pivoting retainer 70 at high angulation of the bone anchor 20 relative to the multi-planar receiver 100 (FIG. 69). A central tool receiving aperture 160 can extend vertically through the center of pressure insert to allow passage for a driving tool to engage the internal drive feature 24 or drive socket formed into the top of the shank head 22.

Protruding outwardly from the outer side surfaces 157 of the arms 152 of the pressure insert 150 are opposing insert ridges 158 that are engageable with the upper grooves 120 formed into the interior faces 110 of the receiver upright arms 104 when the receiver sub-assembly is in a pre-assembled shipping configuration. The insert ridges 158 are subsequently engageable with the lower grooves 122 formed into the interior faces 110 when the pivotal bone anchor assembly is in a friction fit configuration. In one aspect a small rounded relief groove 159 can be formed at the junction between the vertical outer side surfaces 157 of the insert arms 152 and the top surfaces of the insert ridges, for reasons described in more detail below.

The pressure insert 150 further includes opposing skirts 164 that extend outward from a lower portion of the cylindrical base 162. Each skirt 164 includes a partial cylindrical outer surface 163 and a partial annular bottom surface 165 to define a lower skirt edge 167 that is configured to engage, as described in more detail below, an upper ramp surface that defines the top of an upper protrusion extending inwardly from an outer wing portion of a positioner piece.

It is foreseen that other shapes and configurations for the interior and exterior surfaces of the pressure insert, different from those shown in the drawings while providing for similar interaction and functionality of the various components of the pivotal bone anchor assembly, are also possible and considered to fall within the scope of the present disclosure.

Illustrated in FIGS. 18-21 are the multi-planar two-piece positioner 170 and positioner pins 190, which are configured to receive and maintain the multi-planar retainer 70 within the positioner chamber 128 and centrally aligned along the receiver axis 101 during all phases of transport and storage of the receiver sub-assembly, as well as during assembly of the receiver sub-assembly with a mating universal shank head 22. The multi-planar positioner 170 generally comprises two multi-planar positioner pieces 172, with each positioner piece 172 having a center portion 174 with an upper pin aperture 176 that is used to pin the center portion 174 to the vertical sidewall surface 127 of the positioner chamber 128 with a positioner pin 190, as well as a lower cut-out window 178 below the center portion 174 to provide for greater flexure of the positioner piece. Each positioner piece 172 further includes bendable outer wing portions 180 on either side of the center portion 174 that flex outwardly under load or pressure, and which then spring back inwardly when released. During use the outer wing portions 180 are generally bent or flexed outwardly under load or pressure applied by the retainer 70 from below or by the pressure insert 170 from above, with the wing portions 180 then springing back inwardly to capture and hold the retainer 70 or to abut the outer surface of the insert 150, respectively. It will be appreciated that the size and shape of the cut-out window 178 can be varied to control the spring force of the outer wing portions 180.

Also shown in the drawings, upper flanges 182 and lower flanges 186 project inwardly from the inner face 181 of the outer wing portions 180. The angled tops of the upper flanges 182 define upper ramp surfaces 184 while the undersides of the upper flanges 182 define upper retainer capture surfaces 185. Similarly, the angled tops of the lower flanges 186 define lower ramp surfaces 188 that also serve as lower retainer capture surfaces. As described in more detail below, the upper retainer capture surfaces 185 of the upper flanges 182 and the lower retainer capture surfaces 188 of the lower flanges 186 loosely define a portion of an open discontinuous retainer capture chamber. In addition, the upper flanges 182 further include upper leading edge contact surfaces 183 configured to engage a lower outer surface of the pressure insert 170, while the lower flanges 186 include lower leading edge contact surfaces 187 configured to engage the partial spherical outer surface 74 of the resilient open pivoting retainer 70. It is foreseen that other shapes and configurations for the interior and exterior surfaces of the multi-planar two-piece positioner 170, different from those shown in the drawings while providing for similar interaction and functionality of the various components of the pivotal bone anchor assembly, are also possible and considered to fall within the scope of the present disclosure. For example, the positioner can be of unitary construction.

A positioner pin 190 is provided for each positioner piece 172 of the two piece positioner 170. Each positioner pin 190 generally comprises a break-off pin guide extension 198 at a distal end that guides the pin 190 first through the upper pin aperture 176 in the center portion 174 of the positioner piece 172, and then into and through the positioner pin aperture 142 that extends through the sidewall of the positioner chamber 128 of the multi-planar receiver 100. Each positioner pin 190 further comprises a press-fit body 194 with a cap 192 at a proximal end that secures the center portion 172 of the positioner piece 172 within the positioner chamber 128, once the pin body 194 is pressed into the positioner pin aperture 142 of the receiver 100. In one aspect a break off groove 196 can be cut around the circumference of the pin to defined the boundary between the break-off pin guide extension 198 and the press-fit body 194. In addition, it is foreseen that the positioner could be used without break-off pins.

With particular reference to FIGS. 22-23, the multi-planar embodiment of the resilient open pivoting retainer 70 generally comprises a split ring body 72 defining a central aperture 78, and having a slot or slit 77. The slit 77 allows the ring body 72 to expand when pressure is applied to the inner surface 76, and then to contract back to its original shape when the pressure is released. As described above, the inner surface 76 of the multi-planar retainer 70 is generally contoured to match the outwardly-facing inner recess surface 34 of the universal shank head 22, which is shown in FIGS. 2-8 as having a curved profile that gradually curves downwardly and outwardly as moving from the upper ledge surface 33 to the lower ledge surface 35. Nevertheless, and as described in more detail below, the inner surface 76 of the multi-planar retainer 70 and the inner recess surface 34 of the universal shank head 22 can have complementary contours different from the curved profile selected in the illustrated embodiment of the pivotal bone anchor assembly 10.

The split ring body 72 has a top surface 73, a bottom surface 75, and a spacing between the top and bottom surface 73, 75 that allows the multi-planar retainer 70 to snap in the capture recess 32, with the top surface 53 adjacent the upper ledge surface 33 and the bottom surface 75 adjacent the lower ledge surface 35, upon assembly within the universal shank head 22. In one aspect the diameter of the shaped inner surface 76 of the multi-planar retainer 70 can be substantially equal to the diameter of the shaped inner recess surface 34, so that the retainer inner surface 76 engages the recess inner surface 34 with a substantially neutral fit, with the ring body 72 being neither substantially compressed nor substantially expanded after coupling with the capture recess and subsequent engagement in a friction fit or fully locked configuration. It will be appreciated by one of skill in the art that, depending on manufacturing tolerances of the two components, that the ring body 72 could be in a slightly loose, slightly expanded, or slightly deformed state after the capturing of the shank head 22 by the retainer 70 within the positioner chamber portion 128 of the receiver cavity 126. Nevertheless, the multi-planar retainer 70 is generally dimensioned to be slidably rotatable within the horizontal capture recess 32 after the shank 20 and retainer 70 are moved downward into contact with the partial spherical seating surface 132 of the multi-planar receiver 100, but prior to the loading of the multi-planar retainer 70 and universal shank head 22 together in a friction fit or locked configuration. Thus, even without the retainer rotating on the receiver partial spherical seating surface, the shank can axially rotate with respect to the retainer and the receiver.

As described above, the split ring body 72 of the multi-planar retainer 70 further includes a partial spherical outer surface 74 having a radius that is substantially equal to the radius of the upper partial spherical surface 28 and the lower partial spherical surface 38 of the universal shank head 22, so as to form a substantially spherical united universal shank head 22/multi-planar retainer 70 structure when the resilient open pivoting multi-planar retainer 70 is captured or secured within the capture recess 32. The substantially spherical shape of the united universal shank head 22/multi-planar retainer 70 structure can be seen in the perspective cut-away view of FIG. 69 showing the fully assembled and locked pivotal bone anchor assembly. For example, with the embodiment of the multi-planar pivotal bone anchor assembly 10 illustrated in the drawings, the spherical shape of the united universal shank head 22/multi-planar retainer 70 structure is broken only at the top by the top annular surface 26 of the shank head and in the mid section by the upper and lower cylindrical surfaces 30, 36 of the universal shank head 22. Nevertheless, it is foreseen that other shapes and configurations for the interior and exterior surfaces of the multi-planar resilient open pivoting retainer 70, different from those shown in the drawings while providing for similar interaction and functionality of the various components of the pivotal bone anchor assembly, are also possible and considered to fall within the scope of the present disclosure.

Figure 24:
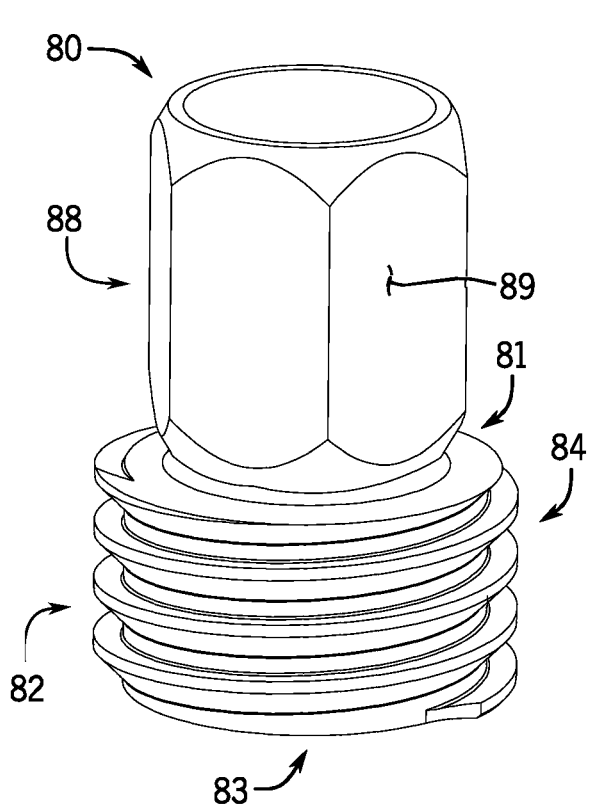
FIG. 24 is a perspective view of the closure of the multi-planar pivotal bone anchor assembly of FIG. 1.
Figure 25:
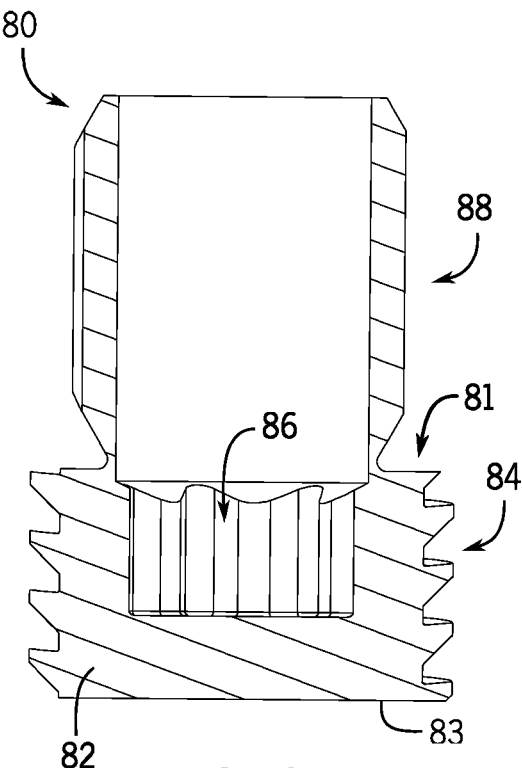
FIG. 25 is a cross-sectional side view of the closure of FIG. 24.

With particular reference to FIGS. 24-25, the closure 80 comprises a generally cylindrical closure body 82 having an outer continuous guide and advancement structure 84 formed into the outer side surface of the body 82, and which operably joins with the guide and advancement structure 116 formed into the interior face 110 of the receiver arms 104. In one aspect the guide and advancement structures 84, 116 can be helically wound flanges with splay-resisting or splay-controlling flange profiles for operably guiding under rotation and advancing the closure structure 80 downward between the arms 104 and having such a nature as to resist or control the splaying of the arms 104 when the closure structure 80 is advanced into the receiver channel 106. In other aspects the guide and advancement structures 84, 116 may take on a variety of alternative forms, including but not limited to a buttress thread, a square thread, a reverse angle thread, or other thread like or non-thread like helically wound advancement structure. The closure body 82 can also include a substantially planar bottom surface 83 below the guide and advancement structure 84 for directly engaging a top surface portion of the elongate rod.

Also shown in the drawings, a break-off tab 88 can be attached the upper end 81 of the closure body 82 and extend upwardly away therefrom to provide an external tool engagement structure 89 that can be used for rotatably advancing the closure downward between the arms 104 of the multi-planar receiver 100. In one aspect the break-off tab 88 can be designed to allow the tab 88 to break from the closure body 82 at a preselected torque, for example, 60 to 140 inch pounds.

Below and surrounded by the break-off tab 88, the upper end 81 of the closure 80 can further include an internal tool engagement structure, such as internal drive socket 86, which extends downward or inward into the closure body 82. The internal drive socket 86 can be used for closure removal. Similar to the internal drive socket formed into the shank head, the internal socket 86 of the illustrated closure 80 is an aperture formed in the upper end 81 and has a hex shape designed to receive a hex tool (not shown) of an Allen wrench type, into the aperture for rotating and driving the closure body 82. It will be appreciated that the internal tool engagement structure, in the alternative, may take a variety of tool-engaging forms, and may include one or more apertures of various shapes, such as a pair of spaced apart apertures or a multi-lobular or star-shaped aperture, such as those sold under the trademark TORX, or the like. It is further foreseen that closures having other shapes, configurations, and thread forms, different from those shown in the drawings while providing for similar interaction and functionality of the various components of the pivotal bone anchor assembly, are also possible and considered to fall within the scope of the present disclosure.

Figure 26:
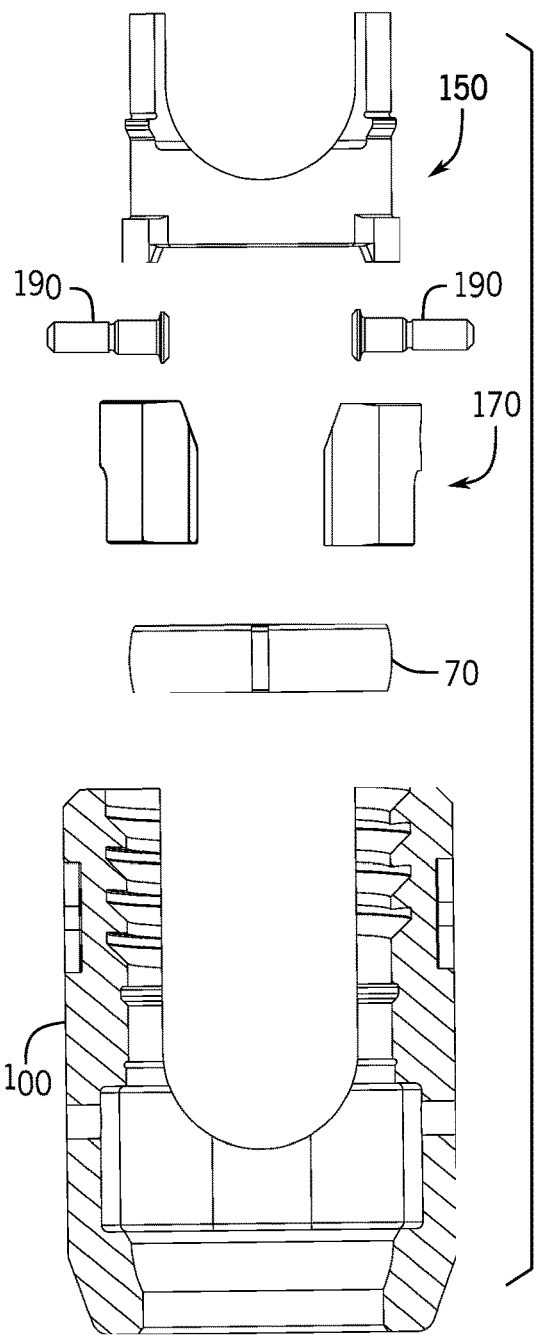
FIG. 26 is an exploded side view of the components of the multi-planar receiver sub-assembly prior to their pre-assembly into a shipping configuration.

With reference to FIG. 26, the multi-planar receiver 100, the multi-planar positioner 170 and positioner pins 180, the multi-planar retainer 70, and the pressure insert 150 are generally assembled together into a receiver sub-assembly at a factory setting that includes tooling for holding, alignment and manipulation of the component pieces. In some circumstances, the shank 20 is also assembled with the receiver sub-assembly at the factory. In other instances, it is desirable to first implant the shank 20, followed by addition of the pre-assembled receiver sub-assembly at the insertion point (see, e.g., FIGS. 45-46). In this way, the surgeon may advantageously and more easily implant and manipulate the shanks 20, distract or compress the vertebrae with the shanks and work around the shank upper portions or shank heads without the cooperating receivers being in the way. In other instances, it is desirable for the surgical staff to pre-assemble a shank of a desired size and/or variety (e.g., having a cannulated shank body, different thread patterns on the shank body, and/or hydroxyapatite on the shank body 40), with the receiver sub-assembly prior to implantation of the shank 20 into a patient's vertebra. Allowing the surgeon to choose the appropriately sized, type, or treated shank 20 advantageously reduces inventory requirements, thus reducing overall cost.

Figure 27:
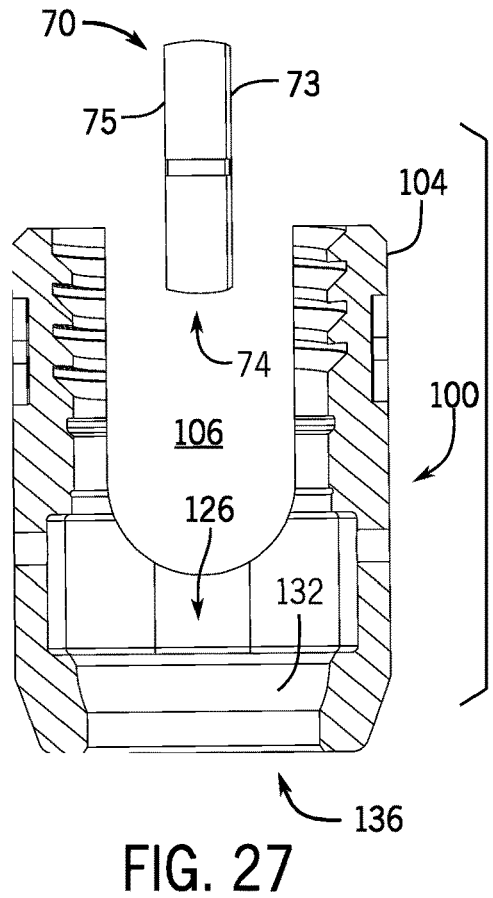
FIG. 27 is a partially cut-away side view of the multi-planar receiver of FIG. 26 with the multi-planar retainer being installed therein.
Figure 28:
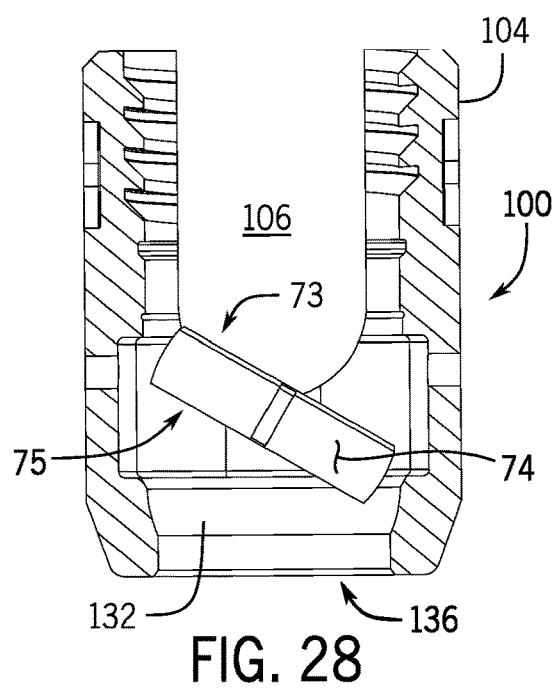
FIG. 28 is another partially cut-away side view of the multi-planar receiver of FIG. 26 with the multi-planar retainer being installed therein.
Figure 29:
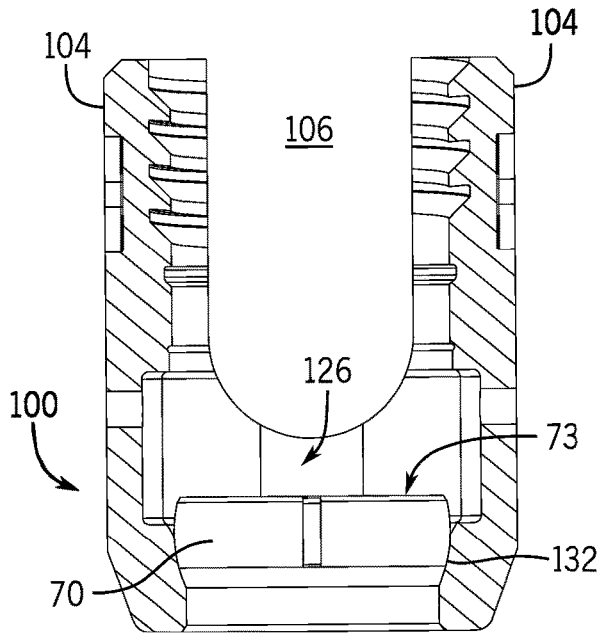
FIG. 29 is a partially cut-away side view of the multi-planar receiver of FIG. 26 with the multi-planar retainer installed therein.

The pre-assembly of the multi-planar receiver 100, the multi-planar two-piece positioner 170 and positioner pins 180, the multi-planar retainer 70, and the pressure insert 150 into a receiver sub-assembly 146 is shown in FIGS. 27-44. With particular reference to FIG. 27, first the retainer 70 is inserted into the receiver open channel 106 leading with the outer surface 74, with the retainer top surface 73 facing one arm 104 and the retainer bottom surface 75 facing the opposing arm 104. The retainer 70 is then lowered in such sideways manner, parallel with the receiver channel 106, through the channel 106 and into the receiver cavity 126 to the partial spherical seating surface 132 proximate the receiver bottom opening 136. The multi-planar retainer 70 is then rotated or allowed to rotate downward until its outer surface 74 rests against the receiver partial spherical seating surface 132, generally with the top surface 73 facing upwardly and the bottom surface 75 facing downwardly. (FIGS. 28-29).

Figure 30:
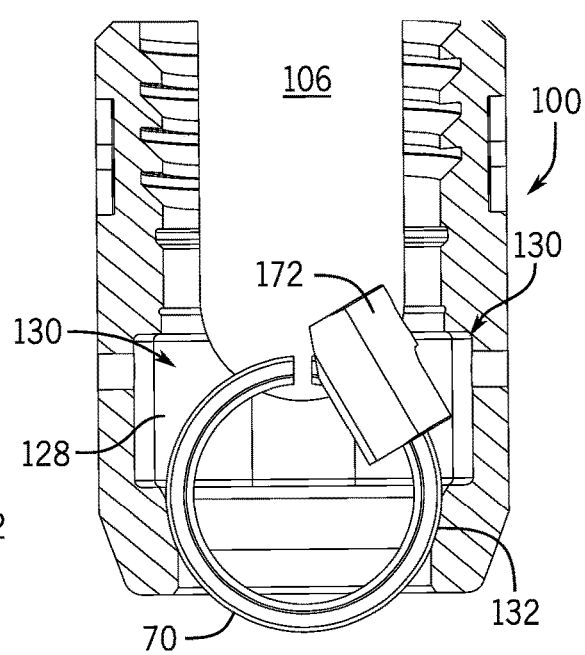
FIG. 30 is a partially cut-away side view of the multi-planar receiver with the installed multi-planar retainer and with a multi-planar positioner piece being installed therein.
Figure 31:
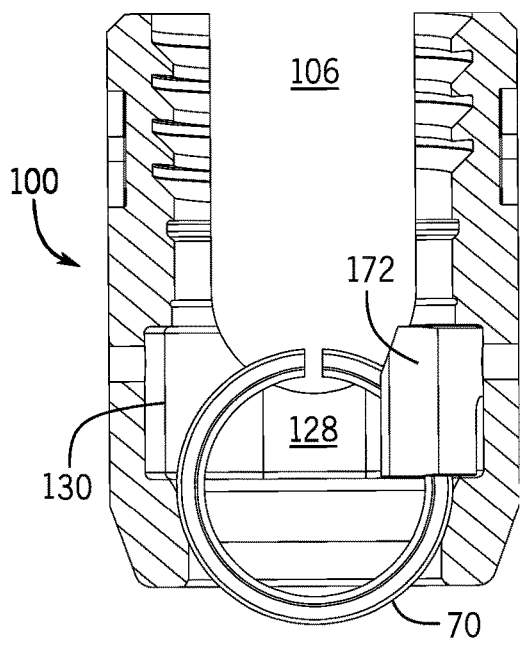
FIG. 31 is another partially cut-away side view of the multi-planar receiver with the installed multi-planar retainer and with the multi-planar positioner piece being installed therein.
Figure 32:
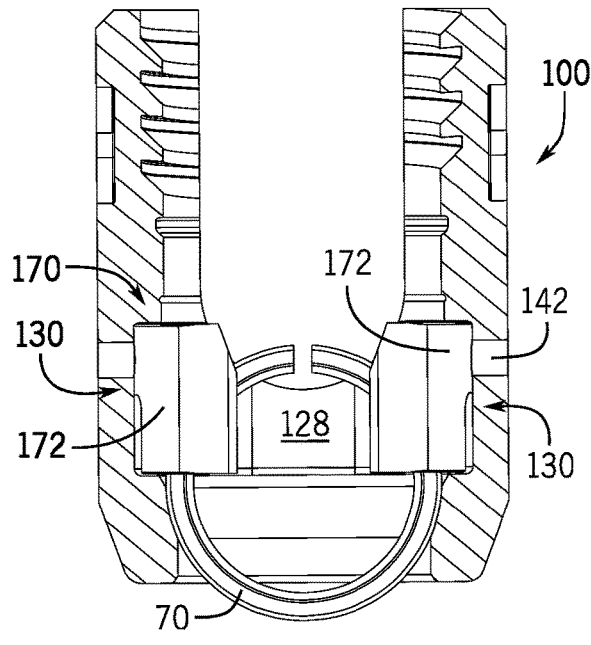
FIG. 32 is a partially cut-away side view of the multi-planar receiver with the multi-planar retainer and both multi-planar positioner pieces installed therein.
Figure 33:
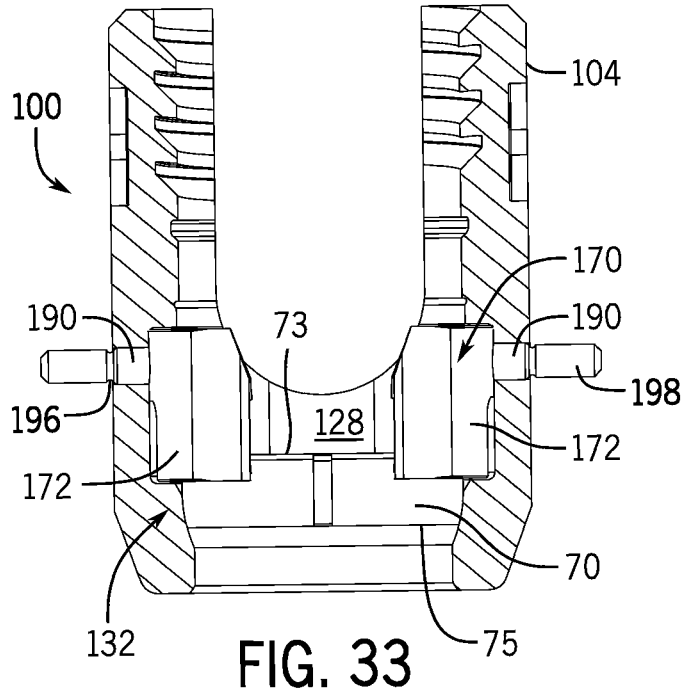
FIG. 33 is a partially cut-away side view of the multi-planar receiver with the multi-planar retainer, multi-planar positioner pieces, and positioner pins installed therein.
Figure 34:
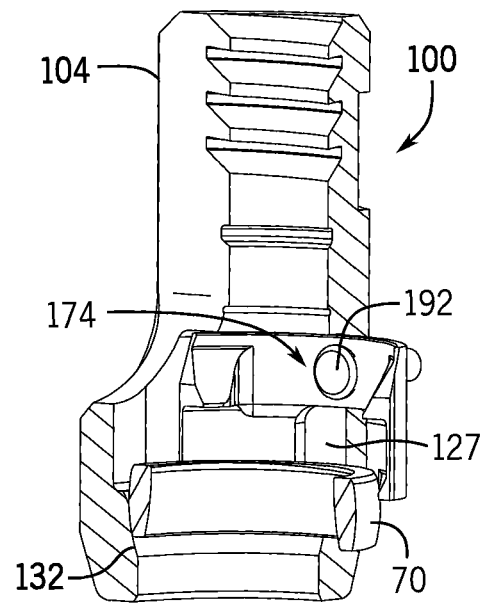
FIG. 34 is a sectioned perspective view of the multi-planar receiver, multi-planar retainer, multi-planar positioner pieces, and positioner pins of FIG. 33.
Figure 35:
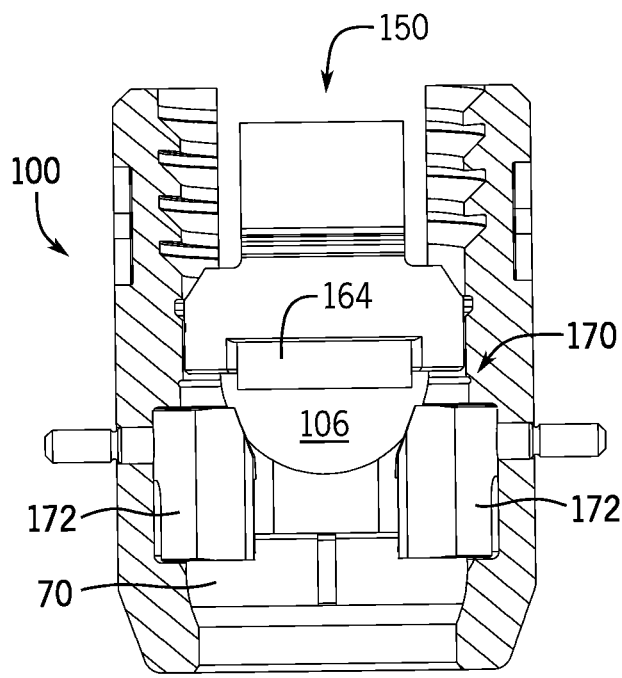
FIG. 35 is a partially cut-away side view of the multi-planar receiver with the installed multi-planar retainer, multi-planar positioner pieces, and positioner pins, and with the pressure insert now being installed therein.
Figure 36:
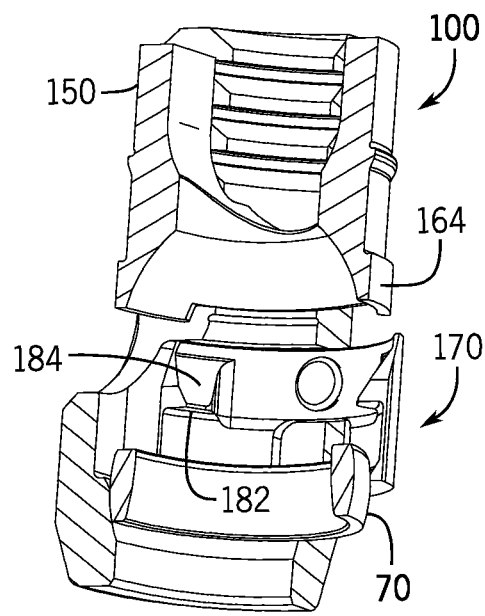
FIG. 36 is a sectioned perspective view of the multi-planar receiver, multi-planar retainer, multi-planar positioner pieces, positioner pins, and pressure insert of FIG. 35.

After reaching the receiver partial spherical seating surface 132, the multi-planar retainer 70 is then rotated back up into a vertical position, but one that is now perpendicular to the receiver channel 106. One at a time, each positioner piece 172 of the multi-planar two-piece positioner 170 is then downloaded around the upright retainer 70 and into one of the opposing end spaces 130 of the positioner chamber 128. (FIGS. 30-32). The multi-planar retainer 70 can then rotated back into the horizontal position resting against the receiver partial spherical seating surface 132, with the top surface 73 facing upwardly and the bottom surface 75 facing downwardly. Each multi-planar positioner piece 172 is then mounted or secured with the positioner chamber 128 by pressing a positioner pin 190 first through the upper pin aperture 176 in the center portion 174 of the positioner piece 172, and then into and through a positioner pin aperture 142 that extends through the sidewall of the positioner chamber 128 of the multi-planar receiver 100. (FIGS. 33-34). The end caps 192 of the positioner pins 190 will then engage the center portions 174 of the positioner pieces 172 to hold the center portions against the vertical sidewall surfaces 127 of the end spaces 130, thereby securing the positioner pieces 172 in place within the positioner chamber 128. Optionally, the break-off pin guide extensions 198 of the positioner pins 190 can now be sheared or broken off at the break-off groove 196.

With both the multi-planar retainer 70 and the two-piece multi-planar positioner 170 now in their initial respective pre-loaded positions, the pressure insert 150 can be positioned above the multi-planar receiver 100 and rotated until the opposing insert skirts 164 become aligned with the receiver channel 106. The pressure insert 150 is then moved downwardly through the receiver channel 106 toward the positioner 170 (FIGS. 35-36) until the bottom edges 167 of the skirts 164 rest against the ramp surfaces 184 of the upper flanges 182 of the positioner pieces 172 (FIGS. 37-38). In this intermediate position the insert ridges 158 projecting outward from the insert arms 152 may be located slightly above the upper receiver grooves 120 formed into the discontinuous cylindrical surface 118 of the interior face 110 of the receiver arms 104.

The pressure insert 150 can then be pushed downwardly to expand the wing portions 180 of the multi-planar positioner pieces 172 outwardly toward the vertical sidewall surfaces 127 of the end spaces 130 and to align the insert ridges 158 with the upper receiver grooves 120. The insert 150 is then rotated around the receiver central longitudinal axis until the insert ridges 158 begin to slide into the upper receiver grooves 120 and the opposing insert skirts 164 begin to slide under the non-annular upper step surface 125 that defines the top of the positioner chamber 128. (FIGS. 39-40). The rotation of the insert continues until the opposing insert skirts 164 slide off the ramp surfaces 184 of the upper positioner flanges 182 and clock into position adjacent the center portions 174 of the positioner pieces 172, allowing the positioner wing portions 180 to snap back and lock the insert skirts 164 against further rotation with the inside surfaces of the upper positioner flanges 182. (FIGS. 41-42). In this position the leading edges 187 (FIG. 19) of the lower positioner flanges 186 abut the outer surface 74 of the multi-planar retainer 70, generally above the hemisphere line of the partial spherical surface 74. The insert ridges 158 are also fully enclosed within the upper receiver grooves 120 to prevent further vertical movement of the pressure insert 150 until pressed downward with a deployment tool.

In a final pre-assembly step the multi-planar retainer 70 is pushed upward toward the pressure insert 150, causing the positioner wing portions 180 to again flex outward while allowing the leading lower edges 187 to slide downward over and off the retainer partial spherical surface outer surface 74. This allows the angled lower retainer capture surfaces 188 (FIG. 19) of the lower positioner flanges 186 to engage the bottom edge of the retainer outer surface 74 while the wing portions 180 of the positioner pieces 172 snap back with a spring force determined by the positioner center portions 174. The resulting interaction drives the retainer 70 upward against the upper retainer capture surfaces 185 of the upper flanges 182 so as to fully to capture the retainer between the upper retainer capture surfaces 185 and the lower retainer capture surfaces 188 of the lower flanges 186, as shown in FIGS. 43-44.

The multi-planar receiver 100, the two-piece multi-planar positioner 170 and positioner pins 180, the multi-planar retainer 70, and the pressure insert 150 are now pre-assembled into the receiver sub-assembly 146 shown in FIGS. 43-44 and 45-46. If the break-off pin guide extensions 198 of the positioner pins 190 have not yet been sheared or broken off at the break-off groove 196, this action may be performed after pre-assembly is complete to leave the receiver sub-assembly 146 with a smooth outer surface suitable for storage, shipping, and eventually use in a surgical setting.

The multi-planar receiver sub-assembly 146 is now in its shipping configuration, in which the multi-planar retainer 70 is securely supported and maintained within the positioner chamber portion 128 of the receiver cavity 126 by the two-piece multi-planar positioner 170, with the retainer 70 being centralized and controlled in space above both the receiver bottom opening 136 and the partial spherical seating surface 132. In the shipping configuration the pressure insert 150 is also held in its vertical position within the receiver central bore 114 by the insert ridges 158 being fully enclosed with the receiver upper grooves 120 that are sized and shaped to prevent any upward movement of the pressure insert 150 relative to the multi-planar receiver 100, and to allow for downward movement or deployment of the pressure insert 150 only with considerable direct force that may be provided by the appropriate tooling. Furthermore, in the shipping configuration the pressure insert 150 is also held or 'clocked' in angular position by the inner surfaces of the upper flanges 182 that project inwardly from the positioner wing portions 180 to surround the opposing skirts 164 that project outwardly from the insert base 162.

Illustrated in FIGS. 45-69 is the assembly or coupling of the pre-assembled receiver sub-assembly 146 of the multi-planar pivotal bone anchor assembly 10 to a universal shank head 22 that optionally may have a horizontal capture recess 32 that is protected with the removable capture recess protection sleeve 50 described above. It will be understood that the capture recess protection sleeve 50 may be removed from the shank head 22 either prior to installing the sub-assembly 146 over the shank head 22 or during the installation of the sub-assembly 146 to the shank head 22, as shown below.

Figure 45:
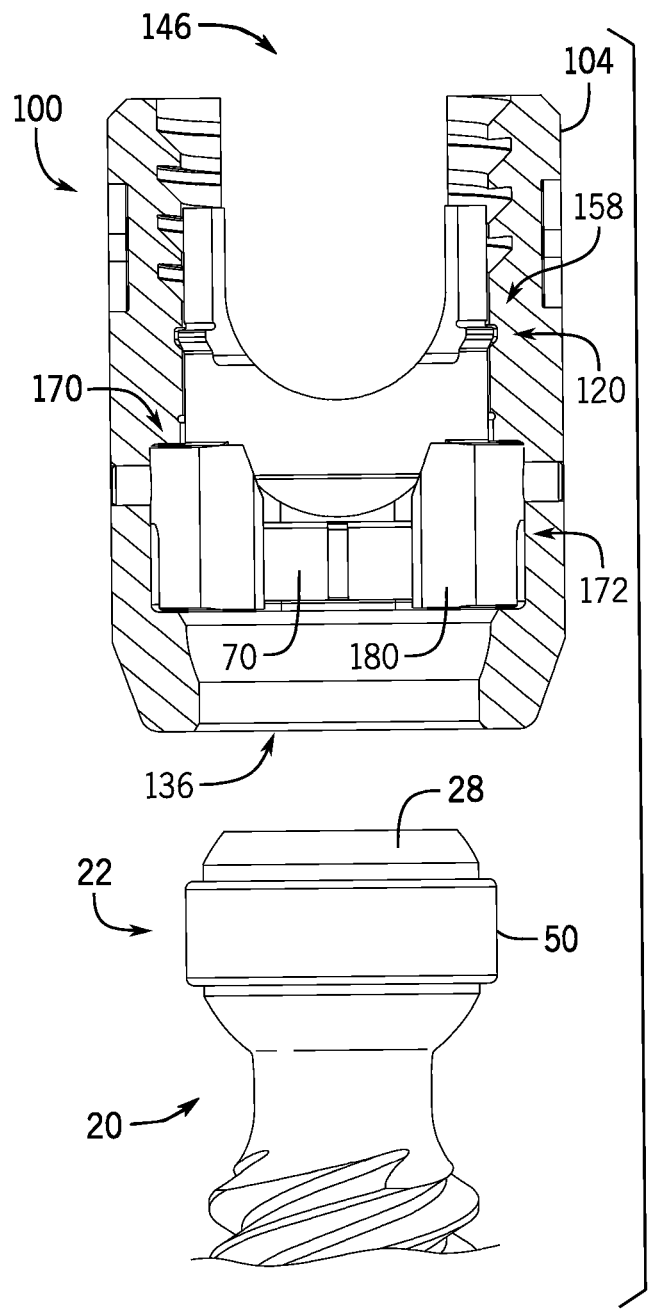
FIG. 45 is a partially cut-away side view of the multi-planar receiver sub-assembly positioned above the universal shank head of a bone anchor with an attached capture recess protection sleeve.
Figure 46:
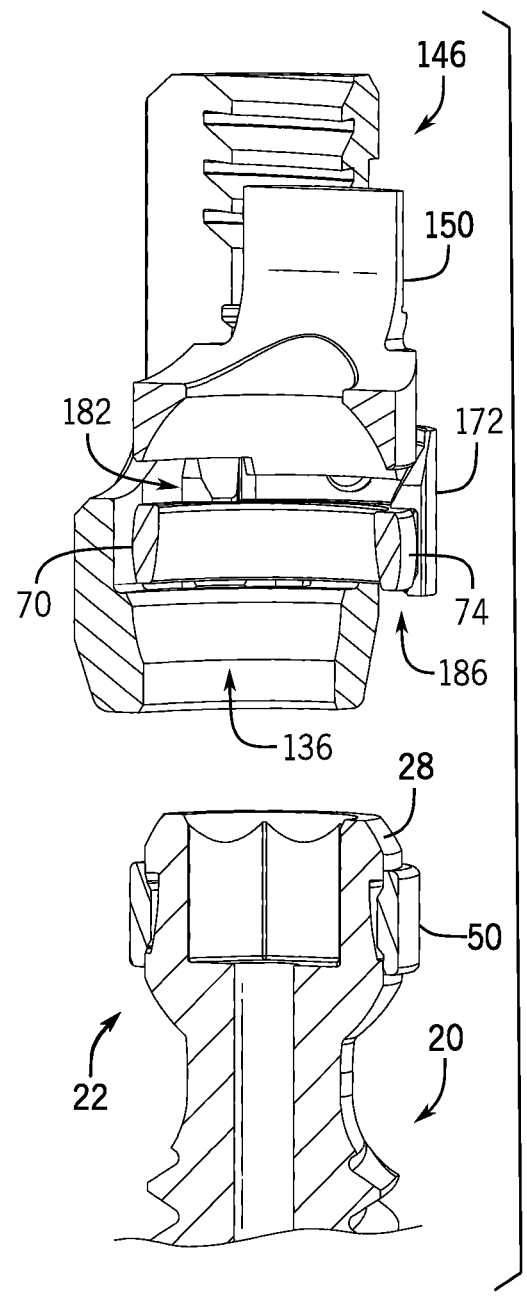
FIG. 46 is a sectioned perspective view of the multi-planar receiver sub-assembly and bone anchor of FIG. 45.

With reference first to FIGS. 45-46, the pre-assembled multi-planar receiver sub-assembly 146 is positioned above the universal shank head 22, with the receiver bottom opening 136 generally aligned with the shank head upper partial spherical surface 28.

Figure 47:
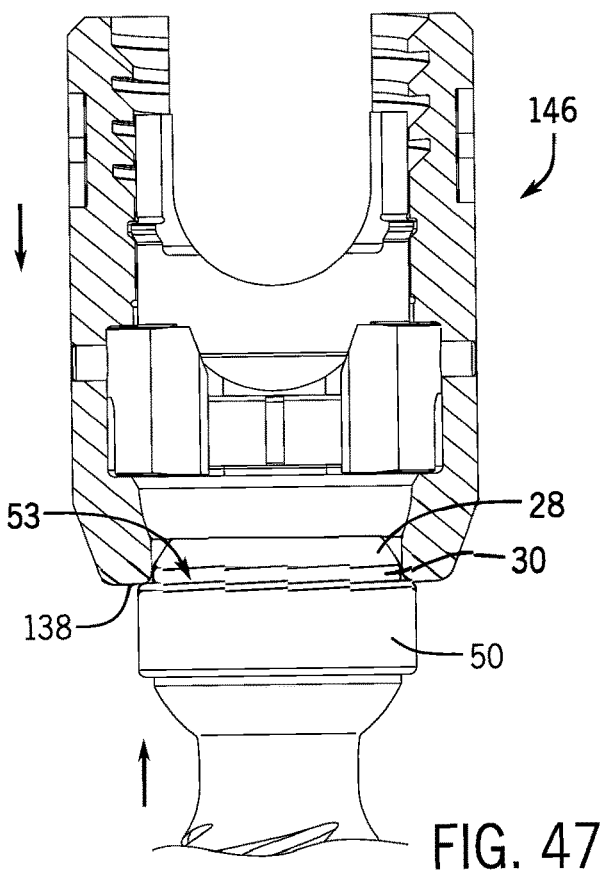
FIG. 47 is a partially cut-away side view of the multi-planar receiver sub-assembly moving downward to contact the universal shank head of the bone anchor and the top surface of the capture recess protection sleeve.
Figure 48:
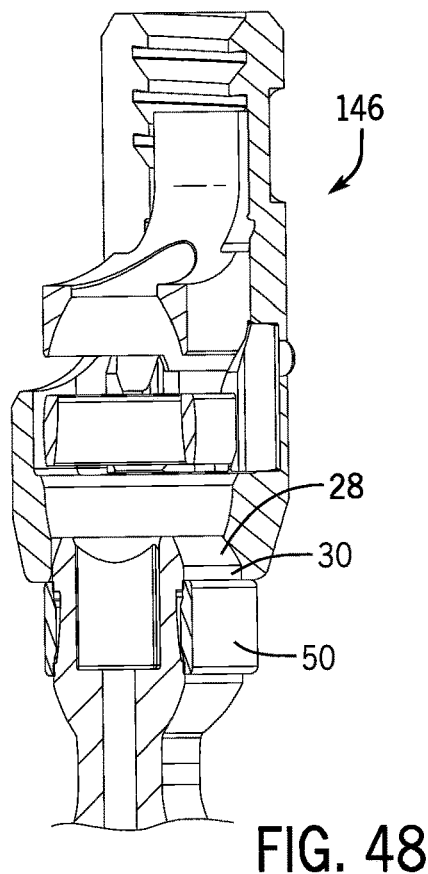
FIG. 48 is a sectioned perspective view of the multi-planar receiver sub-assembly and bone anchor of FIG. 47.

With reference to FIGS. 47-48, the multi-planar receiver sub-assembly 146 is then dropped until the upper partial spherical surface 28 and the upper cylindrical outer surface 30 of the universal shank head 22 enter the receiver bottom opening 36. At this point the receiver bottom surface 138 also abuts the top surface 53 of the capture recess protection sleeve 50.

Figure 49:
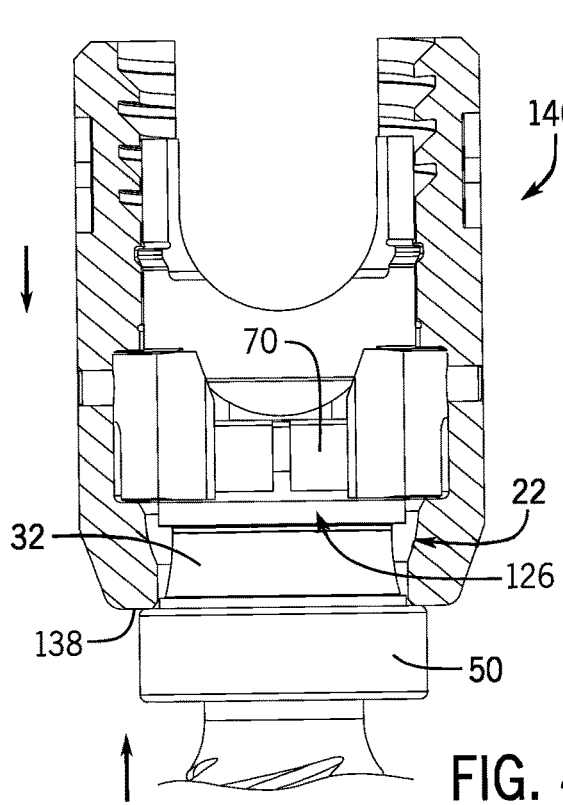
FIG. 49 is a partially cut-away side view of the multi-planar receiver sub-assembly moving further downward until the constrained multi-planar retainer contacts the universal shank head and the capture recess protection sleeve is pushed off the universal shank head.
Figure 50:
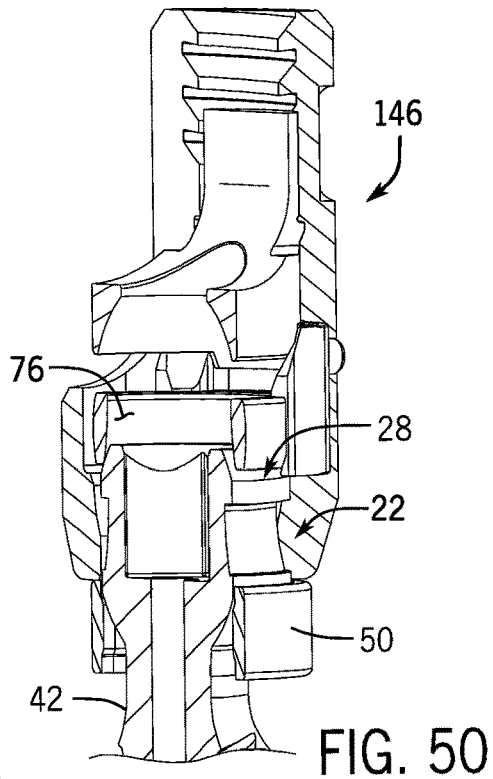
FIG. 50 is a sectioned perspective view of the multi-planar receiver sub-assembly and universal shank head of FIG. 49.
Figure 55:
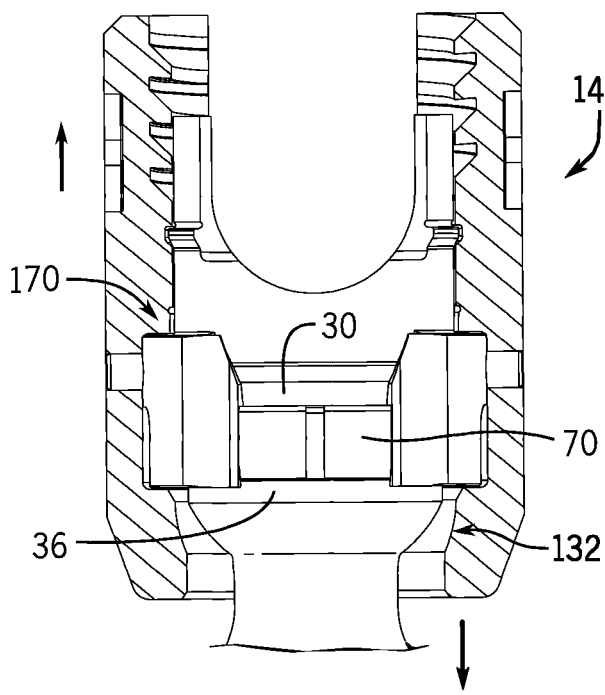
FIG. 55 is a partially cut-away side view of the multi-planar receiver sub-assembly moving back upward until the multi-planar retainer is captured within the horizontal capture recess of the universal shank head.
Figure 56:
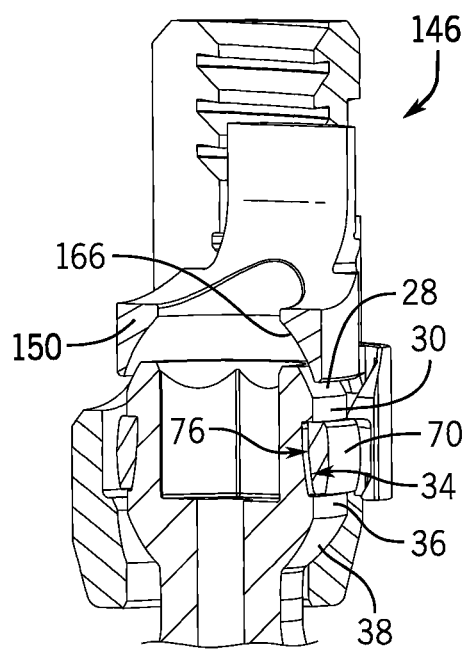
FIG. 56 is a sectioned perspective view of the multi-planar receiver sub-assembly and universal shank head of FIG. 55.

With reference to FIGS. 49-50, the multi-planar receiver sub-assembly 146 is further moved or pushed downward (or the universal shank head 22 is moved upward, depending on the frame of reference of the reader) until the shank head upper partial spherical surface 28 contacts the inner surface 76 of the multi-planar retainer 70. At the same time the capture recess protection sleeve 50 can be pushed downward off the universal shank head 22 to the neck region 42 of the bone anchor, exposing the capture recess 32 only after it has entered the receiver cavity 126 through the bottom opening 136. At this point the capture recess protection sleeve 50 can be entirely removed from the multi-planar assembly 10.

With reference to FIGS. 51-52, the multi-planar receiver sub-assembly 146 continues downward (or the universal shank head 22 upward) so that first the shank head upper partial spherical surface 28, and then the shank upper cylindrical outer surface 30, bears against the curvate inner surface 76 of the multi-planar retainer 70, causing the expansion of both the retainer 70 and its supporting multi-planar positioner 170 until the retainer 70 reaches maximum expansion with a narrowest diameter of the curvate inner surface 76 bearing against the shank upper cylindrical outer surface 30.

With reference to FIGS. 53-54, the multi-planar receiver sub-assembly 146 then continues downward (or the universal shank head 22 upward) until the shank head 22 reaches max push-through in which the shank head upper partial spherical surface 28 abuts the concave bottom surface 166 of the pressure insert 150 and the retainer curvate inner surface 76 bears against the shank lower cylindrical outer surface 36.

With reference to FIGS. 55-66, the multi-planar receiver sub-assembly 146 is then pulled or moved back upward (or the universal shank head 22 back downward) until the multi-planar retainer 70 snaps into and is captured by the horizontal capture recess 32, with the retainer curvate inner surface 76 engaged with the outwardly-facing inner recess surface 34 of the shank head 22.

Figure 57:
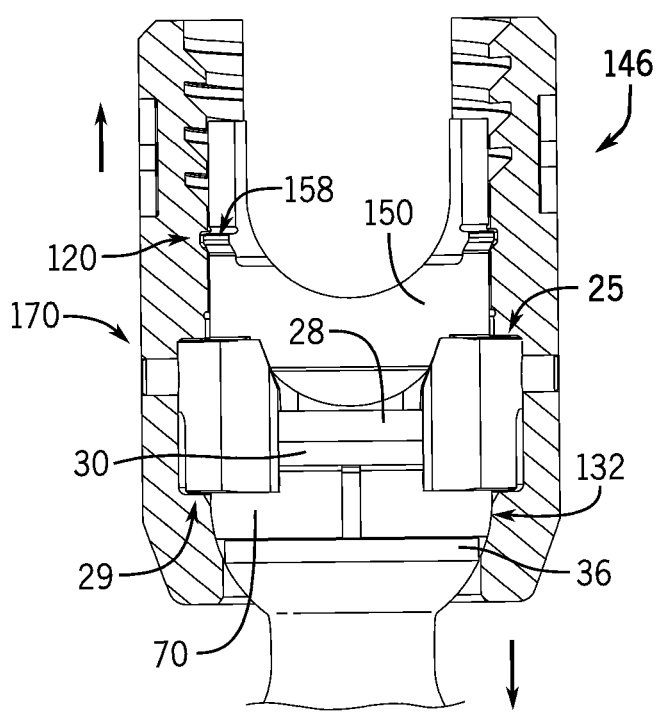
FIG. 57 is a partially cut-away side view of the multi-planar receiver sub-assembly moving further back upward until the multi-planar retainer becomes seated on the receiver partial spherical seating surface.
Figure 58:
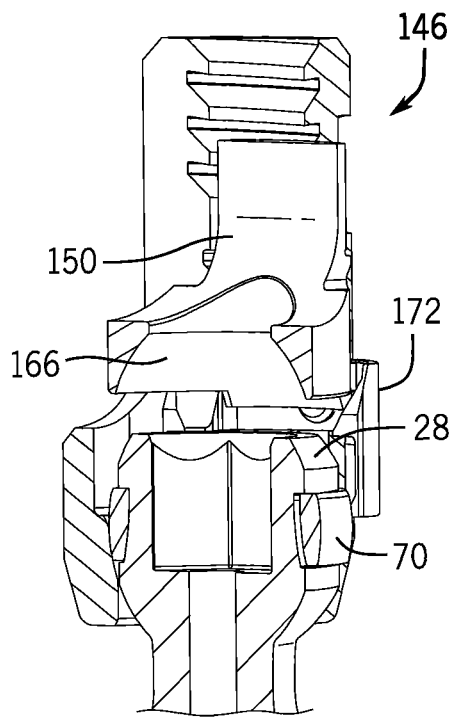
FIG. 58 is a sectioned perspective view of the multi-planar receiver sub-assembly and universal shank head of FIG. 57.

With reference to FIGS. 57-58, the multi-planar receiver sub-assembly 146 then continues back upward (or the universal shank head 22 back downward) while the multi-planar retainer 70 disengages from the multi-planar positioner 70 (which is vertically constrained by the upper and lower step surfaces 25, 29 of the positioner chamber 128) and becomes seated on the 360° continuous partial spherical seating surface 132 of the multi-planar receiver 100.

With reference to FIGS. 59-60, the pressure insert 150 can now be downwardly deployed with tooling to a non-floppy friction fit. For example, a deployment tool can be applied to the upper curvate rod seating surface 156 to push the insert ridges 158 downward out of the upper receiver grooves 20 and onto the discontinuous cylindrical surface 118 of the central bore 114 of the receiver, where the ridges 158 encounter an interference fit that resists the downward motion. In one aspect the force required to initially move the pressure insert and to overcome this interference fit can be about 200 pounds-force or greater. This action can temporarily cause the upwardly-projecting arms 152 of the pressure insert 150 to deflect inward, closing the gap at the top of the insert channel 154. With the pressure insert 150 in this partially-deployed position, a skilled artisan would recognize that the elongate rod may not fit within the insert channel 154.

Additional details and disclosure regarding deployment tools or tooling for preparing, assembling, and/or deploying bone screws and pivotal bone anchor assemblies or components thereof during spinal surgery, including the receiver sub-assembly and the bone anchor or shank having a universal shank head described above, can be found in co-pending Patent Cooperation Treaty (PCT) Application PCT/US2019/051190, filed the same day as the present application on Sep. 13, 2019, and claiming the benefit of U.S. Provisional Application No. 62/731,059, filed Sep. 13, 2018, with each of the above-referenced applications being incorporated by reference in its entirety herein and for all purposes.

Figure 63:
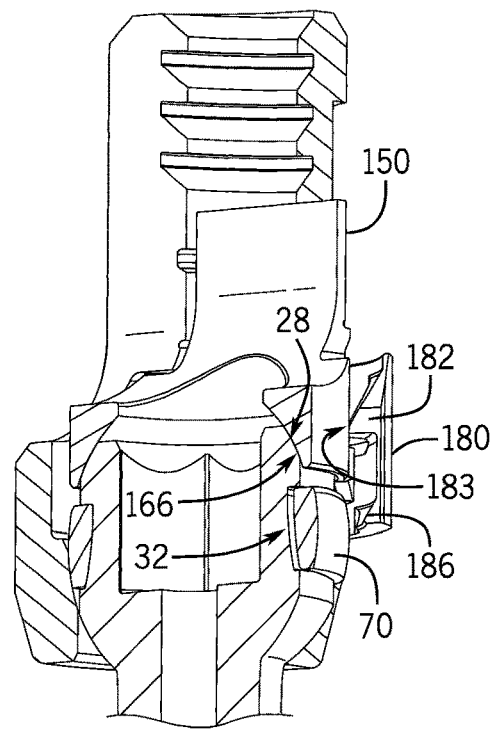
FIG. 63 is a partially cut-way and sectioned perspective view of the multi-planar receiver sub-assembly and universal shank head of FIG. 61.
Figure 64:
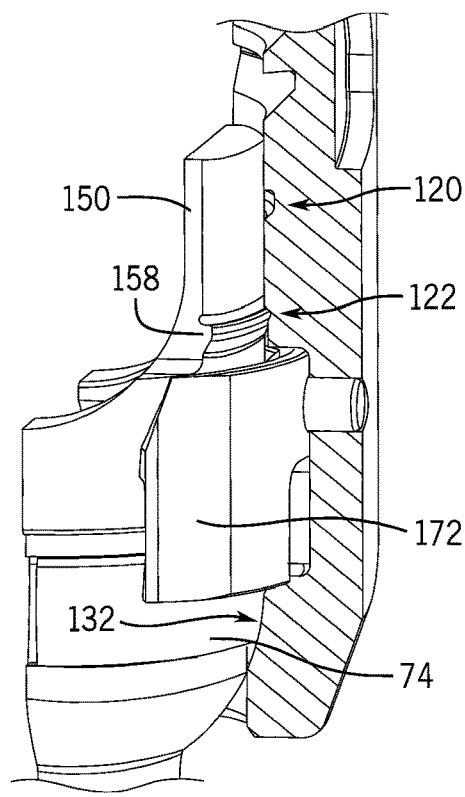
FIG. 64 is another partially cut-way and sectioned perspective view of the multi-planar receiver sub-assembly and universal shank head of FIG. 61.

With reference to FIGS. 61-64, the downward driving of the pressure insert 150 with the deployment tool can continue until the insert ridges 158 snap into the lower receiver grooves 122, at which point the insert concave spherical bottom surface 166 also fully engages the shank head upper partial spherical surface 28 and the retainer outer partial spherical surface 74 also fully engages the receiver partial spherical seating surface 132 to establish a friction fit. The friction fit firmly holds the multi-planar receiver 100 to the universal shank head 22 while allowing for movement of the receiver 100 relative to the bone anchor 20 with an applied force. Furthermore, with the pressure insert 150 in the deployed position, the leading edges 183 (FIG. 19) of the upper flanges 182 of the multi-planar positioner piece 172 can abut the cylindrical outer surface of the insert base 162 to hold the positioner piece 172 in an expanded position with the lower flanges 186 well-spaced from the now-pivotable multi-planar retainer 70 and universal shank head 22. (FIGS. 63-64).

Figure 65:
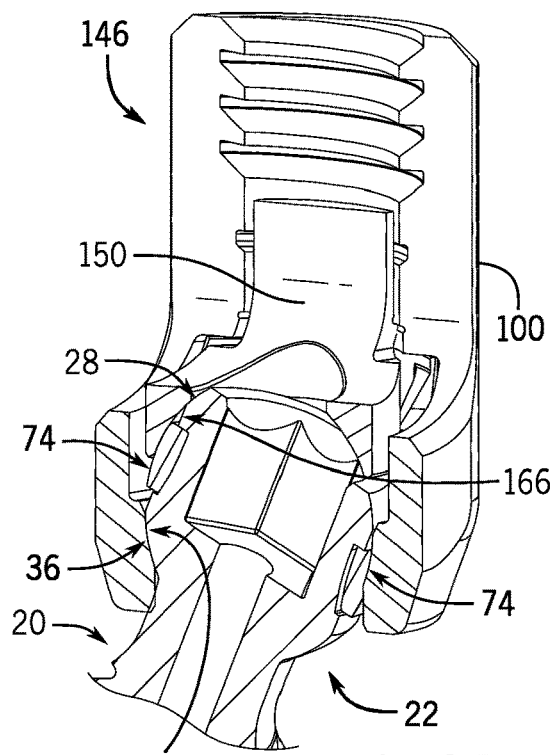
FIG. 65 is a partially cut-away and sectioned perspective view of the multi-planar receiver sub-assembly and coupled universal shank head in a friction fit position, with the bone anchor being pivoted relative to the receiver.
Figure 66:
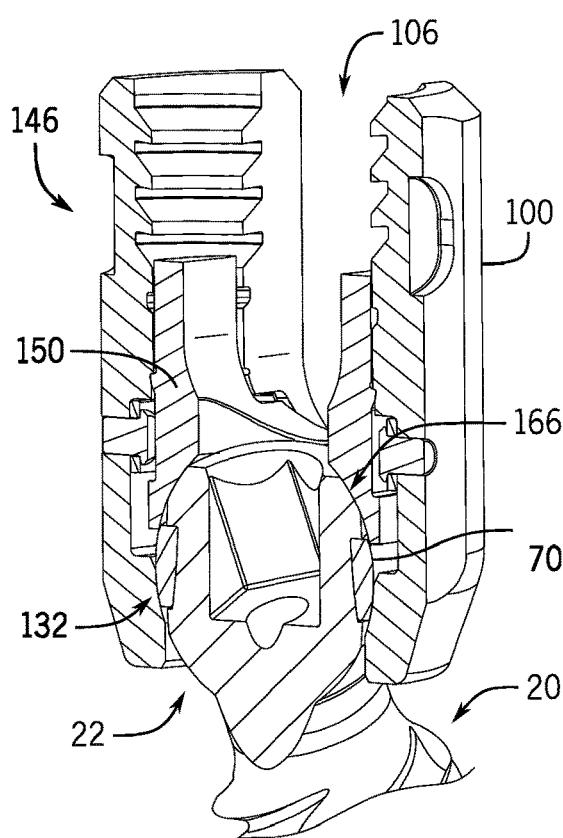
FIG. 66 is another partially cut-away and sectioned perspective view of the multi-planar receiver sub-assembly and coupled universal shank head of FIG. 65.

With reference to FIGS. 65-66, the friction fit engagement of the multi-planar receiver sub-assembly 146 to the bone anchor 20 can provide the surgeon or medical professional with a number of alignment options. For example, the friction fit allows for rotation of the multi-planar receiver 100 around the universal shank head 22, with an applied axial twisting force, as well as angulation of the receiver 100 relative the shank head 22, with an applied tangential moment force, so as to align the receiver channel 106 with the receiver channels of an adjacent bone anchor assembly.

The friction fit is provided from above by sliding frictional engagement between the insert concave spherical bottom surface 166 and the shank head upper partial spherical surface 28 and/or the retainer outer partial spherical surface 74, and from below by sliding frictional engagement between the receiver partial spherical seating surface 132 and the retainer outer partial spherical surface 74 and/or the shank head lower partial spherical surface 38.

Figure 67:
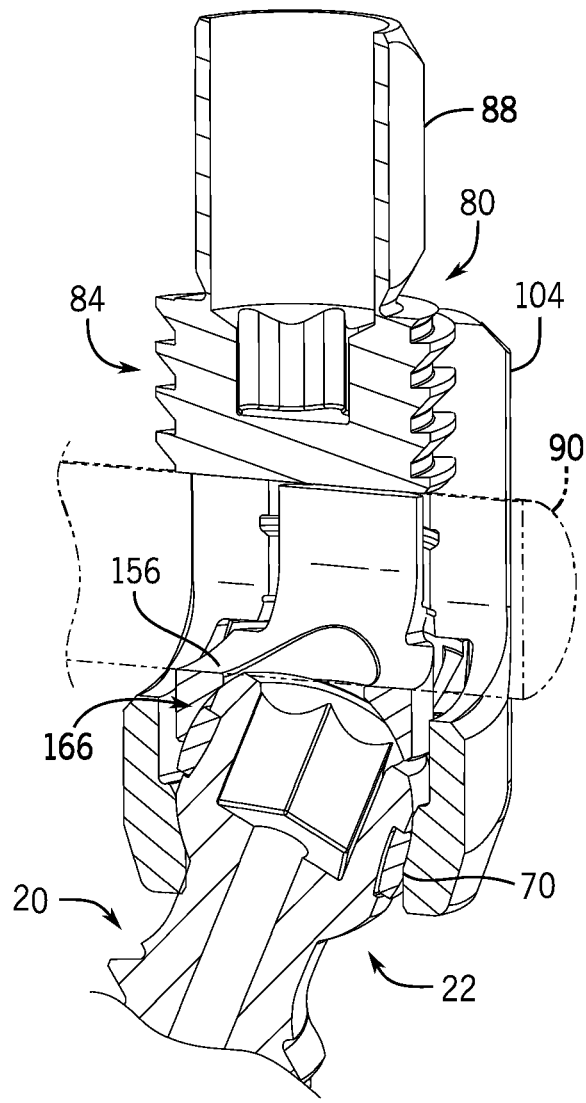
FIG. 67 is a partially cut-away and sectioned perspective view of the multi-planar receiver sub-assembly and coupled universal shank head, and further with an elongate rod and closure, in a partially locked configuration with the bone anchor being pivoted relative to the receiver.
Figure 68:
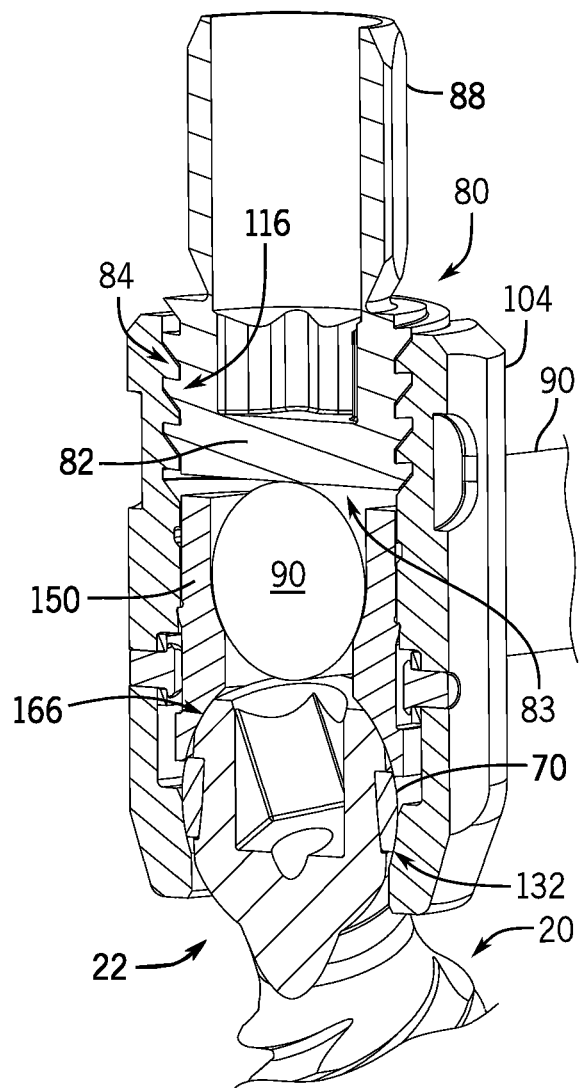
FIG. 68 is another partially cut-away and sectioned perspective view of the multi-planar receiver sub-assembly, coupled universal shank head, elongate rod, and closure of FIG. 67.

With reference to FIGS. 67-69, the full assembly of an elongate rod 90 and a closure 80 to the multi-planar receiver sub-assembly 46 may now be accomplished. First, after a desired alignment and/or positioning of the receiver sub-assembly 146 to the bone anchor 20 has been achieved, the elongate rod 90 can then be installed (i.e., reduced) into the receiver channel 106 until the underside surface of the rod 90 engages the upper curvate rod seating surface 156 of the insert channel 154. The closure 80 can then be installed into the upper portion of the receiver central bore 114, in which the continuous guide and advancement structure 84 of the closure body 82 engages the discontinuous guide and advancement structure 116 formed into the interior faces 110 of the receiver upright arms 104.

The closure 80 can be threaded downwardly until the bottom surface 83 of the closure body 82 engages a top surface of the elongate rod 90. Further rotation/torqueing of the closure 80 can then be used to drive the elongate rod 90 downward into the pressure insert 150, which in turn drives the universal shank head 22 and multi-planar retainer 70 downward into the receiver partial spherical seating surface 132 to achieve a final locking of the multi-planar pivotal bone anchor assembly 10, in which the receiver sub-assembly 146 can no longer move relative to the bone anchor 20.

With reference to FIG. 69, the closure break-off tab 88 can be sheared from the closure body 42 at a pre-determine torque value, thereby ensuring that the pivotal bone anchor assembly 10 is fully locked.

Figure 70:
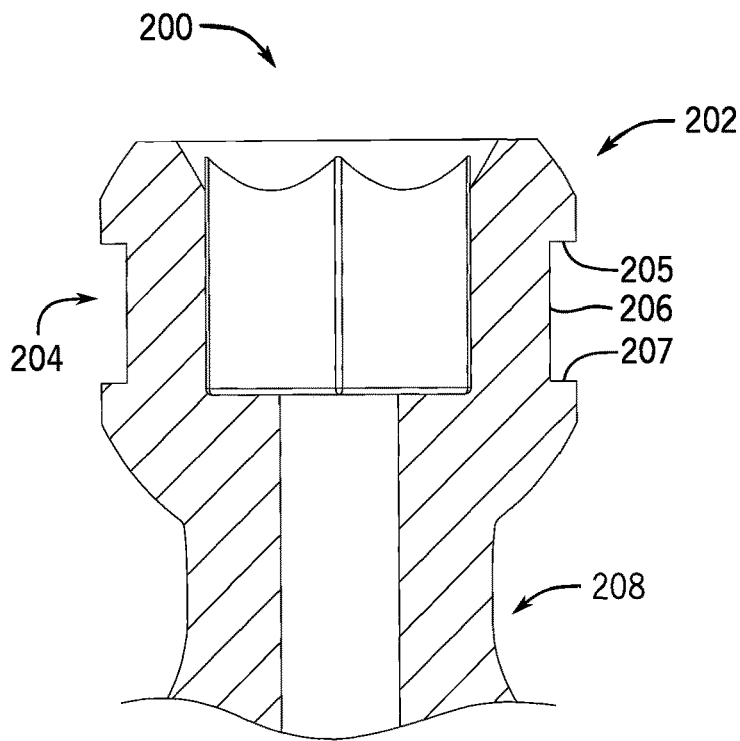
FIG. 70 is a cross-sectional side view of a universal shank head, in accordance with another representative embodiment of the disclosure.
Figure 71:
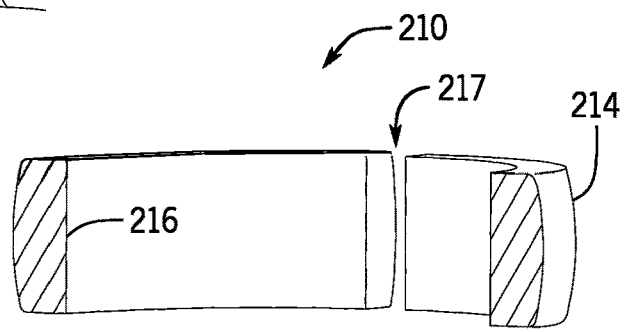
FIG. 71 is a cross-sectional side view of a retainer that is mateable with the universal shank head of FIG. 70.
Figure 72:
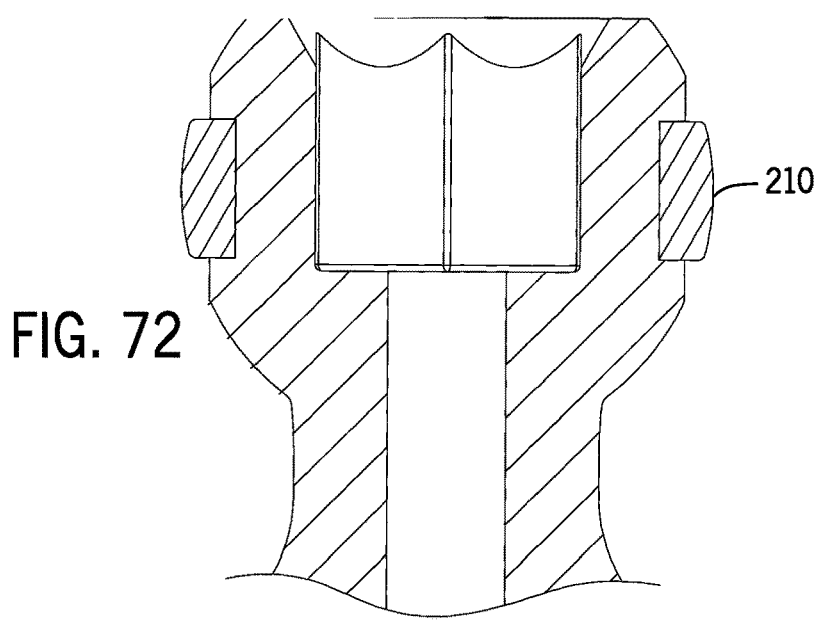
FIG. 72 is a cross-sectional side view of the coupled universal shank head and retainer of FIGS. 70 and 71.

As noted above, the outwardly-facing inner recess surface of the capture groove formed into the universal shank head can include any one of a variety of profiles that are different from that curved profile of the inner recess surface 34 illustrated in FIGS. 2-8. With brief reference to FIGS. 70-72, for example, in one alternative embodiment the bone anchor or shank 200 may have a universal shank head 202 with an upper ledge surface 205, a lower ledge surface 207, and an inner recess surface 206 that together define a circumferential horizontal capture recess 204, with the outwardly-facing inner recess surface 206 having a cylindrical profile. The capture recess 204 is therefore configured for engagement with a resilient open retainer, such as multi-planar retainer 210, having a split ring body 212 defining a central aperture 218 and having a slit or slot 217 formed therethrough, a partial spherical outer surface 214, and an inner surface 216 also having cylindrical profile to match the profile of the inner recess surface 206 of universal shank head 202.

Figure 73:
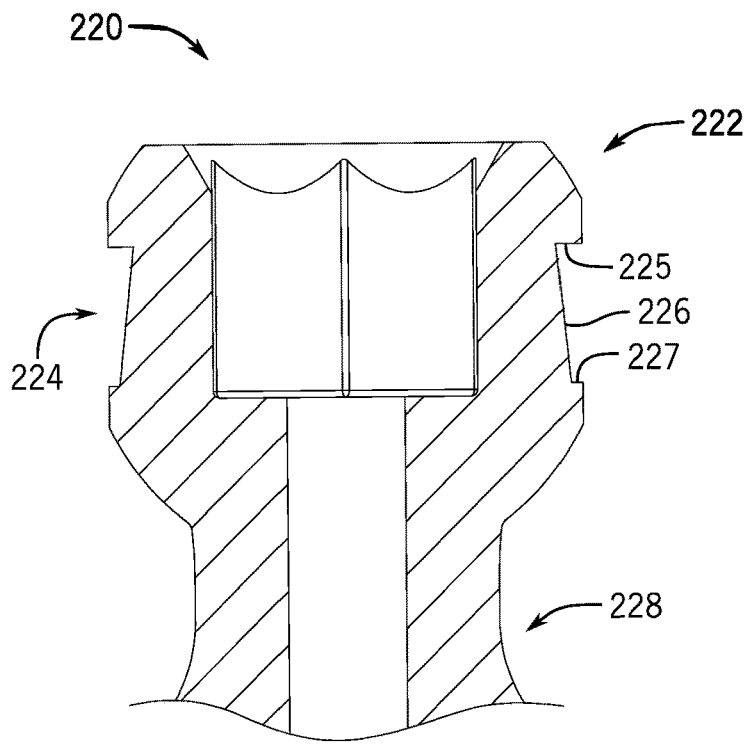
FIG. 73 is a cross-sectional side view of a universal shank head, in accordance with yet another representative embodiment of the disclosure.
Figure 74:
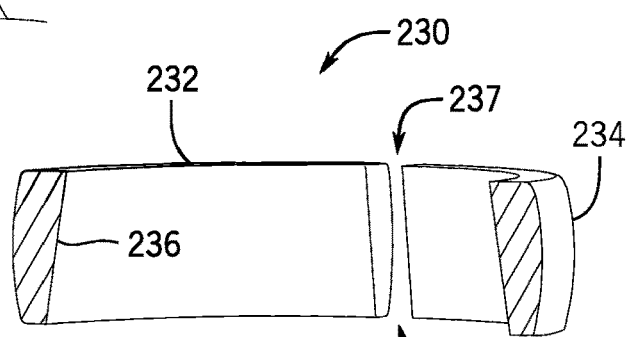
FIG. 74 is a cross-sectional side view of a retainer that is mateable with the universal shank head of FIG. 73.
Figure 75:
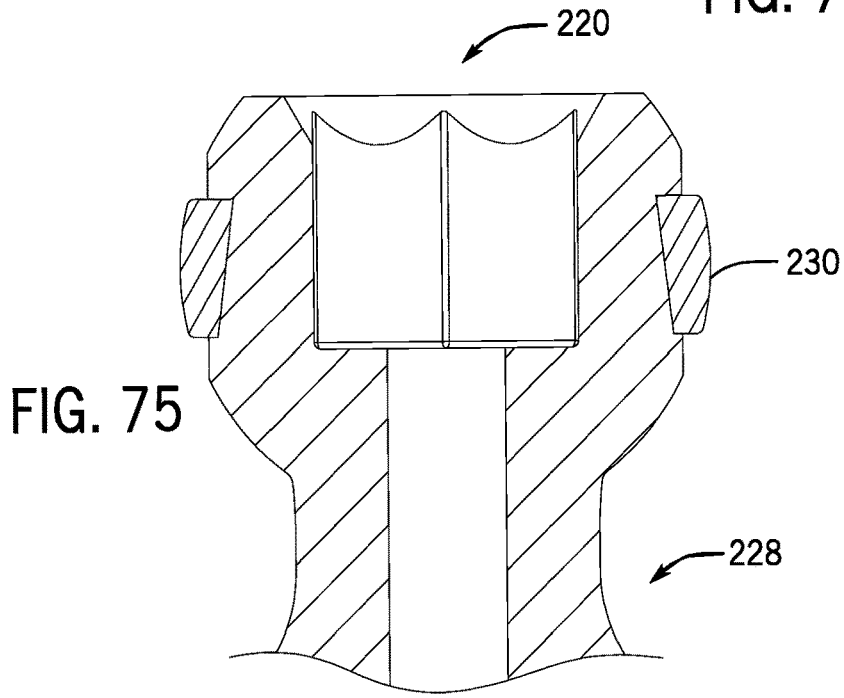
FIG. 75 is a cross-sectional side view of the coupled universal shank head and retainer of FIGS. 73 and 74.

Similarly, and with reference to FIGS. 73-75, for example, in yet another embodiment the bone anchor or shank 220 may have a universal shank head 222 with an upper ledge surface 225, a lower ledge surface 227, and an inner recess surface 226 that together define a circumferential horizontal capture recess 224, with the outwardly-facing inner recess surface 226 having a conical or frustoconical profile. The capture recess 224 is thus configured for engagement with a resilient open retainer, such as multi-planar retainer 230, having a split ring body 232 defining a central aperture 238 and having a slit or slot 237 formed therethrough, a partial spherical outer surface 234, and an inner surface 236 also having conical or frustoconical profile to match the profile of the inner recess surface 226 of universal shank head 222.

It is foreseen that other profile shapes and configurations for the complementary outwardly-facing inner recess surface of the universal shank head and the interior surface of the resilient open pivoting retainer (whether multi-planar or other) that are different from those shown in the drawings, while providing for similar interaction and functionality of the various components of the pivotal bone anchor assembly, are also possible and considered to fall within the scope of the present disclosure.

With reference now to FIG. 76, illustrated therein is another representative embodiment of the present disclosure, namely a uni-planar pivotal bone anchor apparatus or assembly 250 (hereinafter referenced to as "the uni-planar assembly 250") for securing an elongate rod to patient bone in spinal surgery. The uni-planar assembly 250 is similar to the multi-planar assembly 10 described above, but with modifications to the receiver, pivoting retainer, and positioner components that serve to restrict the motion of the shank 20 relative to the receiver 300 to a single plane.

In particular, the uni-planar assembly 250 can include the same bone anchor or shank 20 that is included in the multi-planar assembly 10, with the shank 20 having the universal shank head 22 at a proximal end and an anchor portion or shank body 40 extending distally from the shank head 22 for securement to patient bone. As previously described in reference to the multi-planar embodiment, the structure of the universal shank head 22 having the circumferential horizontal capture recess 32, as shown above in FIGS. 2-4, allows for the shank head 22 to connect with either a multi-planar or a uni-planar receiver sub-assembly, and in particular with either a multi-planar or a uni-planar retainer which is engageable with a complementary multi-planar or uni-planar pivoting receiver, respectively. This feature of the pivotal bone anchor assembly system can advantageously provide for selectable multi-planar or uni-planar motion of a receiver with respect to the universal shank head 22, as determined by a surgeon in an operating environment after implantation of the shank body 40 into a vertebra, but prior to the coupling or capture of the universal shank head 22 with a receiver sub-assembly.

As shown in FIG. 76, the uni-planar assembly 250 also includes a uni-planar receiver 300 having an internal cavity 326 in a base portion 334 and two upright arms 304 extending upwardly from the base portion 334 to define a rod channel 306 for receiving the elongate rod 90. The uni-planar receiver 300 can also be initially pivotably secured to the universal shank head 22 with a number of separate internal components that have been pre-assembled into the internal cavity 326 and the rod channel 306 to form a uni-planar receiver sub-assembly. These components can include a uni-planar resilient open retainer 270, a pressure insert 150 as previously described, and a uni-planar multi-piece positioner 370 that may be secured within the internal cavity 326 of the base portion 334 with positioner pins 390. After the elongate rod 90 has been positioned within a lower portion of the rod channel 306, the closure 80 as previously described can be threadably secured into an upper portion of the rod channel to apply pressure to an upper surface of the elongate rod 90, thereby locking both the elongate rod 90 and the uni-planar assembly 250 into a final locked position.

Also shown in FIG. 76, in one aspect the bone anchor or shank 220 of the uni-planar assembly 250 can include the optional removable resilient capture recess protection sleeve 50 installed within the horizontal capture recess 32 formed into the universal shank head 22, so as to prevent soft tissue and bone chips from entering and fouling the capture recess prior to introduction of the shank head 22 into the uni-planar receiver sub-assembly.

The uni-planar receiver 300 modified for use within the uni-planar assembly 250 is shown in FIGS. 77-78. The uni-planar receiver 300 is similar to the multi-planar receiver described above, having a base portion 334 defining and internal cavity 326 and two upright arms 304 extending upwardly from the base portion 334 to define a rod channel 306 for receiving the elongate rod 90. The internal cavity 326 of the uni-planar receiver 300 also includes an upper positioner chamber 328 configured to receive and secure the multi-piece or two-piece uni-planar positioner 370, and a lower seating surface 332 located proximate the bottom opening 336 and configured to slidably frictionally engage with the outer surface 274 of the uni-planar retainer 270 in the friction fit configuration described in more detail below.

The lower seating surface 332 is modified, however, to include two opposed recesses or pockets 333 for receiving a pair of rounded pegs 279 that project laterally outward from the uni-planar retainer's 270 outer surface 274 (FIGS. 79-80). The opposed pockets 333 are contoured with a rounded internal surface complementary with the rounded outer surface of the pegs 279, and also aligned relative to the non-continuous circumferential partial spherical lower seating surface 332. This provides for the retainer's non-continuous circumferential partial spherical outer surface 274 to fictionally slide over the receiver's non-continuous circumferential partial spherical lower seating surface 332 while the opposed rounded pegs 279 of the retainer 270 rotate or pivot within the opposed pockets 333 of the receiver cavity 326.

It is foreseen that other shapes and configurations for the interior and exterior surfaces of the uni-planar receiver 300, different from those shown in the drawings while providing for similar interaction and functionality of the various components of the pivotal bone anchor assembly, are also possible and considered to fall within the scope of the present disclosure.

The uni-planar retainer 270 modified for use within the uni-planar assembly 250 is shown in FIGS. 79-80. The uni-planar retainer 270 is similar to the multi-planar retainer described above, having a split ring body 272 defining a central aperture 278, and having a slot or slit 277 allows the ring body 272 to expand when pressure is applied to the inner surface 276, and then to contract back to its original shape when the pressure is released. The split ring body 272 has a top surface 273, a bottom surface 275, and a spacing between the top and bottom surface 273, 275 that allows the retainer 270 to snap in the capture recess 32, with the top surface 273 adjacent the upper ledge surface 33 and the bottom surface 275 adjacent the lower ledge surface 35, upon assembly within the universal shank head 22. As with the multi-planar embodiment, the diameter of the shaped inner surface 276 of the uni-planar retainer 270 can be substantially equal to the diameter of the shaped inner recess surface 34, so that the retainer inner surface 276 engages the recess inner surface 34 with a substantially neutral fit, with the ring body 272 being neither substantially compressed nor substantially expanded after coupling with the capture recess and subsequent engagement in a friction fit or fully locked configuration. The uni-planar retainer 270 is also dimensioned to be slidably rotatable within the horizontal capture recess 32 after the shank 20 and uni-planar retainer 270 are moved downward into contact with the partial spherical seating surface 332 of the uni-planar receiver 300, but prior to the loading of the retainer 270 and shank head 22 together in a friction fit or locked configuration.

As with the multi-planar embodiment, the split ring body 272 of the uni-planar retainer 270 includes a partial spherical outer surface 274 having a radius that is substantially equal to the radius of the upper partial spherical surface 28 and the lower partial spherical surface 38 of the shank head 22, so as to form a substantially spherical shank head 22/uni-planar retainer 270 structure when the resilient open retainer 270 is captured or secured within the capture recess 32. The split ring body 272 has been modified in the uni-planar embodiment, however, to include the two opposing rounded pegs 279 extending outward from the partial spherical outer surface 274 and configured for engagement within the opposed pockets 333 in the receiver cavity 326 of the uni-planar receiver 300. As described in more detail below, the engagement between the retainer pegs 279 with the receiver pockets 333 limits the pivoting motion of the shank 20 relative to the uni-planar receiver 300 to a single plane, with the axis of rotation being defined by the opposed retainer pegs 279.

Figure 124:
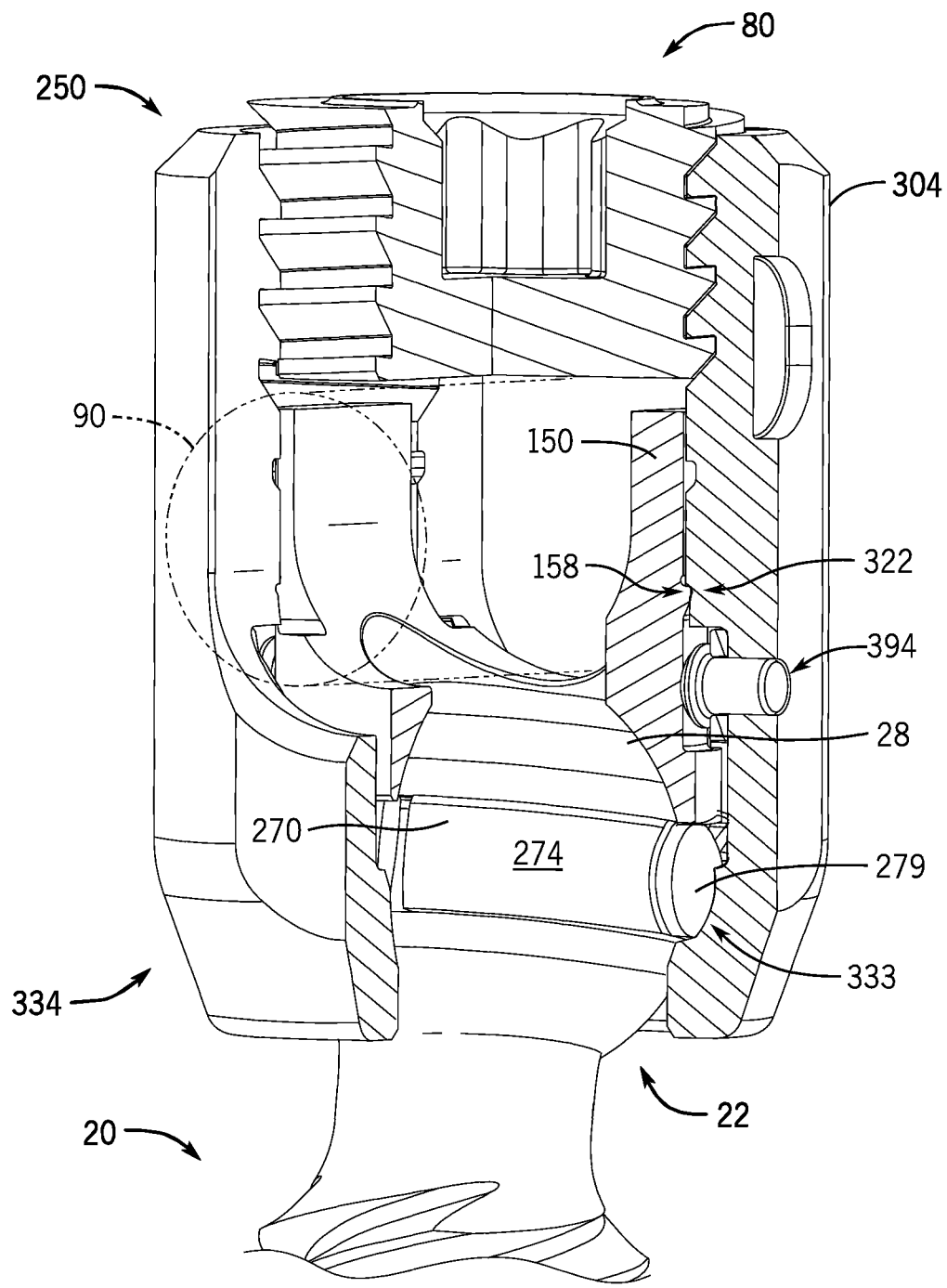

The substantially spherical shape of the united universal shank head 22/uni-planar retainer 270 structure can be seen in the perspective cut-away view of FIG. 124 showing the fully assembled and locked uni-planar pivotal bone anchor assembly 250. For example, the spherical shape of united shank head 22/uni-planar retainer 270 structure is broken only at the top by the top annular surface 26 of the shank head, in the mid section by the upper and lower cylindrical surfaces 30, 36 of the shank head 22, and on the sides by the outwardly-projecting rounded pegs 279 of the uni-planar retainer 270. Nevertheless, it is foreseen that other shapes and configurations for the interior and exterior surfaces of the uni-planar resilient open retainer 270, different from those shown in the drawings while providing for similar interaction and functionality of the various components of the pivotal bone anchor assembly, are also possible and considered to fall within the scope of the present disclosure The uni-planar two-piece positioner 370 modified for use within the uni-planar assembly 250 is shown in FIGS. 81-82. The uni-planar positioner 370 is similar to the multi-planar positioner 170 described above, comprising the two positioner pieces 372, with each positioner piece 372 having a center portion 374 with an upper pin aperture 376 that is used to pin the center portion 374 to the vertical sidewall surface 327 of the positioner chamber 326 with a positioner pin 390, as well as the lower cut-out window 378 below the center portion 374 to provide for greater flexure of the positioner piece. The lower cut-out window 378 has been modified in the uni-planar embodiment to accommodate the retainer pegs 279 during expansion of the uni-planar retainer 270.

As with the multi-planar embodiment, each positioner piece 372 further includes bendable outer wing portions 380 on either side of the center portion 374 that flex outwardly under load or pressure, and which then spring back inwardly when released. The wing portions 380 of the uni-planar embodiment also include upper flanges 382 and lower flanges 386 projecting inwardly from the inner faces of the outer wing portions 180 to define, among other features, an open discontinuous retainer capture chamber. It is foreseen that other shapes and configurations for the interior and exterior surfaces of the uni-planar two-piece positioner 370, different from those shown in the drawings while providing for similar interaction and functionality of the various components of the pivotal bone anchor assembly, are also possible and considered to fall within the scope of the present disclosure.

The pre-assembly of the uni-planar receiver 300, the uni-planar two-piece positioner 370 and positioner pins 380, the uni-planar retainer 270, and the pressure insert 150 into a uni-planar receiver sub-assembly is shown in FIGS. 83-97. With particular reference to FIG. 84, first the retainer 270 is inserted into the receiver open channel 306 leading with the outer surface 274, with the top surface 273 facing one arm 304 and the retainer bottom surface 275 facing the opposing arm 304. The retainer 270 is then lowered in such sideways manner, parallel with the receiver channel 306, through the channel 306 and into the receiver cavity 326 to the partial spherical seating surface 332 proximate the receiver bottom opening 336. The retainer 270 is then rotated or allowed to rotate downward until its outer surface 274 rests against the receiver partial spherical seating surface 332 and the opposed rounded pegs 279 of the uni-planar retainer 270 are received within the opposed pockets 333 formed into the seating surface 332 of the uni-planar receiver 300, and generally with the retainer top surface 273 facing upwardly and the bottom surface 275 facing downwardly. (FIGS. 85-86).

After reaching the receiver partial spherical seating surface 332, the uni-planar retainer 270 is then rotated on the opposed rounded pegs 279 back up into a vertical position, but one that is now perpendicular to the receiver channel 306. One at a time, each positioner piece 372 of the uni-planar two-piece positioner 370 is then downloaded around the upright retainer 270 and into one of the opposing end spaces 330 of the positioner chamber 328. (FIGS. 87-89). During the downloading of the positioner pieces 372 the opposed pegs 279 are received with the enlarged cut-out windows 378 formed into the center portions of each positioner piece of the uni-planar embodiment. As discussed above, the enlarged cut-out windows 378 (FIG. 82) are sized and shaped to provide clearance for the retainer pegs 279 during all subsequent steps in the pre-assembly of the components into the uni-planar receiver sub-assembly, as well as all subsequent mounting and deployment steps in coupling the uni-planar receiver sub-assembly to the universal shank head 22.

Figure 90:
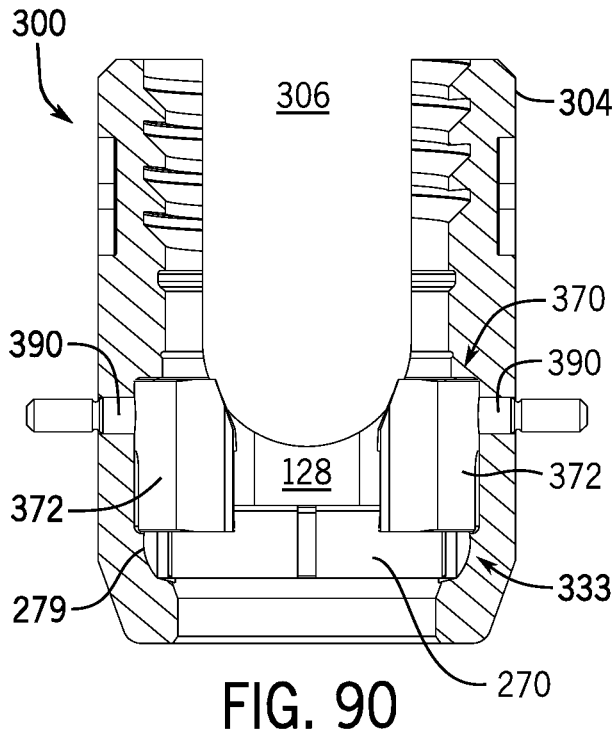
FIG. 90 is a partially cut-away side view of the uni-planar receiver with the uni-planar retainer, uni-planar positioner pieces, and positioner pins installed therein.
Figure 91:
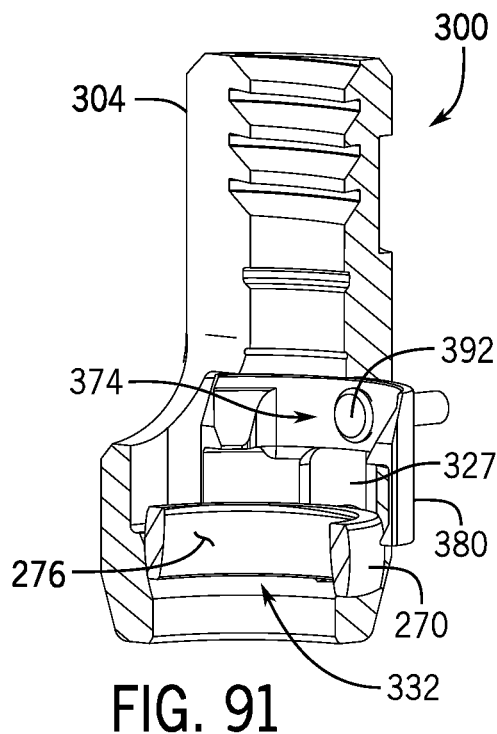
FIG. 91 is a sectioned perspective view of the uni-planar receiver, uni-planar retainer, uni-planar positioner pieces, and positioner pins of FIG. 90.
Figure 92:
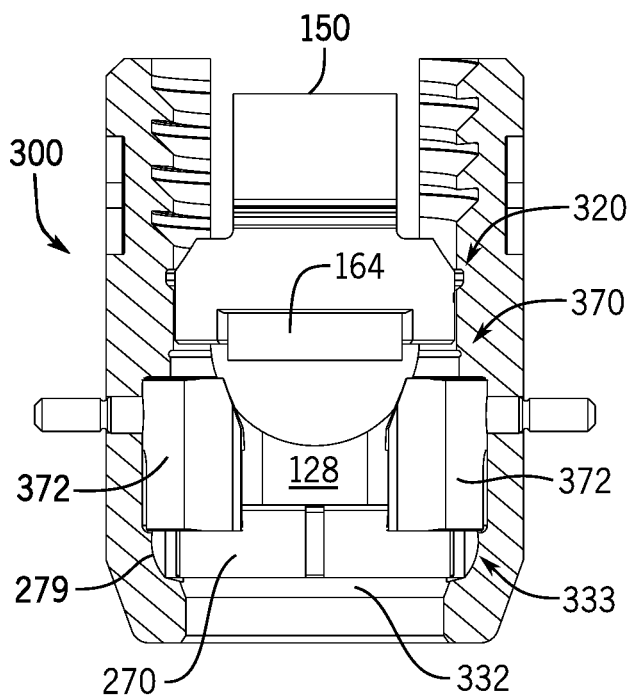
FIG. 92 is a partially cut-away side view of the uni-planar receiver with the installed uni-planar retainer, uni-planar positioner pieces, and positioner pins, and with the pressure insert now being installed therein.
Figure 93:
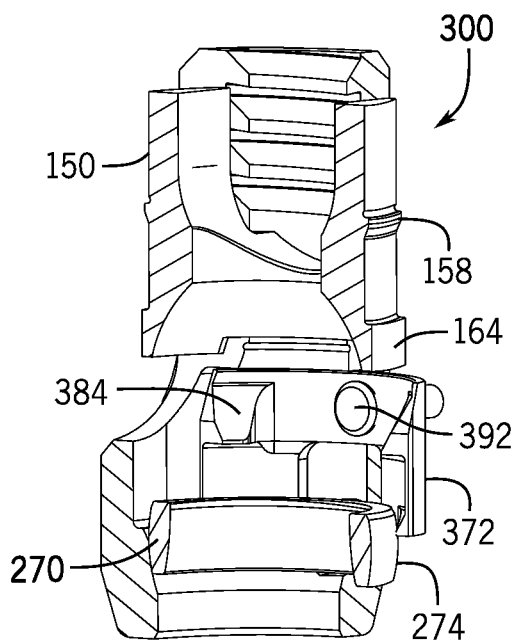
FIG. 93 is a sectioned perspective view of the uni-planar receiver, uni-planar retainer, uni-planar positioner pieces, positioner pins, and pressure insert of FIG. 92.

The uni-planar retainer 270 can then be rotated back into the horizontal position resting against the receiver partial spherical seating surface 332, with the top surface 273 facing upwardly and the bottom surface 275 facing downwardly. Each positioner piece 372 is then mounted or secured with the positioner chamber 328 by pressing a positioner pin 390 first through the upper pin aperture 376 in the center portion 374 of the positioner piece 372, and then into and through a positioner pin aperture 342 that extends through the sidewall of the positioner chamber 328 of the uni-planar receiver 300. (FIGS. 89-90). The end caps 392 of the positioner pins 390 will then engage the center portions 374 of the positioner pieces 372 to hold the center portions against the vertical sidewall surfaces 327 of the end spaces 330, thereby securing the positioner pieces 372 in place within the positioner chamber 328. Optionally, the break-off pin guide extensions 398 of the positioner pins 390 can now be sheared or broken off at the break-off groove 396.

Figure 94:
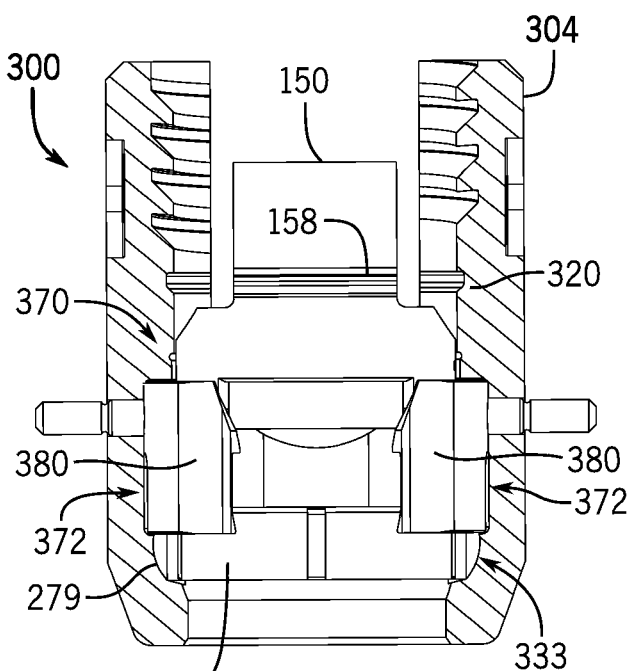
FIG. 94 is another partially cut-away side view of the uni-planar receiver with the installed uni-planar retainer, uni-planar positioner pieces, and positioner pins, and with the pressure insert now being installed therein.
Figure 95:
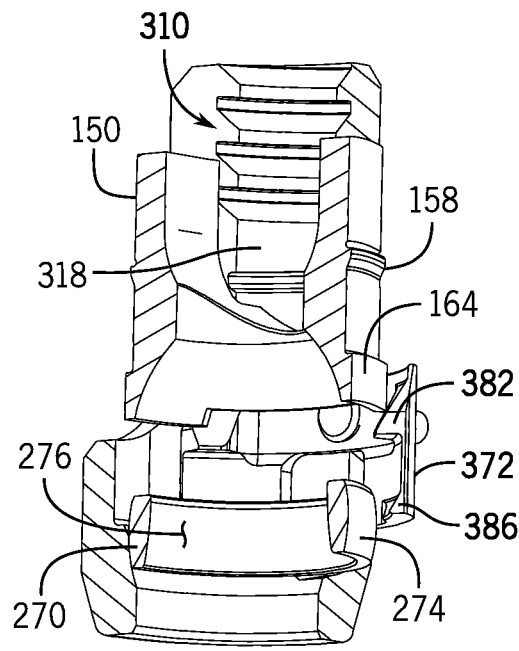
FIG. 95 is a sectioned perspective view of the uni-planar receiver, uni-planar retainer, uni-planar positioner pieces, positioner pins, and pressure insert of FIG. 94.

With both the uni-planar retainer 270 and the uni-planar two-piece positioner 370 now in their initial respective pre-loaded positions, the pressure insert 150 can be positioned above the multi-planar receiver 300 and rotated until the opposing insert skirts 164 become aligned with the receiver channel 306. The pressure insert 150 is then moved downwardly through the receiver channel 306 toward the positioner 370 (FIGS. 92-93), until the bottom edges 167 of the skirts 164 rest against the ramp surfaces 384 of the upper flanges 382 of the positioner pieces 372 (FIGS. 94-95). In this intermediate position the insert ridges 158 projecting outward from the insert arms 152 may be located slightly above the upper receiver grooves 320 formed into discontinuous cylindrical surface 318 of the interior face 310 of the insert arms 304.

Figure 96:
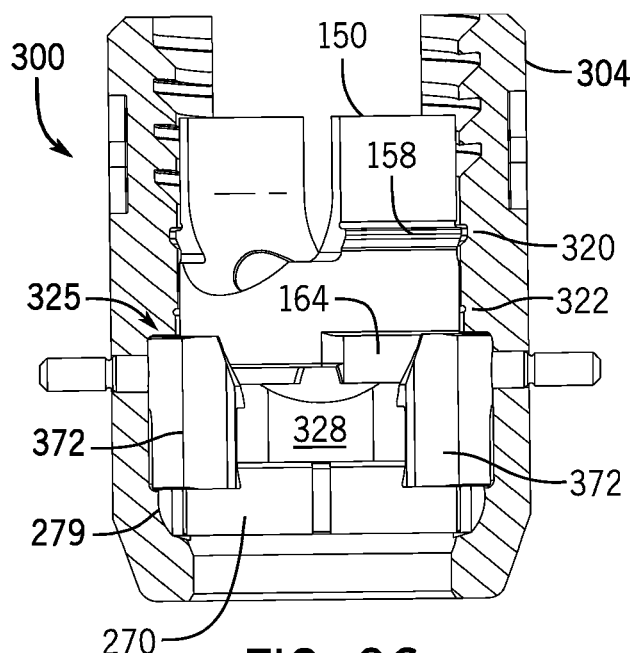
FIG. 96 is another partially cut-away side view of the uni-planar receiver with the installed uni-planar retainer, uni-planar positioner pieces, and positioner pins, and with the pressure insert being rotated therein.
Figure 97:
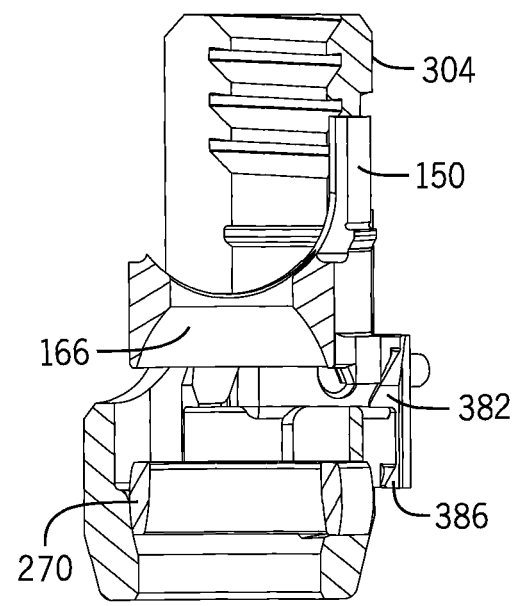
FIG. 97 is a sectioned perspective view of the uni-planar receiver, uni-planar retainer, uni-planar positioner pieces, positioner pins, and pressure insert of FIG. 96.
Figure 98:
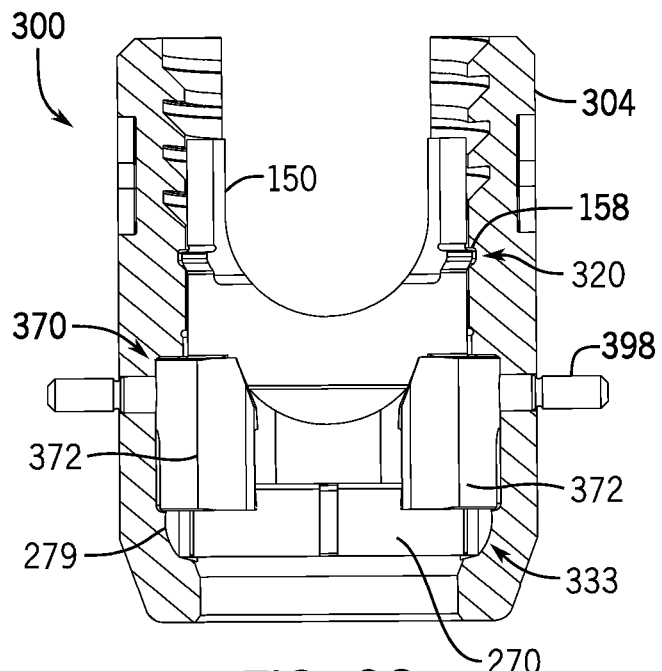
FIG. 98 is another partially cut-away side view of the uni-planar receiver with the installed uni-planar retainer, uni-planar positioner pieces, and positioner pins, and with the pressure insert being fully installed therein.
Figure 99:
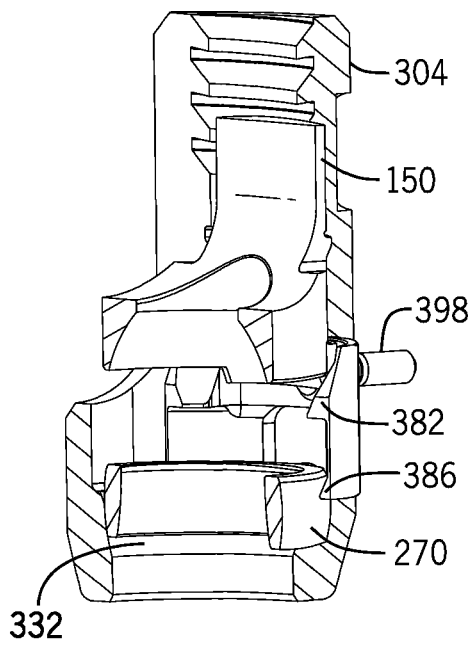
FIG. 99 is a sectioned perspective view of the uni-planar receiver, uni-planar retainer, uni-planar positioner pieces, positioner pins, and pressure insert of FIG. 98.

The pressure insert 150 can then be pushed downwardly to expand the wing portions 380 of the positioner pieces 372 outwardly toward the vertical sidewall surfaces 327 of the end spaces 330 and to align the insert ridges 158 with the upper receiver grooves 320. The insert 150 is then rotated around the receiver central longitudinal axis until the insert ridges 158 begin to slide into the upper receiver grooves 320 and the opposing insert skirts 364 begin to slide under the non-annular upper step surface 325 that defines the top of the positioner chamber 328. (FIGS. 96-97). The rotation of the pressure insert 150 continues until the opposing insert skirts 164 slide off the ramp surfaces 384 of the upper positioner flanges 382 and clock into position adjacent the center portions 374 of the positioner pieces 372, allowing the positioner wing portions 380 to snap back and lock the insert skirts 164 against further rotation with the inside surfaces of the upper positioner flanges 382. (FIGS. 98-99). In this position the leading edges 387 of the lower positioner flanges 386 abut the outer surface 274 of the retainer 270, generally above the hemisphere line of the partial spherical surface 274. The insert ridges 158 are also fully enclosed within the upper receiver grooves 320 to prevent further vertical movement of the pressure insert 150 until pressed downward with a deployment tool.

Figure 100:
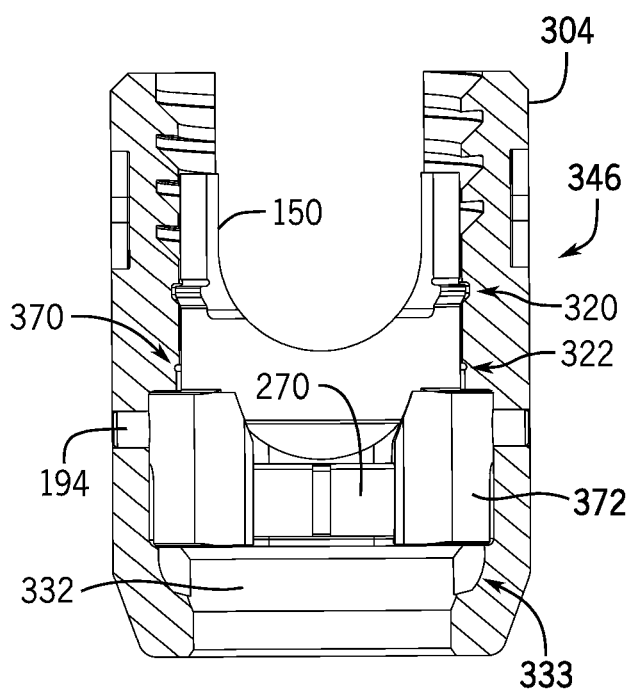
FIG. 100 is a partially cut-away side view of the uni-planar receiver together with the installed and positioned uni-planar retainer, uni-planar positioner pieces, positioner pins, and pressure insert forming a pre-assembled uni-planar receiver sub-assembly.
Figure 101:
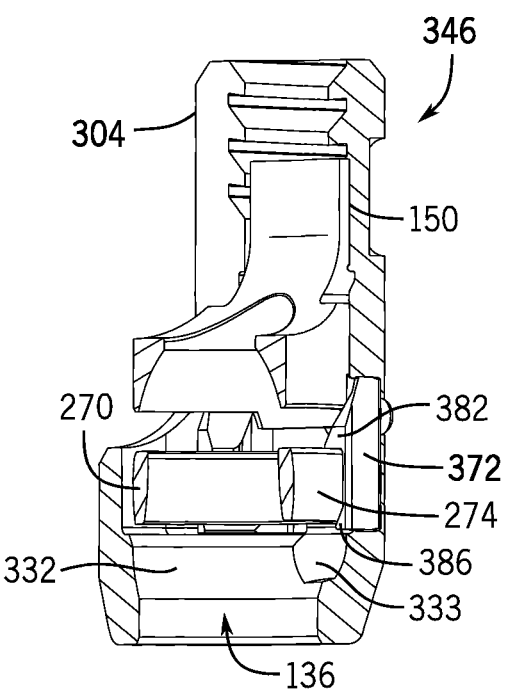
FIG. 101 is a sectioned perspective view of the pre-assembled uni-planar receiver sub-assembly of FIG. 100.

In a final pre-assembly step the uni-planar retainer 270 is pushed upward toward the pressure insert 150, causing the positioner wing portions 380 to again flex outward while allowing the leading lower edges 387 (FIG. 82) to slide downward over and off the retainer partial spherical surface outer surface 274. This allows the angled lower retainer capture surfaces 388 of the lower positioner flanges 386 to engage the bottom edge of the retainer outer surface 274 while the wing portions 380 of the positioner pieces 372 snap back with a spring force determined by the positioner center portions 374. The resulting interaction drives the retainer 270 upward against the upper retainer capture surfaces 385 of the upper flanges 382 so as to fully to capture the retainer between the upper retainer capture surfaces 385 and the lower retainer capture surfaces 388 of the lower flanges 386, as shown in FIGS. 100-101. During the upward movement of the retainer 270 the inner edges of the positioner piece cut-out windows 378 can operate to surround the outwardly projecting opposed pegs 279 of the uni-planar retainer 270 to maintain their alignment over the opposed pockets 333 formed into the seating surface 332 of the uni-planar retainer 300.

The uni-planar receiver 300, the uni-planar two-piece positioner 370 and positioner pins 380, the uni-planar retainer 270, and the pressure insert 150 are now pre-assembled into the uni-planar receiver sub-assembly 346 shown in FIGS. 100-101 and 102-103. If the break-off pin guide extensions 398 of the positioner pins 390 have not yet been sheared or broken off at the break-off groove 396, this action may be performed after pre-assembly is complete to leave the receiver sub-assembly 346 with a smooth outer surface suitable for storage, shipping, and eventually use in a surgical setting.

The uni-planar receiver sub-assembly 346 is now in its shipping configuration, in which the uni-planar retainer 270 is securely supported and maintained within the positioner chamber portion 328 of the receiver cavity 326 by the uni-planar two-piece positioner 370, with the retainer 270 being centralized in space above both the receiver bottom opening 336 and the partial spherical seating surface 332. In the shipping configuration the pressure insert 150 is also held in its vertical position within the receiver central bore 314 by the insert ridges 158 being fully enclosed with the receiver upper grooves 320 that are sized and shaped to prevent any upward movement of the pressure insert 150 relative to the uni-planar receiver 300, and to allow for downward movement or deployment of the pressure insert 150 only with considerable direct force that may be provided by the appropriate tooling. Furthermore, in the shipping configuration the pressure insert 150 is also held or 'clocked' in angular position by the inner surfaces of the upper flanges 382 that project inwardly from the positioner wing portions 380 to surround the opposing skirts 164 that project outwardly from the insert base 162.

Illustrated in FIGS. 102-124 is the assembly or coupling of the pre-assembled receiver sub-assembly 346 of the uni-planar pivotal bone anchor assembly 250 to a universal shank head 22 that, optionally, does not also include the removal of the capture recess protection sleeve 50 described above.

Figure 102:
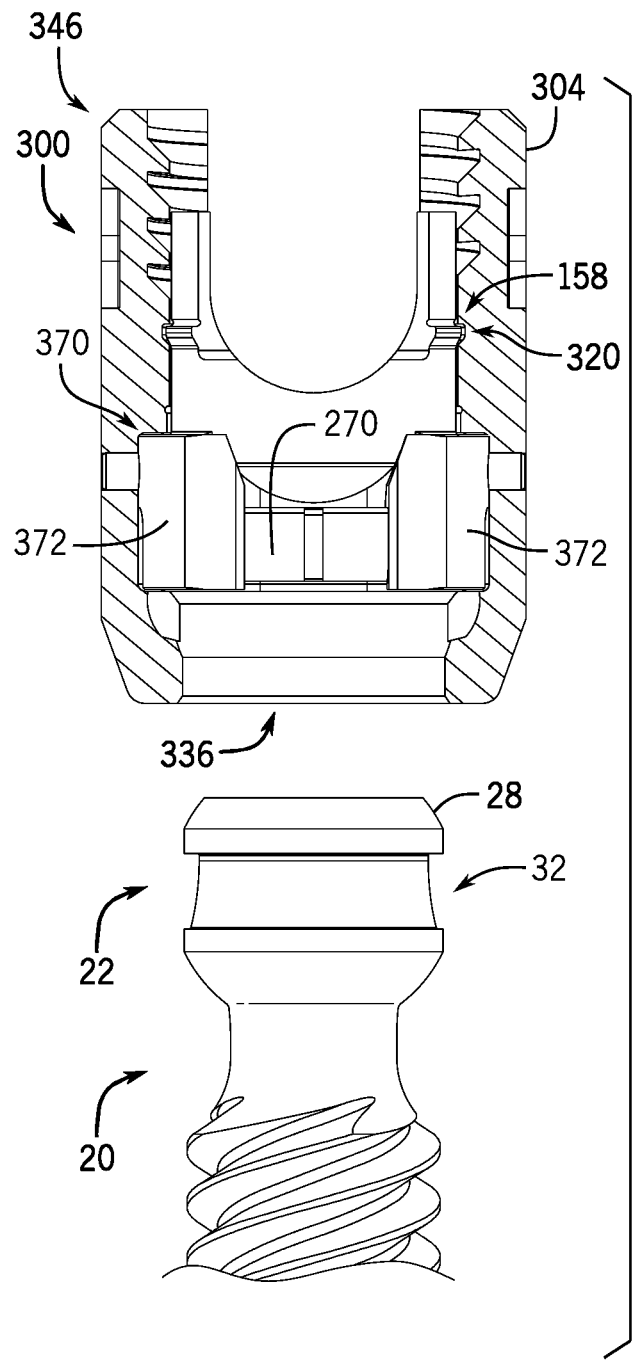
FIG. 102 is a partially cut-away side view of the uni-planar receiver sub-assembly positioned above the universal shank head of a bone anchor.
Figure 103:
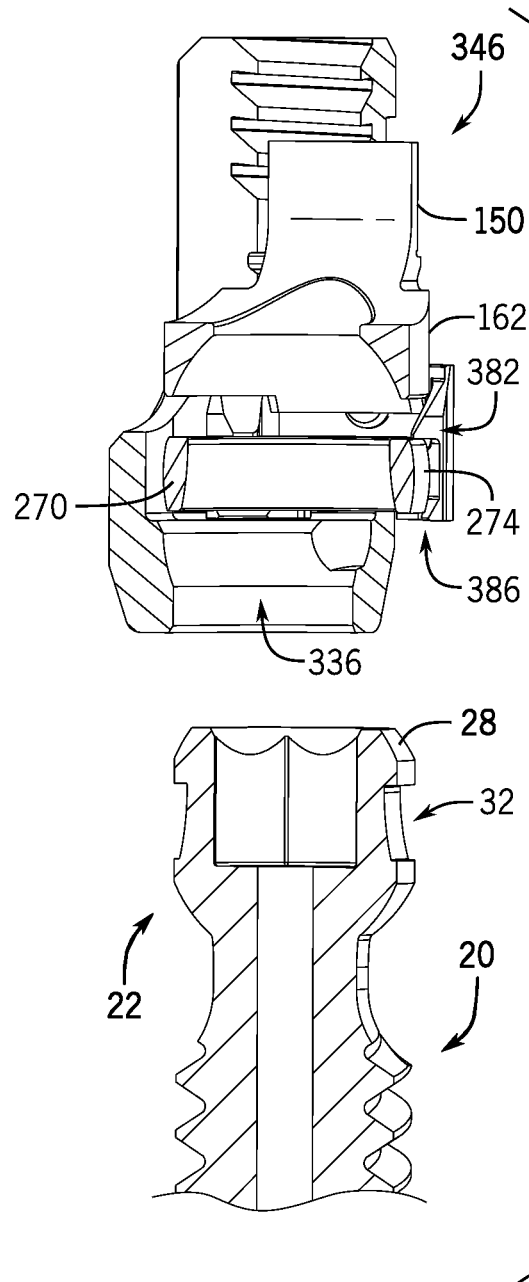
FIG. 103 is a sectioned perspective view of the uni-planar receiver sub-assembly and bone anchor of FIG. 102.

With reference first to FIGS. 102-103, the pre-assembled uni-planar receiver sub-assembly 346 is positioned above the universal shank head 22, with the receiver bottom opening 336 generally aligned with the shank head upper partial spherical surface 28.

Figure 104:
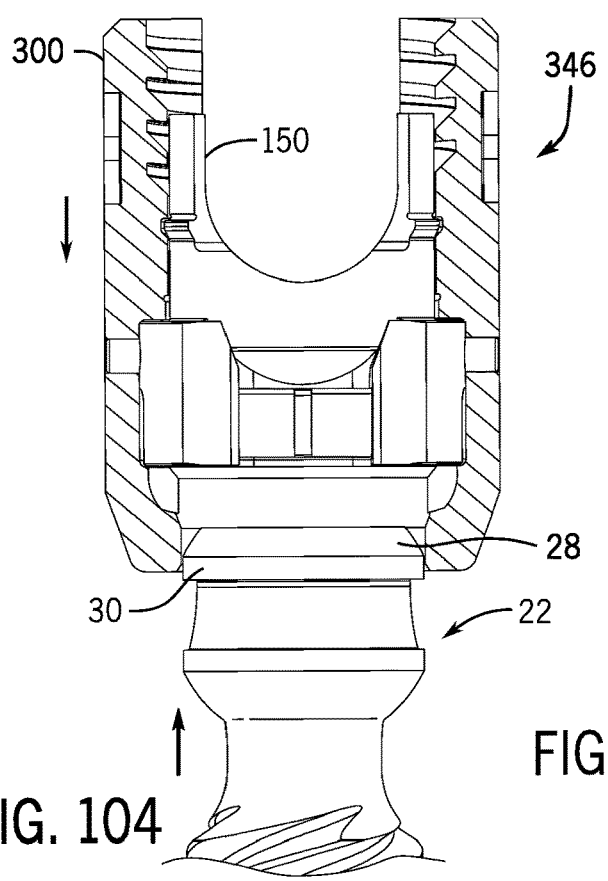
FIG. 104 is a partially cut-away side view of the uni-planar receiver sub-assembly moving downward to contact the universal shank head of the bone anchor.
Figure 105:
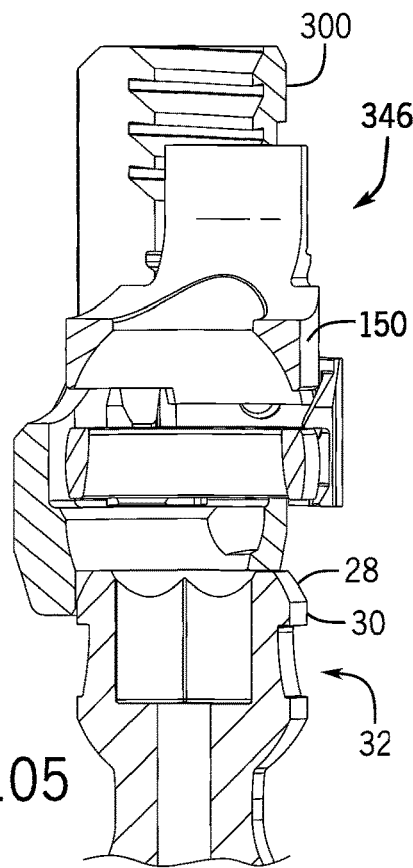
FIG. 105 is a sectioned perspective view of the uni-planar receiver sub-assembly and bone anchor of FIG. 104.

With reference to FIGS. 104-105, the uni-planar receiver sub-assembly 346 is then dropped until the upper partial spherical surface 28 and the upper cylindrical outer surface 30 of the bone anchor enter the receiver bottom opening 336.

Figure 106:
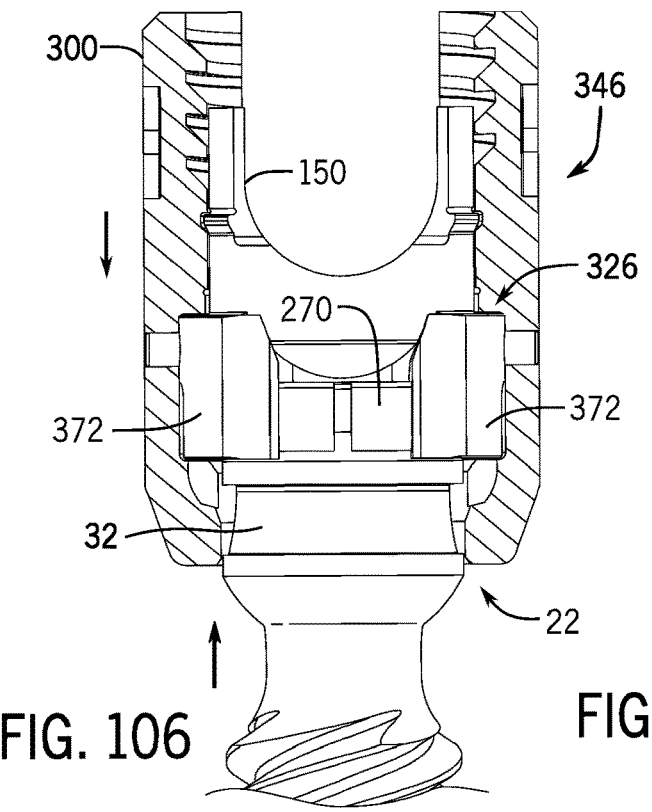
FIG. 106 is a partially cut-away side view of the uni-planar receiver sub-assembly moving further downward until the constrained uni-planar retainer contacts the universal shank head.
Figure 107:
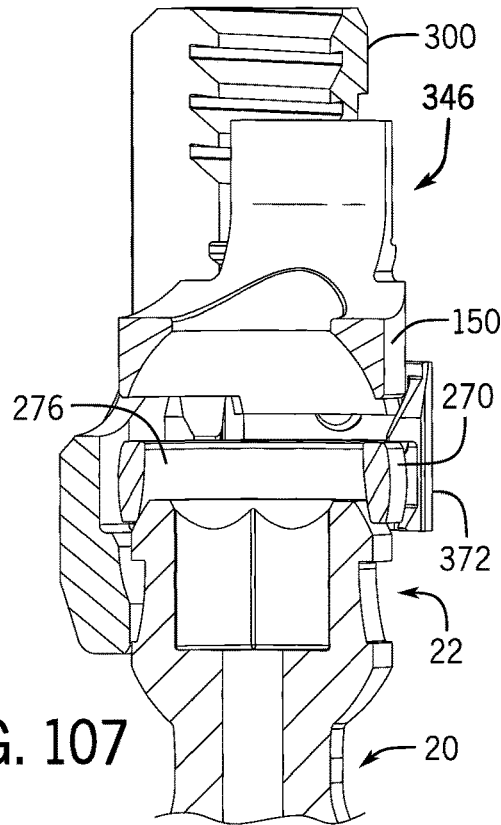
FIG. 107 is a sectioned perspective view of the uni-planar receiver sub-assembly and universal shank head of FIG. 106.

With reference to FIGS. 106-107, the uni-planar receiver sub-assembly 346 is then moved or pushed downward (or the universal shank head is moved upward, depending on the frame of reference of the reader) until the shank head upper partial spherical surface 29 contacts the contacts the inner surface 276 of the uni-planar retainer 270.

Figure 108:
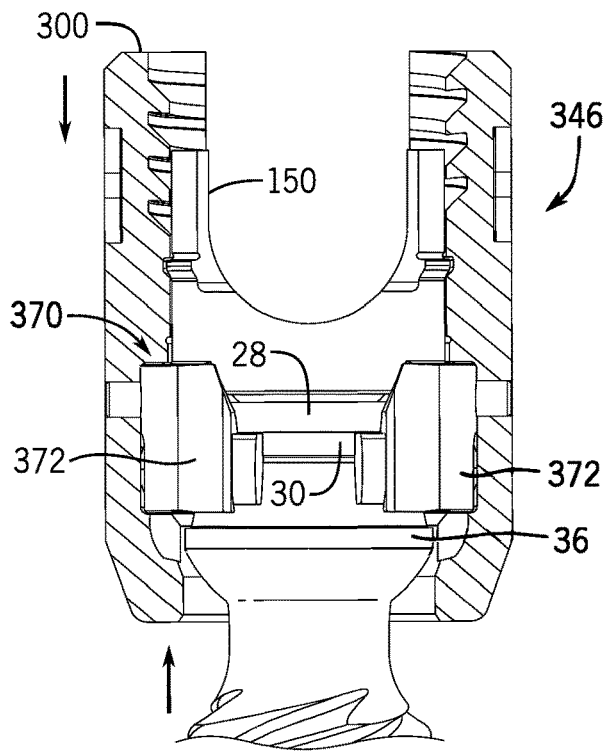
FIG. 108 is a partially cut-away side view of the uni-planar receiver sub-assembly moving further downward until the universal shank head causes maximum expansion of the constrained uni-planar retainer.
Figure 109:
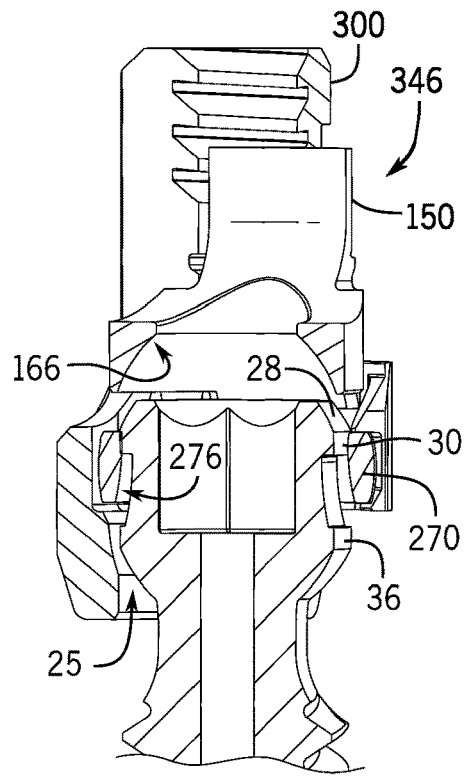
FIG. 109 is a sectioned perspective view of the uni-planar receiver sub-assembly and universal shank head of FIG. 108.

With reference to FIGS. 108-109, the receiver sub-assembly 346 continues downward (or the universal shank head upward) so that first the shank head upper partial spherical surface 28, and then the shank upper cylindrical outer surface 30, bears against the curvate inner surface 276 of the uni-planar retainer 270, causing the expansion of both the retainer 270 and its supporting positioner 370 until the retainer 270 reaches maximum expansion with a narrowest diameter of the curvate inner surface 276 bearing against the shank upper cylindrical outer surface 30.

Figure 110:
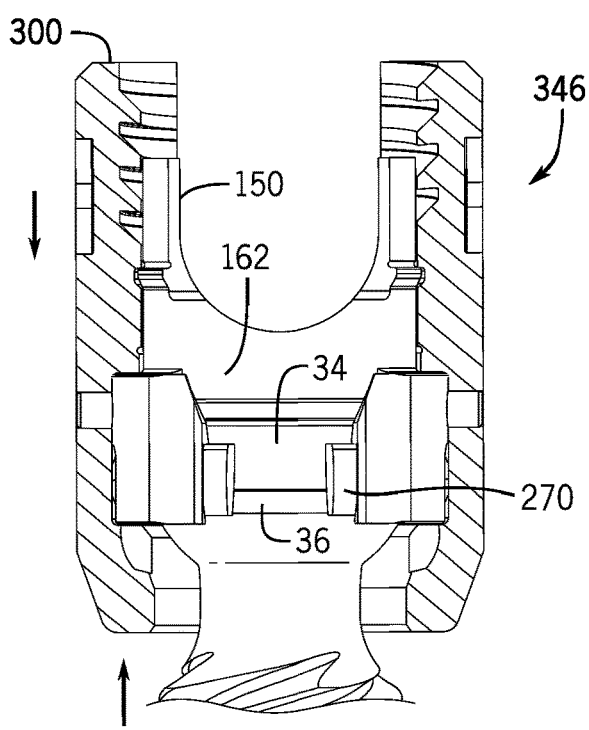
FIG. 110 is a partially cut-away side view of the uni-planar receiver sub-assembly moving further downward until the universal shank head reaches maximum push through within the receiver cavity.
Figure 111:
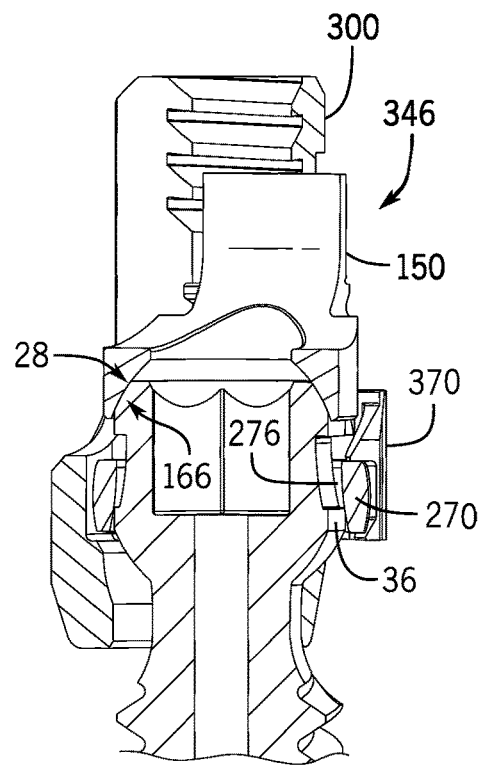
FIG. 111 is a sectioned perspective view of the uni-planar receiver sub-assembly and universal shank head of FIG. 110.

With reference to FIGS. 110-111, the receiver sub-assembly 346 then continues downward (or the shank head upward) until the shank head 22 reaches max push-through in which the shank head upper partial spherical surface 28 abuts the concave bottom surface 166 of the pressure insert 150 and the retainer curvate inner surface 276 bears against the shank lower cylindrical outer surface 36.

Figure 112:
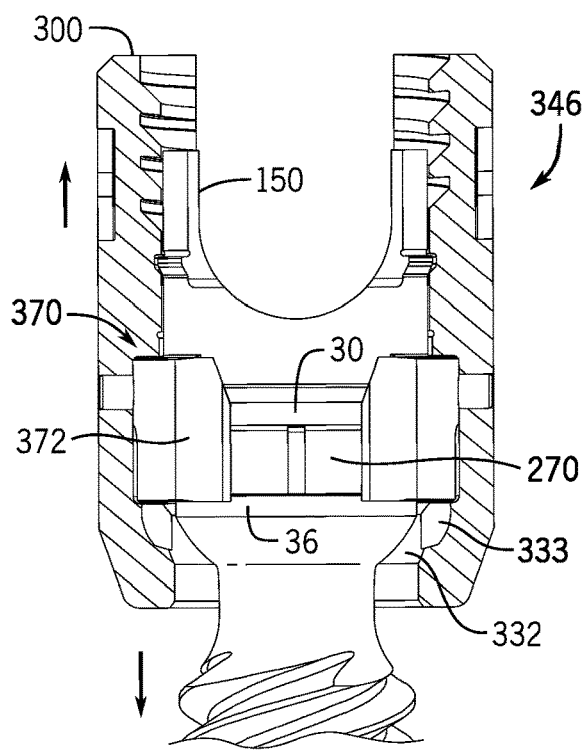
FIG. 112 is a partially cut-away side view of the uni-planar receiver sub-assembly moving back upward until the uni-planar retainer is captured within the horizontal capture recess.
Figure 113:
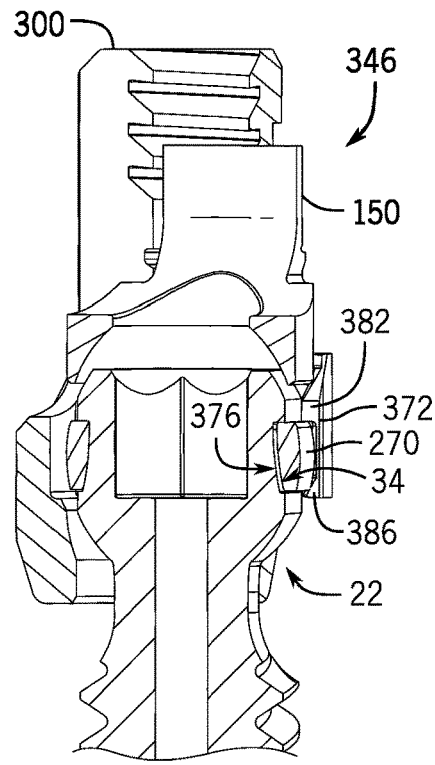
FIG. 113 is a sectioned perspective view of the uni-planar receiver sub-assembly and universal shank head of FIG. 112.

With reference to FIGS. 112-113, the uni-planar receiver sub-assembly 346 is then pulled or moved back upward (or the universal shank head back downward) until the uni-planar retainer 270 snaps into and is captured by the horizontal capture recess 32, with the retainer curvate inner surface bearing 276 against the outwardly-facing inner recess surface 34 of the shank head 22.

Figure 114:
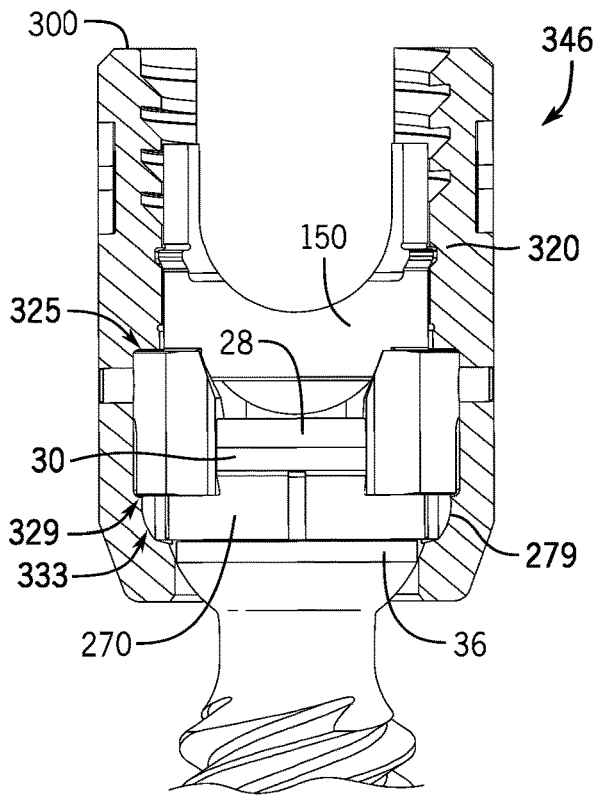
FIG. 114 is a partially cut-away side view of the uni-planar receiver sub-assembly moving further back upward until the uni-planar retainer becomes seated on the receiver partial spherical seating surface.
Figure 115:
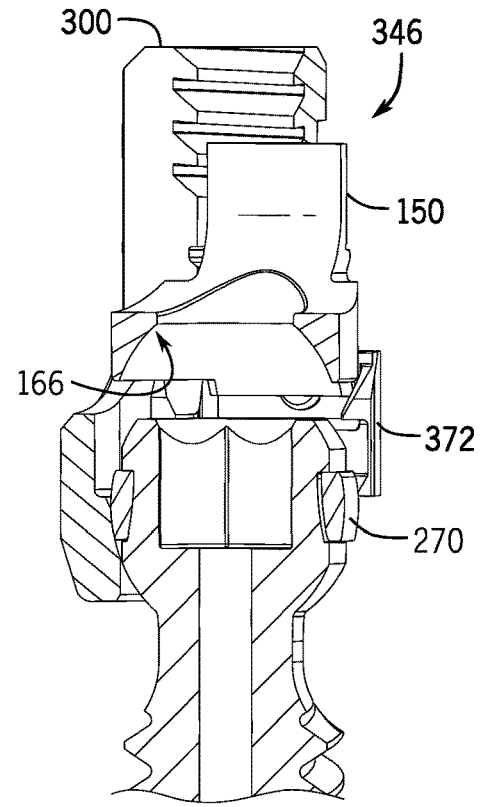
FIG. 115 is a sectioned perspective view of the uni-planar receiver sub-assembly and universal shank head of FIG. 114.
Figure 116:
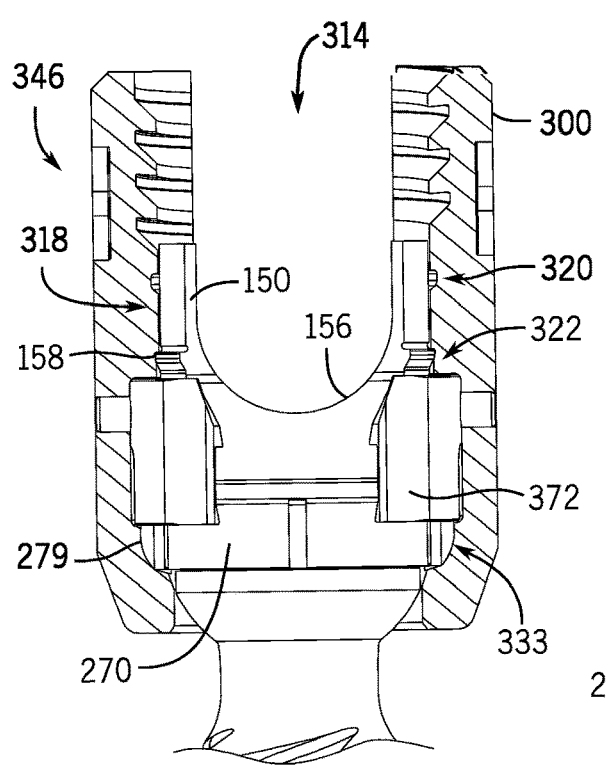
FIG. 116 is a partially cut-away side view of the uni-planar receiver sub-assembly and coupled universal shank head, with the pressure insert in a fully deployed friction fit position.
Figure 117:
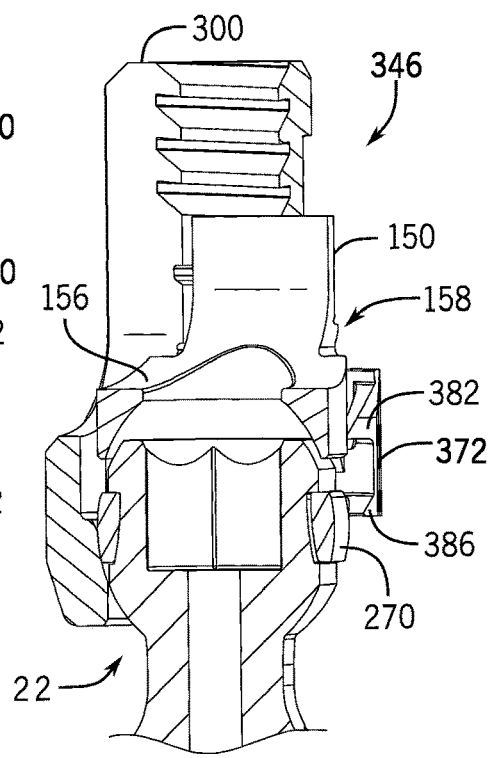
FIG. 117 is a sectioned perspective view of the uni-planar receiver sub-assembly and universal shank head of FIG. 116.

With reference to FIGS. 114-115, the uni-planar receiver sub-assembly 346 then continues back upward (or the universal shank head back downward) while the uni-planar retainer 270 disengages from the uni-planar positioner 370 (which is vertically constrained by the upper and lower step surfaces 325, 329 of the positioner chamber 328) and becomes seated on the partial spherical seating surface of the receiver 322, with the opposed rounded pegs 279 being received back into the opposed pockets 333.

Figure 118:
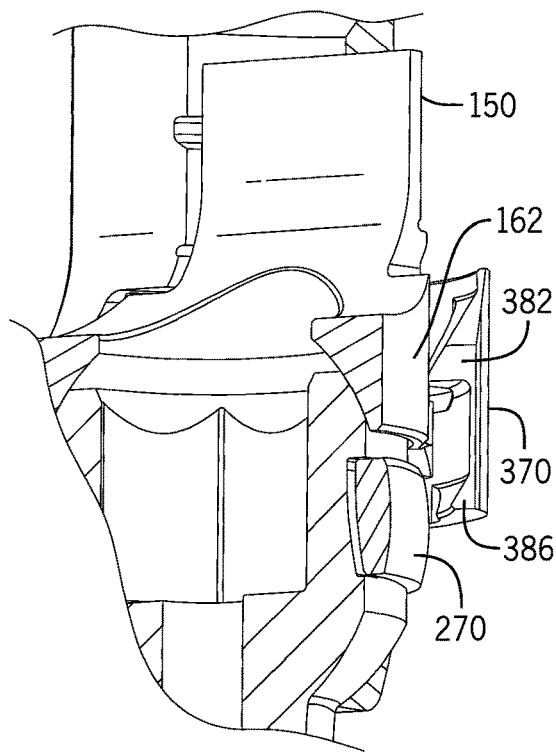
FIG. 118 is a partially cut-way and sectioned perspective view of the uni-planar receiver sub-assembly and universal shank head of FIG. 116.
Figure 119:
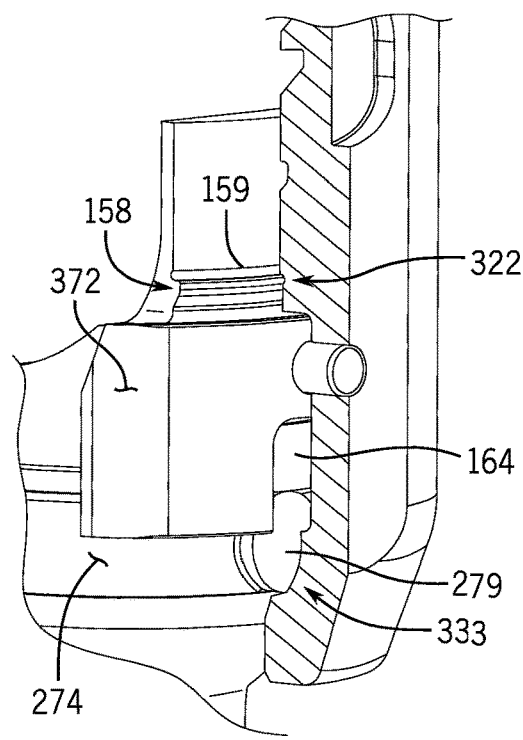
FIG. 119 is another partially cut-way and sectioned perspective view of the uni-planar receiver sub-assembly and universal shank head of FIG. 116.

With reference to FIGS. 116-119, the pressure insert 150 can now be deployed with tooling that bears downwardly on the upper curvate seating surface 156 with considerable force to push the insert ridges 158 downward out of the upper receiver grooves 320 and onto the discontinuous cylindrical surface 318 of the central bore 314 of the receiver 300. The tooling continues to push the insert 150 downward until the insert ridges 158 snap into the lower receiver grooves 322 (as best shown in FIG. 119), at which point the insert concave spherical bottom surface 166 fully engages the shank head upper partial spherical surface 28 and the retainer outer partial spherical surface 274 also fully engages the receiver partial spherical seating surface 332 to establish a friction fit. The friction fit firmly holds the uni-planar receiver 300 to the universal shank head 22 while allowing for movement of the receiver 300 relative to the bone anchor 20 with an applied force.

With reference to FIG. 118, with the pressure insert 150 in the deployed position, the leading edges 383 of the upper positioner protrusions 382 can abut the cylindrical outer surface of the insert base 162 to hold the positioner piece 172 in an expanded position with the lower flanges 386 well-spaced from the now-pivotable retainer 270 and universal shank head 22.

With further reference to FIGS. 119 and 124, the bottom surfaces 165 of the pressure insert skirts 164 can also engage the upper edges of the rounded pegs 279 of the uni-planar retainer 270, to secure and hold the pegs 279 down within their respective pockets 333 when transverse loads or out-of-plane bending moments are applied to the uni-planar receiver 300 by the shank acting on the uniplanar pivoting retainer.

Figure 120:
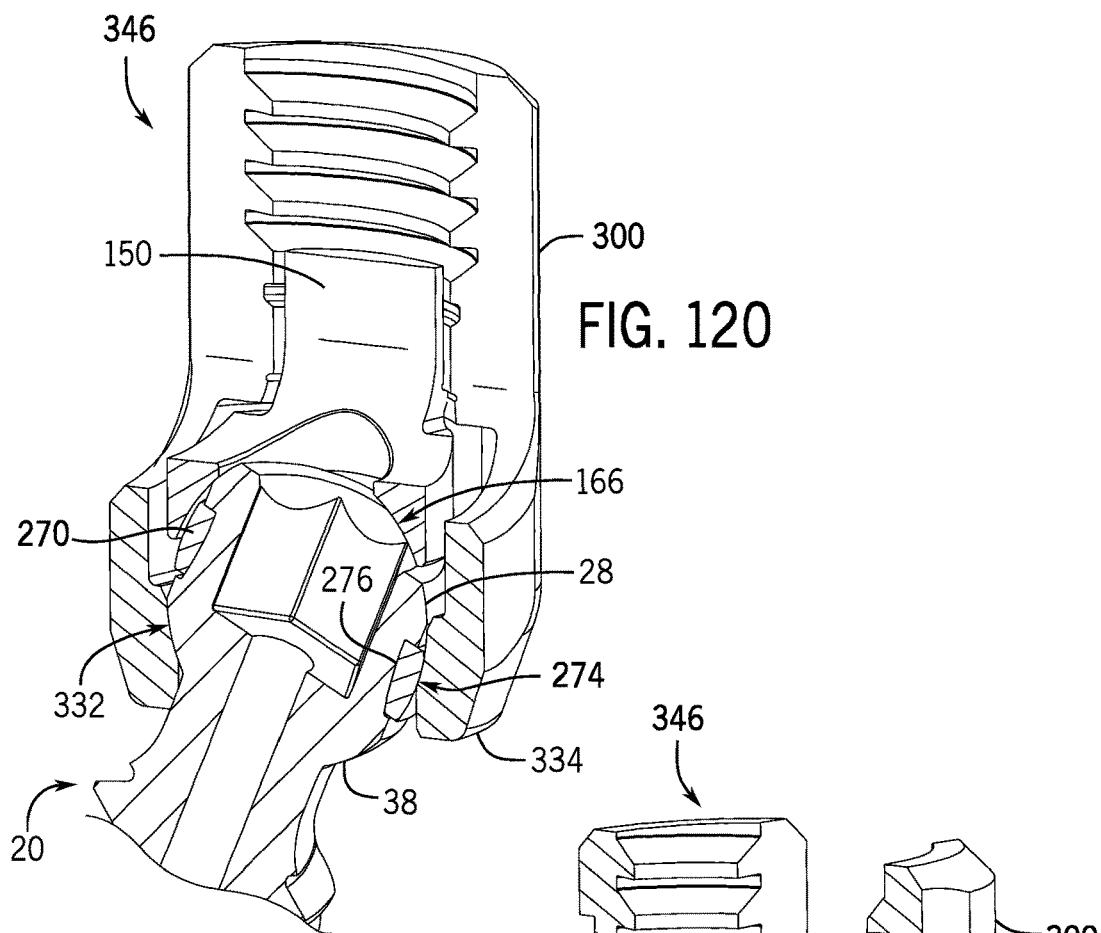
Figure 121:
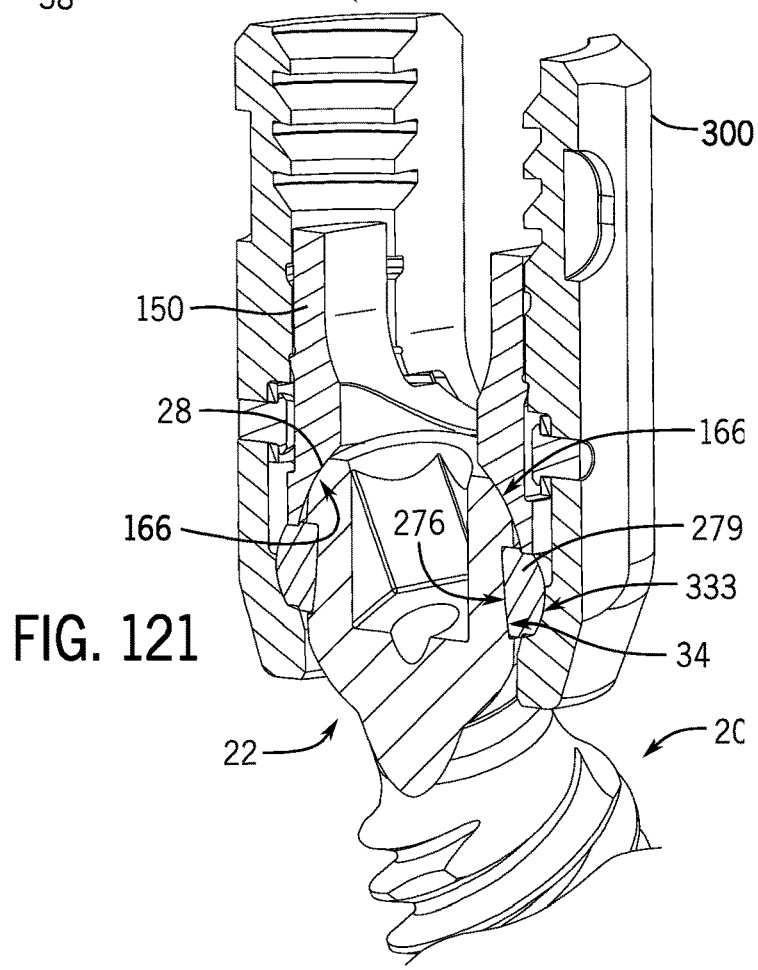

With reference to FIGS. 120-121, the friction fit engagement of the uni-planar receiver sub-assembly to the universal shank head 22 of the bone anchor 20 can provide the surgeon or medical professional with a number of alignment options. For example, the friction fit allows for rotation of the uni-planar receiver 300 around the universal shank head 22, with an applied axial twisting force, so as to align the receiver channel 306 with the receiver channels of an adjacent pivotal bone anchor assembly. However, because the pegs 279 of the uni-planar retainer 270 are constrained from moving by the opposing pockets 333 formed into lower seating surface 332, in the uni-planar embodiment the rotational motion can be provided by the sliding of the inner surface 276 of the uni-planar retainer 270 across the outwardly-facing inner recess surface 34 of the horizontal capture recess 32.

The friction fit also allows for angulation of the uni-planar receiver 300 relative the shank head 22, with an applied tangential moment force, also to align the receiver channel 306 with the receiver channels of an adjacent bone anchor assembly, through sliding frictional engagement between the retainer outer partial spherical surface 274 relative to the receiver partial spherical seating surface 332. This angulation is limited to a single plane, however, due to the internal moment created by the retainer pegs 279 abutting against both the sidewalls of the surrounding pockets 333 and the underside surfaces 165 of the overlying skirts 164 of the pressure insert 150, thereby preventing the uni-planar retainer 270 (and the attached shank head) from rotating in any direction other than around the axis defined by the opposed retainer pegs 279.

The friction fit is provided from above by sliding frictional engagement between the insert concave spherical bottom surface 166 and the shank head upper partial spherical surface 28 and/or the retainer outer partial spherical surface 274, and from below by sliding frictional engagement between the receiver partial spherical seating surface 332 and the retainer outer partial spherical surface 274 and/or the shank head lower partial spherical surface 38.

Figure 122:
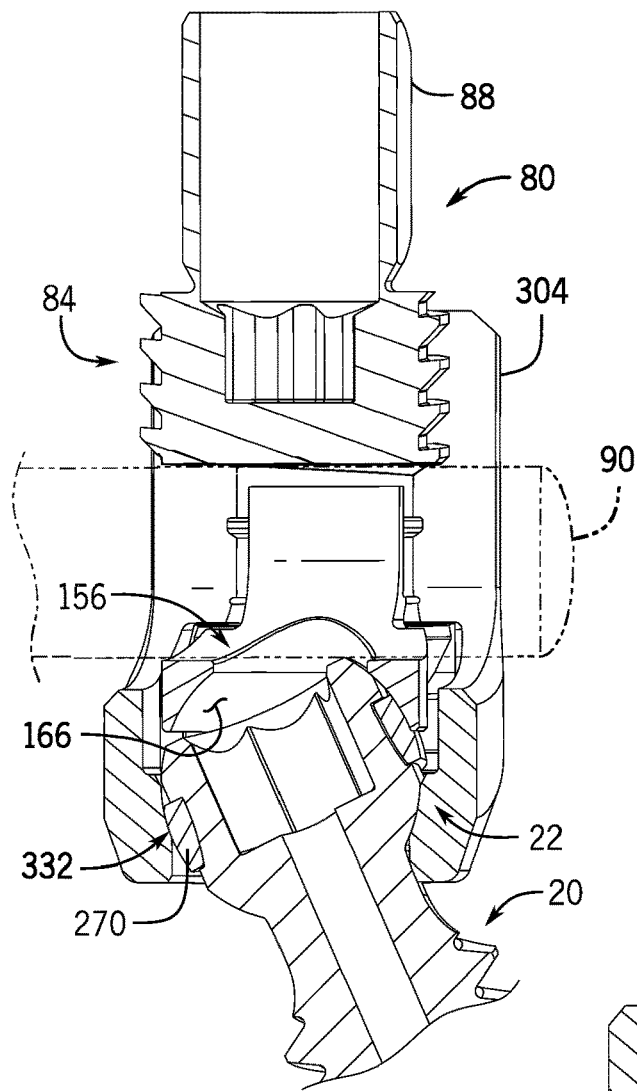
Figure 123:
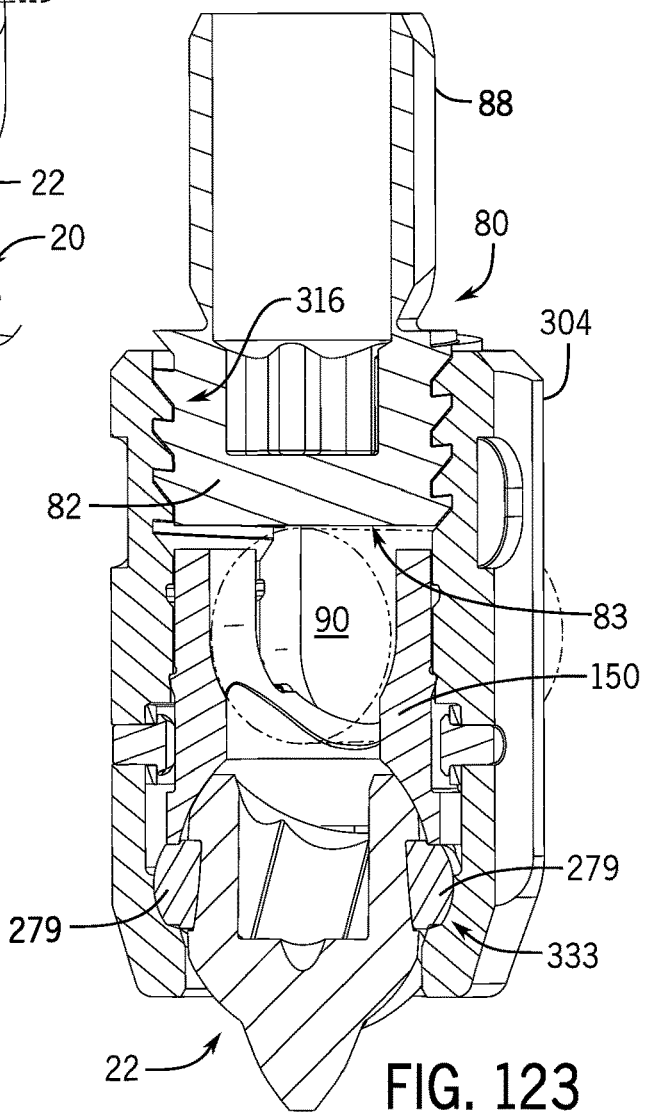

With reference to FIGS. 122-123, the full assembly of an elongate rod 90 and a closure 80 to uni-planar receiver sub-assembly may now be completed. First, after a desired alignment and/or positioning of the uni-planar receiver sub-assembly 346 to the bone anchor 20 has been achieved, the elongate rod 90 can then be installed (i.e. reduced) into the receiver channel 306 until the underside surface of the rod engages the upper curvate rod seating surface 156 of the insert channel 154. The closure 80 can then be installed into the upper portion of the receiver central bore 314, in which the continuous guide and advancement structure 84 of the closure body 82 engages the discontinuous guide and advancement structure 316 formed into the interior faces 310 of the receiver upright arms 304.

The closure 80 can be threaded downwardly until the bottom surface 83 of the closure engages the top surface of the elongate rod 90. Further rotation/torqueing of the closure 80 can then be used to drive the elongate rod 90 downward into the pressure insert 150, which in turn drives the universal shank head 22 and uni-planar retainer 270 downward into the receiver partial spherical seating surface 332 to achieve a final locking of the uni-planar bone anchor assembly 250, in which the uni-planar receiver sub-assembly 346 can no longer move relative to the bone anchor 20.

With reference to FIG. 124, the closure break-off tab 88 can be sheared from the closure body 42 at a pre-determine torque value, thereby ensuring that the pivotal bone anchor assembly is fully locked.

Illustrated in FIGS. 125-130 is another representative embodiment of a multi-planar pivotal bone anchor apparatus or assembly 410 in which the elongate rods and receivers have been replaced with multi-planar housings 420 that provide for adjacent level connection. For example, the multi-planar housings 420 of the pivotal bone anchor assemblies 410 can replace the multi-planar receivers discussed above with respect to FIGS. 1-69, with the housings 420 containing a number of multi-planar components, namely, a multi-planar retainer 436 and a multi-planar two-piece positioner 440, that are substantially the same as those multi-planar components described above as residing in the multi-planar pivotal bone anchor assembly 10 shown in FIGS. 1-69.

Figure 125:
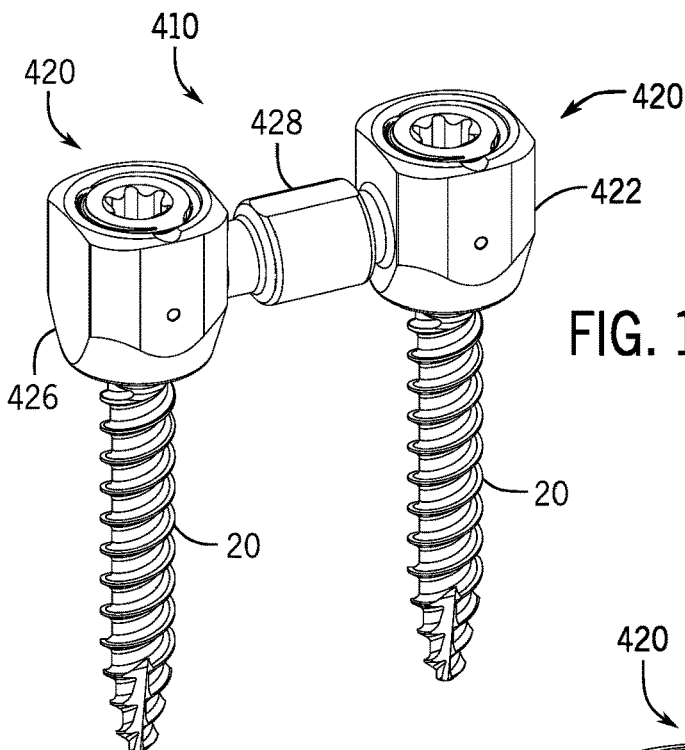
Figure 126:
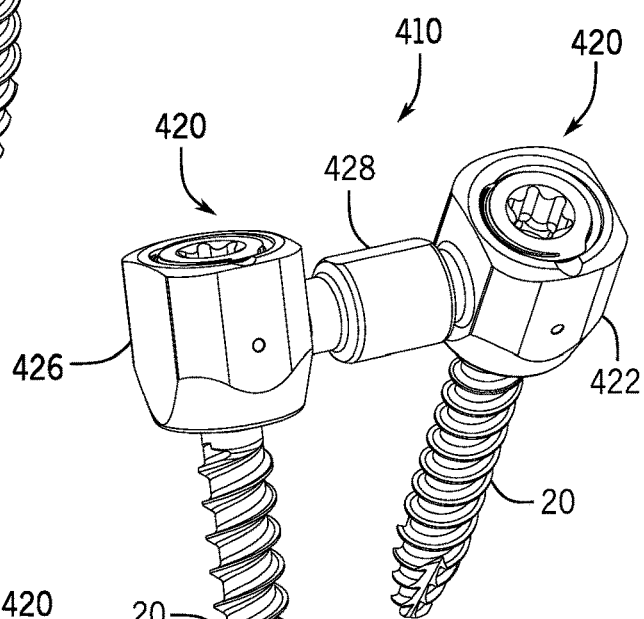
Figure 127:
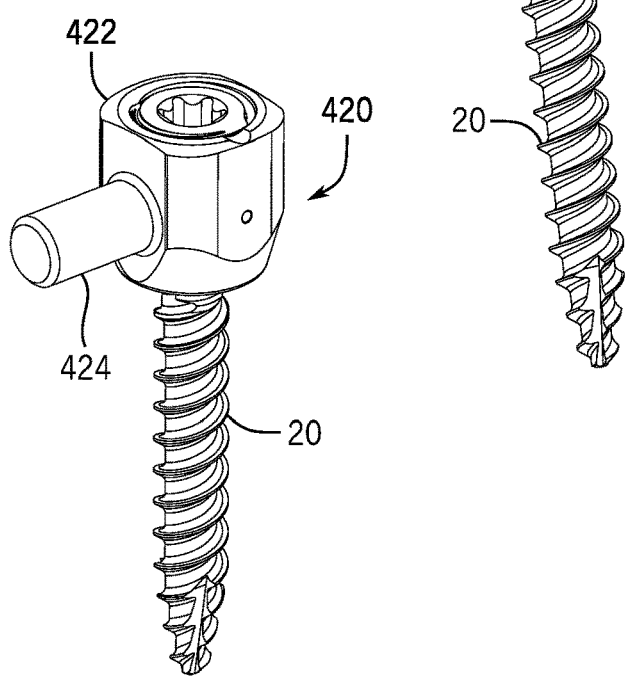

As shown in FIGS. 125-127, in one aspect the housings 420 of the pivotal bone anchor assembly 410 can be separated into a male housing 422 having a male chord projection 424 that is received in pivotal arrangement within a female receptacle 428 of a female housing 426 immediately adjacent the male housing 422.

Figures 128, 129, 130:
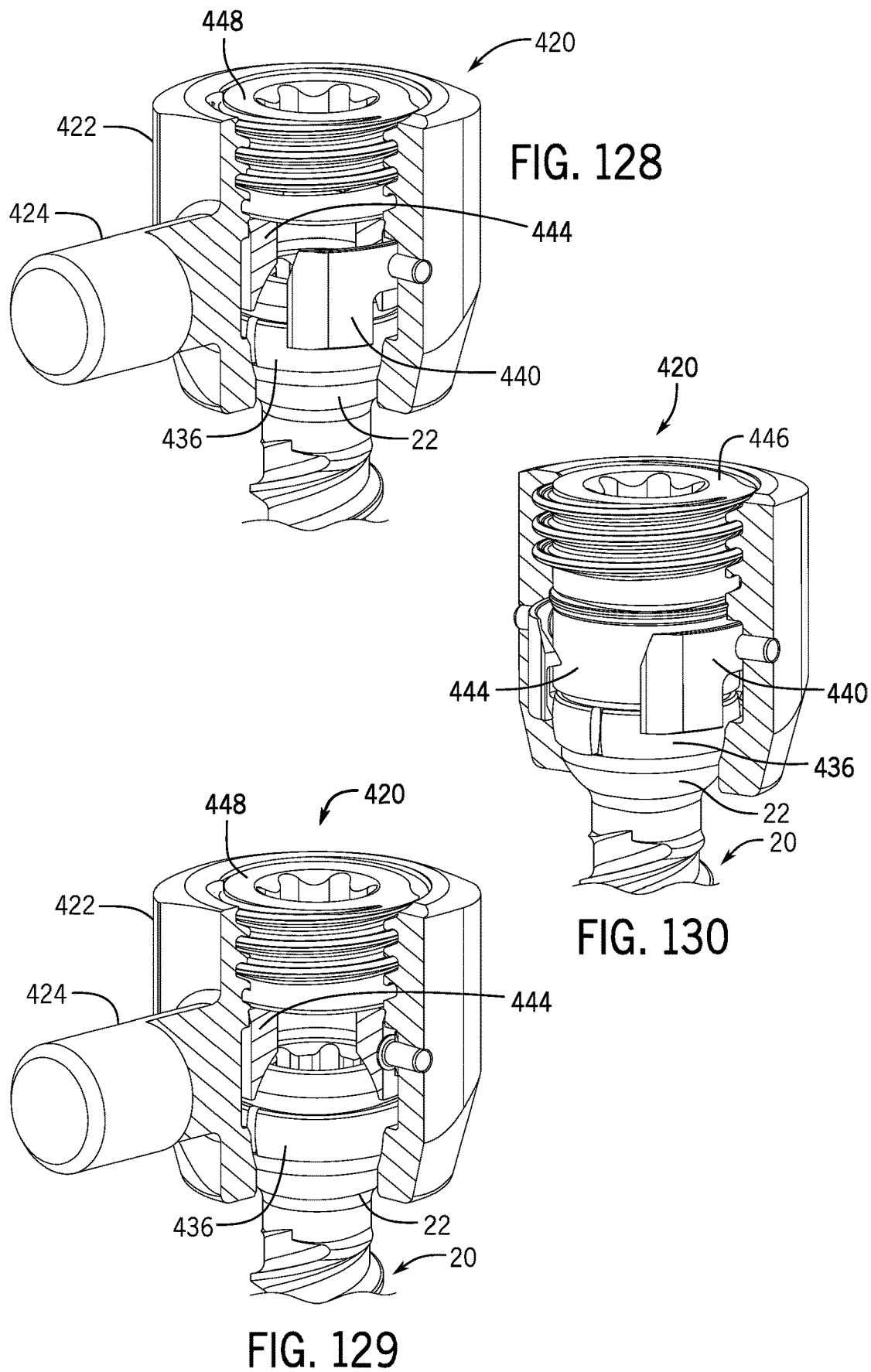

As shown in FIGS. 128-130, the multi-planar housings 420 can further include a separate pressure insert 444 that has been modified to remove the upwardly projecting arm structures that define an insert channel, while still including external structure that can provide for the downward deployment of the insert 444 to a non-floppy friction fit around the universal shank head 22 prior to the installation of the closure 448. With the housings 420 so equipped with these internals, each housing is also able to couple with the above-described universal shank heads 22 located at the_proximal ends of the bone anchors 20, as generally outlined above with respect to FIGS. 1-124.

As shown in FIGS. 131-132, in another embodiment the multi-planar housings 420 of the multi-planar pivotal bone anchor apparatus or assembly 410 can include a multi-planar female housing 430 having a female receptacle 432 that has been modified to include a set screw 434 that is configured to lock a male chord projection (not shown) within the female receptacle 432. As can be seen in the drawings, the remaining components of the multi-planar pivotal bone anchor assembly 410, namely the multi-planar retainer 436, the multi-planar pined two-piece positioner 440, the pressure insert 444, and the closure 448 can be the same as those described above with reference to FIGS. 125-130.

FIGS. 133-134 illustrate the same concept discussed above with respect to FIGS. 125-132, except employ multi-planar housings 460 with different exterior features and a one-piece positioner 480 that replaces the two-piece positioner 440 described above with respect to the multi-planar pivotal bone anchor apparatus or assembly 410 of FIGS. 125-132. Besides the one-piece 480 and two-piece positioners 440 respectively discussed with respect to FIGS. 133-134 and 125-132, it is foreseen that other multi-piece positioners may be employed, such as for example, three-piece, four-piece, and so forth, or even no positioner, wherein the multi-planar retainer is self-positioning, or aspects of the pressure insert 484 or of the receiver or housing 460 act against the multi-planar retainer 476 to position it within the receiver or housing 460. The housings 460 of FIGS. 133-134 can also include the separate pressure insert 484 that has been modified from that shown in FIGS. 1-124 to remove the upwardly projecting arm structures that defined an insert channel, while still including external structure that can provide for the downward deployment of the pressure insert 484 to a non-floppy friction fit around the universal shank head 22 located at the proximal ends of the bone anchor 20, prior to the installation of the closure 488.

As can be understood by a comparison of the embodiments of the multi-planar receiver 100 and the uni-planar receiver 300 illustrated in FIGS. 1-124 and the embodiments of the adjacent level housings 420, 460 illustrated in FIGS. 125-135, both the receivers 100, 300 and the housings 420, 460 have substantially the same retainer coupling internals, namely, a pivoting retainer, a positioner (one- or two-piece), and a modified pressure insert residing therein, and which components are coupled to or deployed against the universal shank head 22 of the bone anchor 20 in similar fashions and operations. The receivers 100, 300 and housings 420, 460 thus may be considered different versions of a structural envelope that contains the internal retainer ring, positioner, and pressure insert.

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated and exemplary embodiments of the composite substrate without departing from the spirit and scope of the invention. These and other revisions might be made by those of skill in the art without departing from the spirit and scope of the invention that is constrained only by the following claims.

What is claimed is:

1. A pivotal bone anchor system for securing an elongate rod to a bone of a patient via closure tops, the pivotal bone anchor system comprising:
   a plurality of bone anchors, each bone anchor comprising a longitudinal axis, a capture portion having a rounded shape with a midsection defining a hemisphere plane perpendicular to the longitudinal axis, and a unitary anchor portion opposite the capture portion configured for attachment to the bone, the capture portion being without flat side faces and including at least one outer engagement surface extending entirely circumferentially around the capture portion at the hemisphere plane;
   at least one multi-planar receiver sub-assembly comprising:
      a multi-planar receiver having an upper channel portion configured to receive the elongate rod and a lower base portion defining an internal cavity having a substantially continuous circumferential partial spherical seating surface proximate a bottom opening, and
      a multi-planar pivoting retainer having a circumferential partial spherical outer surface configured for multi-planar motion upon engagement with the seating surface of the internal cavity of the multi-planar receiver, and an inner surface configured to engage the at least one outer engagement surface of one of the plurality of bone anchors to capture the bone anchor within the internal cavity of the multi-planar receiver; and
   at least one uni-planar receiver sub-assembly comprising:
      a uni-planar receiver having an upper channel portion configured to receive the elongate rod and a lower base portion defining an internal cavity having a non-continuous circumferential partial spherical seating surface proximate a bottom opening with opposing pockets formed therein, and a uni-planar pivoting retainer having a non-continuous circumferential partial spherical outer surface with opposite pegs projecting outward therefrom, the partial spherical outer surface and pegs configured for uni-planar motion upon engagement with the seating surface and opposing pockets of the internal cavity of the uni-planar receiver, respectively, and an inner surface configured to engage the at least one outer engagement surface of another of the plurality of bone anchors to capture the bone anchor within the internal cavity of the uni-planar receiver, wherein the capture portion of each of the plurality of bone anchors comprises a shared singular geometric shape that is configured for capture by either of the at least one multi-planar receiver sub-assembly or the at least one uni-planar receiver sub-assembly without further modification or adjustment.

2. The pivotal bone anchor system of claim 1, wherein the capture portion further comprises an upper partial spherical outer surface above the hemisphere plane, a lower partial spherical outer surface below the hemisphere plane.

3. The pivotal bone anchor system of claim 2, wherein a radius of the upper partial spherical outer surface and a radius of lower partial spherical outer surface of the capture portion of the each of the plurality of bone anchors are substantially equal to the radii of the partial spherical outer surfaces of both the multi-planar and the uni-planar retainers.

4. The pivotal bone anchor system of claim 1, wherein the at least one outer engagement surface of the capture portion of each bone anchor further comprise an inner recess surface extending into and circumferentially around the capture portion at the hemisphere plane and an upper annular ledge surface that together define a horizontal capture recess.

5. The pivotal bone anchor system of claim 4, wherein the inner surfaces of each multi-planar and uni-planar retainer is configured to snap into and engage the inner recess surface of the horizontal capture recess with a substantially neutral fit.

6. The pivotal bone anchor system of claim 4, wherein the inner recess surface of each bone anchor is complementary with the inner surfaces of the multi-planar and the uni-planar retainers.

7. The pivotal bone anchor system of claim 4, wherein the inner recess surface of each bone anchor further comprise a curved profile that curves downwardly and outwardly as moving from the upper annular ledge surface to a lower annular ledge surface.

8. The pivotal bone anchor system of claim 4, wherein the inner recess surface of each bone anchor further comprises a cylindrical profile that is substantially parallel with the longitudinal axis of the bone anchor.

9. The pivotal bone anchor system of claim 4, wherein the inner recess surface of each bone anchor further comprises a conical profile that is angled downwardly and outwardly with respect to the longitudinal axis of the bone anchor.

10. The pivotal bone anchor system of claim 1, wherein the capture portions of each bone anchor are configured to be uploaded through the bottom openings and into the internal cavities of the multi-planar and uni-planar receivers, respectively, prior to capture by the multi-planar and uni-planar retainers.

11. The pivotal bone anchor system of claim 1, wherein each of the at least one multi-planar receiver sub-assembly and the at least one uni-planar receiver sub-assembly further comprises a positioner located in the internal cavity of the multi-planar or uni-planar receiver and configured to stabilize and centralize the multi-planar or uni-planar retainer above the bottom opening of the receiver.

12. The pivotal bone anchor system of claim 11, wherein the positioner located in the internal cavity of the multi-planar or uni-planar receiver further comprises two positioner pieces having center portions pinned to interior vertical sidewalls of the receiver cavity.

13. The pivotal bone anchor system of claim 1, wherein each of the at least one multi-planar receiver sub-assembly and the at least one uni-planar receiver sub-assembly further comprises a pressure insert located in an upper first position in the upper channel portion of the multi-planar or uni-planar receiver with the pressure insert having outwardly extending protrusions engagable with opposing upper grooves formed into the upper channel portion so as to prevent the pressure insert from moving back up within the upper channel portion.

14. The pivotal bone anchor system of claim 13, wherein after a bone anchor capture portion is captured by the at least one multi-planar receiver sub-assembly or the at least one uni-planar receiver sub-assembly, respectively, the pressure insert is downwardly deployable in the upper channel portion from the upper first position to a lower second position by a tool, in which the insert outwardly extending protrusions are pushed downwardly from the opposing upper grooves and into engagement with opposing lower grooves also formed into the upper channel portion.

15. The pivotal bone anchor system of claim 14, wherein the pressure insert being located in the lower second position in the upper channel portion of the multi-planar or uni-planar receiver further comprises a friction fit position in which a bottom surface of the pressure insert becomes engaged with the upper partial spherical outer surface of the bone anchor capture portion with a non-floppy friction fit.

16. The pivotal bone anchor system of claim 1 and further comprising the elongate rod and a plurality of closure tops, wherein each of the plurality of closure tops is configured for positioning entirely within the upper channel portion of one the multi-planar or uni-planar receivers above the elongate rod and in engagement with a mating structure formed into the upper channel portion to apply a downward pressure to a top of the elongate rod, so as to secure the elongate rod to the bone of the patient.

* * * * *